United States Patent
Koontz et al.

(10) Patent No.: US 7,098,311 B2
(45) Date of Patent: Aug. 29, 2006

(54) FUSION OF JAZF1 AND JJAZ1 GENES IN ENDOMETRIAL STROMAL TUMORS

(75) Inventors: Jason Koontz, Brookline, MA (US); Jeffrey Sklar, Chestnut Hill, MA (US)

(73) Assignee: Brigham and Women's Hospital, Boston, MA (US)

( * ) Notice: Subject to any disclaimer, the term of this patent is extended or adjusted under 35 U.S.C. 154(b) by 182 days.

(21) Appl. No.: 09/874,162

(22) Filed: Jun. 4, 2001

(65) Prior Publication Data

US 2002/0155452 A1 Oct. 24, 2002

Related U.S. Application Data

(60) Provisional application No. 60/209,093, filed on Jun. 2, 2000.

(51) Int. Cl.
*C07K 1/00* (2006.01)
*A61K 39/00* (2006.01)

(52) U.S. Cl. .................... 530/350; 424/277.1
(58) Field of Classification Search ............... 530/350; 424/277.1
See application file for complete search history.

(56) References Cited

FOREIGN PATENT DOCUMENTS

WO  WO 01/55322  *  8/2001

OTHER PUBLICATIONS

Abstract of Ambros (Materia Medica Polona, 1992, vol. 24, pp. 76-78).*
Abstract of Chan et al (Molecular and Cellular Probes, 1987, vol. 1, pp. 73-82).*
Abstract of Sonobe et al (Cancer Genet Cytogenet, Jul. 1999, vol. 112, pp. 34-37).*
Abstract of Chu et al (American Journal of Clinical Pathology, Mar. 2000, vol. 113, pp. 374-382).*
Abstract of Nagase et al (DNA Research, 1995, vol. 2, pp. 167-174).*
Accession No. Q15022, Mar. 2003.*
Accession No. AAU15978, Nov. 2001.*
Nagase et al (DNA Research, 1995, vol. 2, pp. 167-174).*
Berg, J.M., et al., (1996) Science 271, 1081-1085.
Clarke, N.D. et al., (1998) sCIENCE 282, 2018-2022.
Dal Cin, P., et al., (1992) Cancer Genet. Cytogenet. 53, 43-46.
Hennig, Y., et al., (1997) Cancer Genet. Cytogenet. 98, 84-86.
Koontz, J., et al., (2001) Proceedings of the National Academy of Sciences, vol. 98, No. 11, 6348-6353.
Nasmyth, K., et al., (2000) Science 288, 1379-1384.
Pauwels, P., et al., (1996) Histopathology 29, 84-87.
Sreekantaiah, C., et al., (1991) Cancer Genet. Cytogenet. 55, 163-166.
Xu, Z., et al., (1998) Genetics 150, 1419-1428.
Yamamoto, A., et al., (1996) J. Cell Biol. 133, 85-97.
Yamamoto, A., et al., (1996) J. Cell Biol. 133, 99-110.
Database GenBank, Accession No. AI595264, Marra, M. et al. 1999; the eDNA molecule comprises a polynucleotide sequence that is 70.7%identical over its entire length to SEQ ID No. 3 and also comprises a polynucleotide sequence of SEQ ID No. 1.
Database GenBank, Accession No. AK000711, Direct Submission, Sugano, S., et al. Feb. 15, 2000; the eDNA molecule comprises a polynucleotide sequence that is 100% identical to a polynucleotide sequence of SEQ ID No. 3.

* cited by examiner

*Primary Examiner*—Karen A. Canella
(74) *Attorney, Agent, or Firm*—Fish & Richardson P.C.

(57) ABSTRACT

The invention provides isolated nucleic acids molecules, designated jAZF1, jjAZ1 or jAZF1/jjAZ1 nucleic acid molecules. The invention also provides antisense nucleic acid molecules, recombinant expression vectors containing jAZF1, jjAZ1 or jAZF1/jjAZ1 nucleic acid molecules, host cells into which the expression vectors have been introduced, and nonhuman transgenic animals in which a jAZF1, jjAZ1 or jAZF1/jjAZ1 gene has been introduced or disrupted. The invention still further provides isolated jAZF1, jjAZ1 or jAZF1/jjAZ1 proteins, fusion proteins, antigenic peptides and anti-jAZF1, jjAZ1 or jAZF1/jjAZ1 antibodies. Diagnostic methods utilizing compositions of the invention are also provided.

1 Claim, 7 Drawing Sheets

```
CCCGCCCGGCGCTCGCAGAGCCGACACCAGGGGGGCTCTCGATGTAGCACCATGACAGGCATCGCCGCCGCCTCCTTCTTCTCCAATACC           90
                                                 T  G  I  A  A  A  S  F  F  S | N  T |
TGCCGATTCGGGGGCTGCGGACTCCACTTCCCCACCCTGGCCGACCTCATCGAGCACATCGAGGACAACCACATCGATACAGATCCACGG          180
| C  R  F  G  G  C  G  L  H  F  P  T  L  A  D  L  I  E  H  I  E  D  N  H | I  D  T  D  P  R
GTTTTAGAAAAACAAGAATTACAGCAGCCAACCTATGTTGCCCTGAGTTACATAAATAGATTCATGACAGATGCTGCCCGCCGAGAGCAG          270
 V  L  E  K  Q  E  L  Q  Q  P  T  Y  V  A  L  S  Y  I  N  R  F  M  T  D  A  A  R  R  E  Q
GAGTCCCTAAAGAAGAAGATTCAGCCGAAGCTCTCGCTGACTCTGTCCAGCTCAGTGTCTCGAGGGAATGTGTCCACTCCCCCACGCCAC          360
 E  S  L  K  K  K  I  Q  P  K  L  S  L  T  L  S  S  S  V  S  R  G  N  V  S  T  P  P  R  H
AGCAGTGGAAGCCTTACTCCCCCCGTGACCCCACCCATCACCCCCTCCTCTTCATTCCGCAGCAGCACTCCGACAGGCAGCGAGTATGAC          450
 S  S  G  S  L  T  P  P  V  T  P  P  I  T  P  S  S  S  F  R  S  S  T  P  T  G  S  E  Y  L
GAGGAGGAGGTGGACTATGAGGAGTCGGACAGCGATGAGTCCTGGACCACAGAGAGTGCCATCAGCTCCGAAGCCATCCTCAGCTCCATG          540
 E  E  E  V  D  Y  E  E  S  D  S  D  E  S  W  T  T  E  S  A  I  S  S  E  A  I  L  S  S  M
TGCATGAATGGAGGGGAAGAGAAGCCTTTTGCCTGCCCAGTTCCTGGATGTAAAAAGAGATACAAGAATGTGAATGGCATAAAGTATCAC          630
 C  M  N  G  G  E  E  K  P | F  A  C  P  V  P  G  C  K  K  R  Y  K  N  V  N  G  I  K  Y  H|
GCTAAGAATGGTCACAGAACACAGATTCGTGTCCGCAAACCATTCAAGTGTCGCTGTGGGAAGAGTTACAAGACAGCTCAGGGCCTGCGG          720
|A  K  N  G  H| R  T  Q  I  R  V  R  K  P | F  K  C  R  C  G  K  S  Y  K  T  A  Q  G  L  R|
CACCACACAATCAATTTCCATCCCCCGGTGTCGGCTGAGATTATCAGGAAGATGCAGCAATAACATGCTGGTCATAACTGTGCCAAGAAA          810
|H  H  T  I  N  F  H| P  P  V  S  A  E  I  I  R  K  M  Q  Q
TCCTCACCAGCAGTTGCTGATTTTGAAAACAGCCACCTTTTTTCAGGGGAAGCATTCAGCAACCCTTTAAAGAAAAAGAATTAAATGCAT          900
GCTTTAAATTTTTTCTGTAATTTTGGAATGATGTATCTTTGTAGAGTTAATGATTTTGTACATTTGCACATGTAATCATCATACCCATTT          990
TCATTACTTTGATATAAGGTGCTAAACAAAAAAAGCTCTAGGTTCTTCAGCACATTTCCCCCAAAACAAATAAAATTGAGGGCATGTTG         1080
CATATTGTTGAATTGTATTGCGGTGGTATCAACCTGGGGGGAGGAGGGGCTGGCACTGAGATTTTTTTTCAAGATTGTAATGTGATTGA         1170
AGTTTTCAACACATCAACTCACATATGTTCAAAACCAAAATAATACCTTCATTATCAAACTGGTTACCATGCCTTACATAATGGAGTTAG         1260
TATTTGTGAGTAGAAAGACTTTAGGTAATGGAAATATAAATAAGAAAGAATGTTTAACATAATATGCTAAAAATATTTTCATATTTAAAT         1350
AACATACGTAAAGGTGTGCTTTCTGTGTTTTATATTATCTTGCAAATCCTTTTGCCCTTTAAAAAGCTGAAAATCTTGCCATCTGACTTA         1440
CTAGTCATTTTAGTGTTATAAATGGCATTTTGTACAAAATAGTCTATTCAGTTCGTTCATTCATTTAACACACATTGATTGAGTGCCTGC         1530
TGGGTACAAGGGATTCAATTTATGCCTATTGATATCTGCGGACCAAGATACCCATTTAGTGAAATACTTTTTTCCCTGAAATCTGTTAGA         1620
AAAGACTTTGAAATACTTCAGTGCAAAGTGTGTGTGTGTGAAGTTTAGTTATATCTTCATCTTCAGATGAAGTTTTAAAGCACTTTGTAG         1710
TTCTCTATTGCCAACAATTTAATGTTTATGTGTTGCCAATTCTTGCAACCACTGCCCTACCAAACCTGTGGGTTGCAAATCAGAACTAAA         1800
ATTCTAAGCACGTTTCAAAGATGAACACTTTTGTTAAGACCCCTATTGCCTCTTCTTCATGCTCATTTTTTACTTTTTTTAAAAGGTACT         1890
TTTCTCATCACATTGTAGAGAGGTCTGCATTCTCATTGGAAATGTCTGTTTAGCTTTATAAAACAAACACTTTGCTGAAATAGGAAAATG         1980
AGCCTTATTGACAATTAAGTGCTTCTTGCAGCAGGTGGTCAAAGAAAAGCATGACTAATACGACCTATTAGAGTAATCTACATCTGGACC         2070
ATTCCTTAAGTTTTTCCTCACCGACAGTACCATCATGCCTTGAGTGTTCTTTTCTCCCAAGTGCTATTCCTTAAACACGAGAGTTTACCA         2160
GTTGCCTAATAATGCAATAAAAAATGCTTTGAGATAGCTAACTGCCCATAAAACAAACTCAAATTGCTTATAAAGTTTCTTCCCATGTTC         2250
CCATTTGATGAAAAGTCTTACATCACATATAACTGGGAAGCAGGGGTCCCTCCTCAATTTTCAGACATTTTGAAAGGATGACAGTTCTGT         2340
TTGTTAGATGAGTAAACCTCTATATTCATAAGTTCTAAAATCCTTCATTATGAGGGATTCAAAGTATTTATAAAAACACTGCCCTCTAAA         2430
AATTTCCTCAGATCTGAAGTATGGTCTTGGTCCTGAATATACAGTGTTATCCTATGTTTAAAAGGGTGATCCAGACATGAGCGCAACTA         2520
GTTGGTGCATAAGAAGGCCCCACTTGGCTATTTCATATCTACCTACAATTGACCAAAAAAAATTTTTAGGCCAGCAATTATTATTTAGC         2610
TTCGCTCTTTCTAGTGCAAGAAACTGCAGGCTGGATCAGTAGTTCAACAGCTAAACAGTCATAAAATAGTCATTGTGCATGTTAAATTTC         2700
TTTCAATGCTTTCAAAGATAAATTCCAATTTCTATTTACTTATTCATTGTGACAGTATTACTAAACAGGTAAGGATGGGAATATTTTGTT         2790
ATACTGTGTATAGTGAATGTATTGTACTGTGTCTGTGAAAACTGTGCTTTAAATTATATTTTCATATGTTTTGTTGGGGACAGAGCACAT         2880
TAAGTCTGAAAGCAACGAGGTTTGTTTTAGAACTGAAGGCAATTTAATCAAAATTCCTGTCAAGAAAAGCTGCTTATAAATGTAAATGA         2970
AATCACATTTAAAATAAACTGCCTCTGACCCAAAAATAAA                                                          3010
```

FIG. 1

```
CTCTGAGGAGACACTTTTTTTTCCTCCCTCCTTCCCTCCTCTCCTCCTCCCTTCCCTTCCCCTCTCCTCCCCTCTCTCCTCCTTCCCCC     90
CTCGGTCCGCCGGAGCCTGCTGGGGCGAGCGGTTGGTATTGCAGGCGCTTGCTCTCCGGGGCCGCCCGGCGGGTAGCTGGCGGGGGAGG     180
AGGCAGGAACCGCGATGGCGCCTCAGAAGCACGGCGGTGGGGGAGGGGGCGGCTCGGGGCCCAGCGCGGGGTCCGGGGGAGGCGGCTTCG    270
                M  A  P  Q  K  H  G  G  G  G  G  G  S  G  P  S  A  G  S  G  G  G  F  G
GGGGTTCGGCGGCGGTGGCGGCGGCGACGGCTTCGGGCGGCAAATCCGGCGGCGGGAGCTGTGGAGGGGGTGGCAGTTACTCGGCCTCCT    360
     G  S  A  A  V  A  A  A  T  A  S  G  G  K  S  G  G  G  S  C  G  G  G  G  S  Y  S  A  S  S
CCTCCTCCTCCGCGGCGGCAGCGGCGGGGGCTGCGGTGTTACCGGTGAAGAAGCCGAAAATGGAGCACGTCCAGGCTGACCACGAGCTTT    450
     S  S  S  A  A  A  A  A  G  A  A  V  L  P  V  K  K  P  K  M  E  H  V  Q  A  D  H  E  L  F
TCCTCCAGGCCTTTGAGAAGCCAACACAGATCTATAGATTTCTTCGAACTCGGAATCTCATAGCACCAATATTTTTGCACAGAACTCTTA    540
     L  Q  A  F  E  K  P  T  Q  I  Y  R  F  L  R  T  R  N  L  I  A  P  I  F  L  H  R  T  L  T
CTTACATGTCTCATCGAAACTCCAGAACAAACATCAAAGGAAAACATTTAAAGTTGATGATATGTTATCAAAAGTAGAGAAAATGAAAG     630
     Y  M  S  H  R  N  S  R  T  N  I  K  R  K  T  F  K  V  D  D  M  L  S  K  V  E  K  M  K  G
GAGAGCAAGAATCTCATAGCTTGTCAGCTCATTTGCAGCTTACGTTTACTGGTTTCTTCCACAAAAATGATAAGCCATCACCAAACTCAG    720
     E  Q  E  S  H  S  L  S  A  H  L  Q  L  T  F  T  G  F  F  H  K  N  D  K  P  S  P  N  S  E
AAAATGAACAAAATTCTGTTACCCTGGAAGTCCTGCTTGTGAAAGTTTGCCACAAAAAAAGAAAGGATGTAAGTTGTCCAATAAGGCAAG    810
     N  E  Q  N  S  V  T  L  E  V  L  L  V  K  V  C  H  K  K  R  K  D  V  S  C  P  I  R  Q  V
TTCCCACAGGTAAAAAGCAGGTGCCTTTGATTCCTGACCTCAATCAAACAAAACCCGGAAATTTCCCGTCCCTTGCAGTTTCCAGTAATG    900
     P  T  G  K  K  Q  V  P  L  I  P  D  L  N  Q  T  K  P  G  N  F  P  S  L  A  V  S  S  N  E
AATTTGAACCTAGTAACAGCCATATGGTGAAGTCTTACTCGTTGCTATTTAGAGTGACTCGTCCAGGAAGAAGAGAGTTTAATGGAATGA    990
     F  E  P  S  N  S  H  M  V  K  S  Y  S  L  L  F  R  V  T  R  P  G  R  R  E  F  N  G  M  I
TTAATGGAGAAACCAATGAAAATATTGATGTCAATGAAGAGCTTCCAGCCAGAAGAAAACGAAATCGTGAGGATGGGGAAAAGACATTTG    1080
     N  G  E  T  N  E  N  I  D  V  N  E  E  L  P  A  R  R  K  R  N  R  E  D  G  E  K  T  F  V
TTGCACAAATGACAGTATTTGATAAAAACAGGCGCTTACAGCTTTTAGATGGGGAATATGAAGTAGCCATGCAGGAAATGGAAGAATGTC    1170
     A  Q  M  T  V  F  D  K  N  R  R  L  Q  L  L  D  G  E  Y  E  V  A  M  Q  E  M  E  E  C  P
CAATAAGCAAGAAAAGAGCAACATGGGAGACTATTCTTGATGGGAAGAGGCTGCCTCCATTCGAAACATTTTCTCAGGGACCTACGTTGC    1260
     I  S  K  K  R  A  T  W  E  T  I  L  D  G  K  R  L  P  P  F  E  T  F  S  Q  G  P  T  L  Q
AGTTCACTCTTCGTTGGACAGGAGAGACCAATGATAAATCTACGGCTCCTATTGCCAAACCTCTTGCCACTAGAAATTCAGAGAGTCTCC    1350
     F  T  L  R  W  T  G  E  T  N  D  K  S  T  A  P  I  A  K  P  L  A  T  R  N  S  E  S  L  H
ATCAGGAAAACAAGCCTGGTTCAGTTAAACCTACTCAAACTATTGCTGTTAAAGAATCATTGACTACAGATCTACAAACAAGAAAAGAAA    1440
     Q  E  N  K  P  G  S  V  K  P  T  Q  T  I  A  V  K  E  S  L  T  T  D  L  Q  T  R  K  E  K
AGGATACTCCAAATGAAAACCGACAAAAATTAAGAATATTTTATCAGTTTCTCTATAACAACAATACAAGGCAACAAACTGAAGCAAGAG    1530
     D  T  P  N  E  N  R  Q  K  L  R  I  F  Y  Q  F  L  Y  N  N  N  T  R  Q  Q  T  E  A  R  D
ATGACCTGCATTGCCCTTGGTGTACTCTGAACTGCCGCAAACTTTATAGTTTACTCAAGCATCTTAAACTCTGCCATAGCAGATTTATCT    1620
     D │ L  H  C  P  W  C  T  L  N  C  R  K  L  Y  S  L  L  K  H  L  K  L  C  H │ S  R  F  I  F
TCAACTATGTTTATCATCCAAAAGGTGCTAGGATAGATGTTTCTATCAATGAGTGTTATGATGGCTCCTATGCAGAAATCCTCAGGATA     1710
     N  Y  V  V  Y  H  P  K  G  A  R  I  D  V  S  I  N  E  C  Y  D  G  S  Y  A  G  N  P  Q  D  I
TTCATCGCCAACCTGGATTTGCTTTTAGTCGCAACGGACCAGTTAAGAGAACACCTATCACACATATTCTTGTGTCAGGCCAAAACGAA     1800
     H  R  Q  P  G  F  A  F  S  R  N  G  P  V  K  R  T  P  I  T  H  I  L  V  C  R  P  K  R  T
CAAAAGCAAGCATGTCTGAATTTCTTGAATCTGAAGATGGGGAAGTAGAACAGCAAAGAACATATAGTAGTGGCCACAATCGTCTGTATT    1890
     K  A  S  M  S  E  F  L  E  S  E  D  G  E  V  E  Q  Q  R  T  Y  S  S  G  H  N  R  L  Y  F
TCCATAGTGATACCTGCTTACCTCTCCGTCCACAAGAAATGGAAGTAGATAGTGAAGATGAAAAGGATCCTGAATGGCTAAGAGAAAAAA    1980
     H  S  D  T  C  L  P  L  R  P  Q  E  M  E  V  D  S  E  D  E  K  D  P  E  W  L  R  E  K  T
CCATTACACAAATTGAAGAGTTTTCTGATGTTAATGAAGGAGAGAAAGAAGTGATGAAACTCTGGAATCTCCATGTCATGAAGCATGGGT    2070
     I  T  Q  I  E  E  F  S  D  V  N  E  G  E  K  E  V  M  K  L  W  N  L  H  V  M  K  H  G  F
TTATTGCTGACAATCAAATGAATCATGCCTGTATGCTGTTTGTAGAAAATTATGGACAGAAAATAATTAAGAAGAATTTATGTCGAAACT    2160
     I  A  D  N  Q  M  N  H  A  C  M  L  F  V  E  N  Y  G  Q  K  I  I  K  K  N  L  C  R  N  F
TCATGCTTCATCTAGTCAGCATGCATGACTTTAATCTTATTAGCATAATGTCAATAGATAAAGCTGTTACCAAGCTCCGTGAAATGCAGC    2250
     M  L  H  L  V  S  M  H  D  F  N  L  I  S  I  M  S  I  D  K  A  V  T  K  L  R  E  M  Q  Q
```

FIG. 2A

```
AAAAATTAGAAAGGGGAATCTGCTTCCCCTGCAAACGAAGAAGAAATAACTGAAGAACAAATGGGACAGCAAATGATTTAGTGAAATTA    2340
  K  L  E  K  G  E  S  A  S  P  A  N  E  E  I  T  E  E  Q  N  G  T  A  N  G  P  S  E  I  N
ACTCAAAAGAGAAAGCTTTGGAAACAGATAGTGTCTCAGGGGTTCAAAACAGACAAAAACTCTGAAAAGCTCTAACCCCAT             2430
  S  K  E  K  A  L  E  T  D  S  V  S  G  V  S  K  Q  S  K  K  Q  K  L
GTTATGGACAAACACTGAAATTACATTTAGGAATTCATCCTCTAAGAATTATGTTTTGTTTTAATCATATGTTCCAAACAGGACT         2520
GTTAGATGAGTAAAATGATTCAACAAGGATATTGTATCAGGGTTCTACTTCATTATGCAGCATTACATGTATATCACTTTTAT           2610
TGATGTCATTAAAACATTCTGTACTTTAAGCATGAAAAGCAATATTCAAGTATTTTAAACTCAACAAATGTCATCAAATATGTTGAA       2700
TTGATCTAGAAATTTATTCATATATAATCAGAATTTTTTGCATTTATGAACGGCTGTTTTTCTACTTTGTTAATTGTGAGACATTTCT      2790
TGGGGAGGGAAAATTGGAATGGTTCCCTTTTTAGAAATTGAAGTGGTCTTCATATGTCAACTACAGAAAAGGAAAAAATAGAAATTGA      2880
AGGATTTTTATGAAATTATATTGCAGTCAAACTTTGATCCTTGTTTTGAAATCATTTGTCAATTCGGAATGAAAAT                  2970
TATAATGTAATTTACATTACATAAGTTCTTTTACAATTAAAAATACAGACCATTGTTTCATCTTCATGTGGATAATTTAGTGCATTC      3060
TCACATTGTTGACAGTGAAATGCTATGTGGTTTATAAGATTACAGACCATTGTTTCTTTTCATTGTGATAATTCACGGAAAATTAAGCT    3150
GTATGTTTTTTTTTTGTTGAACATTTGTTTCTTTTAATTAGATAATCACACGGAAGTTCTTAAAAGTCATAT                      3240
CTTAAATTAGGATTGCAAACCAAGAGAACGCATTTGAGATTTTAAGATGTCACTTATAAGGGGAGAATATCCAATAGAGATAAGCTCAAC   3330
CAGAAAAACTGTTATGCCTTTATTGTTTGCAAGGATGTCTTGTAATGTGTTCATGAAGTTCAGTTGAGTAACATCACCTCAATTTTTAAATTTTAAAATTTATAAAATGTAAATACTGATTTG 3420
AATCATTTGAGCAATTGCCCTGTGTATATGTTTCACGCACATATTGCAGTTGGATTTCTCCAACAGAAGTGGATTCACTAC            3510
TGGCACATTAACAAGCACCAATAGGTTTTATTCCAACTCCGAGCACTGTGGTTGAGTAAATACAGTATTTTTAAATTTCATTCCACCACCAT 3600
ATATTGCATTTCATATTCTTGTTTTATTATAAGGATCAATGCTACTTAATAAGCTTTATTTTAAATTTATAAATGTAAATACTGATTTG    3690
CAGATGCAGTTCCCTATTTGTTTAATGTGTTAACTGTGAGAGGAGAGGGAAGAGAGGGGAGCTATTTAACGAATAGTGTGGATGGATATTA  3780
ACTGGTCTTTAAGATGTGTTAACTGTTGAGCGTTCATTACAGATTCCTTGATTGTCATCGGATGTAAGCTCTCCAAATGATGAGTTCT     3870
TTTTGTGTTTAAAAAAAATAGGAAAGAGAGGAAACTGCAGCTTCGAGCGTTTATCTCGGGCTTTATGTCATTGCTTATGCAGTTATGCTTA  3960
AGTAAACTCTGATTTTGCCTCTGGATAGTAGATGTAGGGAGATGTGGTGATTCCCACCCAAAAAGTGCACTATGGTGCACTATGTAAAAAA  4050
AAAAAAAGATTATTAGGGAGAAGTAGTGGATCTCGAGCGTTAGTAGCGTGATCTCGGGGCTTATGTCATTGTCTGAGAGGAGCTCT       4140
AGGCTAGCATTGTTTGCACAAAAGTTGGTGATTCCCAAAATAGTAATAATTAACTCTGTGAGTAACAGATTTGAAGAATCATCGT       4230
AAAGCTGAAAAATCCCTTGTTTCTATTTATAAAAAGTGCTTTTCTATATGTACCCTTAAAATGTACCCTTAAAAGAAGAATCCTGTAA     4320
GATGATAAGCATTTGAATGGTACAGTAGATGTAAAAATTCAGTTTTACATTGTTTTTACATTAAATGTTTATTTGAAATC             4410
AAATGATTTGTACATAAAGTTCAATATAT                                                                4441
```

FIG. 2B

```
CCCGCCCGGCGCTCGCAGAGCCGACACCAGGGGGGCTCTCGATGTAGCACCATGACAGGCATCGCCGCCGCCTCCTTCTTCTCCAATACC        90
                                                      M  T  G  I  A  A  A  S  F  F  S  N  T
TGCCGATTCGGGGGCTGCGGACTCCACTTCCCCACCCTGGCCGACCTCATCGAGCACATCGAGGACAACCACATCGATACAGATCCACGG      180
 C  R  F  G  G  C  G  L  H  F  P  T  L  A  D  L  I  E  H  I  E  D  N  H  I  D  T  D  P  R-
GTTTTAGAAAAACAAGAATTACAGCAGCCAACCTATGTTGCCCTGAGTTACATAAATAGATTCATGACAGATGCTGCCCGCCGAGAGCAG      270
 V  L  E  K  Q  E  L  Q  Q  P  T  Y  V  A  L  S  Y  I  N  R  F  M  T  D  A  A  R  R  E  Q
GAGTCCCTAAAGAAGAAGATTCAGCCGAAGCTCTCGCTGACTCTGTCCAGCTCAGTGTCTCGAGGGAATGTGTCCACTCCCCCACGCCAC      360
 E  S  L  K  K  K  I  Q  P  K  L  S  L  T  L  S  S  S  V  S  R  G  N  V  S  T  P  P  R  H
                                                                           JAZF1 ←→ JJAZ1
AGCAGTGGAAGCCTTACTCCCCCCGTGACCCCACCCATCACCCCCTCCTCTTCATTCCGCAGCAGCACTCCGACAGAGCCAACACAGATC      450
 S  S  G  S  L  T  P  P  V  T  P  P  I  T  P  S  S  S  F  R  S  S  T  P  T  E  P  T  Q  I
TATAGATTTCTTCGAACTCGGAATCTCATAGCACCAATATTTTTGCACAGAACTCTTACTTACATGTCTCATCGAAACTCCAGAACAAAC      540
 Y  R  F  L  R  T  R  N  L  I  A  P  I  F  L  H  R  T  L  T  Y  M  S  H  R  N  S  R  T  N
ATCAAAAGGAAAACATTTAAAGTTGATGATATGTTATCAAAAGTAGAGAAAATGAAAGGAGAGCAAGAATCTCATAGCTTGTCAGCTCAT      630
 I  K  R  K  T  F  K  V  D  D  M  L  S  K  V  E  K  M  K  G  E  Q  E  S  H  S  L  S  A  H
TTGCAGCTTACGTTTACTGGTTTCTTCCACAAAAATGATAAGCCATCACCAAACTCAGAAAATGAACAAAATTCTGTTACCCTGGAAGTC      720
 L  Q  L  T  F  T  G  F  F  H  K  N  D  K  P  S  P  N  S  E  N  E  Q  N  S  V  T  L  E  V
CTGCTTGTGAAAGTTTGCCACAAAAAAAGAAAGGATGTAAGTTGTCCAATAAGGCAAGTTCCCACAGGTAAAAAGCAGGTGCCTTTGATT      810
 L  L  V  K  V  C  H  K  K  R  K  D  V  S  C  P  I  R  Q  V  P  T  G  K  K  Q  V  P  L  I
CCTGACCTCAATCAAACAAAACCCGGAAATTTCCCGTCCCTTGCAGTTTCCAGTAATGAATTTGAACCTAGTAACAGCCATATGGTGAAG      900
 P  D  L  N  Q  T  K  P  G  N  F  P  S  L  A  V  S  S  N  E  F  E  P  S  N  S  H  M  V  K
TCTTACTCGTTGCTATTTAGAGTGACTCGTCCAGGAAGAAGAGAGTTTAATGGAATGATTAATGGAGAAACCAATGAAAATATTGATGTC      990
 S  Y  S  L  L  F  R  V  T  R  P  G  R  R  E  F  N  G  M  I  N  G  E  T  N  E  N  I  D  V
AATGAAGAGCTTCCAGCCAGAAGAAAACGAAATCGTGAGGATGGGGAAAAGACATTTGTTGCACAAATGACAGTATTTGATAAAAACAGG     1080
 N  E  E  L  P  A  R  R  K  R  N  R  E  D  G  E  K  T  F  V  A  Q  M  T  V  F  D  K  N  R
CGCTTACAGCTTTTAGATGGGGAATATGAAGTAGCCATGCAGGAAATGGAAGAATGTCCAATAAGCAAGAAAAGAGCAACATGGGAGACT     1170
 R  L  Q  L  L  D  G  E  Y  E  V  A  M  Q  E  M  E  E  C  P  I  S  K  K  R  A  T  W  E  T
ATTCTTGATGGGAAGAGGCTGCCTCCATTCGAAACATTTTCTCAGGGACCTACGTTGCAGTTCACTCTTCGTTGGACAGGAGAGACCAAT     1260
 I  L  D  G  K  R  L  P  P  F  E  T  F  S  Q  G  P  T  L  Q  F  T  L  R  W  T  G  E  T  N
GATAAATCTACGGCTCCTATTGCCAAACCTCTTGCCACTAGAAATTCAGAGAGTCTCCATCAGGAAAACAAGCCTGGTTCAGTTAAACCT     1350
 D  K  S  T  A  P  I  A  K  P  L  A  T  R  N  S  E  S  L  H  Q  E  N  K  P  G  S  V  K  P
ACTCAAACTATTGCTGTTAAAGAATCATTGACTACAGATCTACAAACAAGAAAAGAAAAGGATACTCCAAATGAAAACCGACAAAAATTA     1440
 T  Q  T  I  A  V  K  E  S  L  T  T  D  L  Q  T  R  K  E  K  D  T  P  N  E  N  R  Q  K  L
AGAATATTTTATCAGTTTCTCTATAACAACAATACAAGGCAACAAACTGAAGCAAGAGATGACCTGCATTGCCCTTGGTGTACTCTGAAC     1530
 R  I  F  Y  Q  F  L  Y  N  N  N  T  R  Q  Q  T  E  A  R  D  D  L  H  C  P  W  C  T  L  N
TGCCGCAAACTTTATAGTTTACTCAAGCATCTTAAACTCTGCCATAGCAGATTTATCTTCAACTATGTTTATCATCCAAAAGGTGCTAGG     1620
 C  R  K  L  Y  S  L  L  K  H  L  K  L  C  H  S  R  F  I  F  N  Y  V  Y  H  P  K  G  A  R
ATAGATGTTTCTATCAATGAGTGTTATGATGGCTCCTATGCAGGAAATCCTCAGGATATTCATCGCCAACCTGGATTTGCTTTTAGTCGC     1710
 I  D  V  S  I  N  E  C  Y  D  G  S  Y  A  G  N  P  Q  D  I  H  R  Q  P  G  F  A  F  S  R
AACGGACCAGTTAAGAGAACACCTATCACACATATTCTTGTGTGCAGGCCAAAACGAACAAAAGCAAGCATGTCTGAATTTCTTGAATCT     1800
 N  G  P  V  K  R  T  P  I  T  H  I  L  V  C  R  P  K  R  T  K  A  S  M  S  E  F  L  E  S
GAAGATGGGGAAGTAGAACAGCAAAGAACATATAGTAGTGGCCACAATCGTCTGTATTTCCATAGTGATACCTGCTTACCTCTCCGTCCA     1890
 E  D  G  E  V  E  Q  Q  R  T  Y  S  S  G  H  N  R  L  Y  F  H  S  D  T  C  L  P  L  R  P
CAAGAAATGGAAGTAGATAGTGAAGATGAAAAGGATCCTGAATGGCTAAGAGAAAAAACCATTACACAAATTGAAGAGTTTTCTGATGTT     1980
 Q  E  M  E  V  D  S  E  D  E  K  D  P  E  W  L  R  E  K  T  I  T  Q  I  E  E  F  S  D  V
AATGAAGGAGAAAAGAAGTGATGAAACTCTGGAATCTCCATGTCATGAAGCATGGGTTTATTGCTGACAATCAAATGAATCATGCCTGT     2070
 N  E  G  E  K  E  V  M  K  L  W  N  L  H  V  M  K  H  G  F  I  A  D  N  Q  M  N  H  A  C
ATGCTGTTTGTAGAAAATTATGGACAGAAAATAATTAAGAAGAATTTATGTCGAAACTTCATGCTTCATCTAGTCAGCATGCATGACTTT     2160
 M  L  F  V  E  N  Y  G  Q  K  I  I  K  K  N  L  C  R  N  F  M  L  H  L  V  S  M  H  D  F
```

FIG. 3A

```
AATCTTATTAGCATAATGTCAATAGATAAGCTGTTACCAAGCTCCGTGAAATGCAGCAAAATTAGAAAAGGGGAATCTGCTTCCCT    2250
 N  L  I  S  I  M  S  I  D  K  A  V  T  K  L  R  E  M  Q  Q  K  L  E  K  G  E  S  A  S  P

GCAAACGAAGAATAACTGAAGAACAAATGGGACAGCAAATGGATTTAGTGAATTAACTCAAAAGAGAAAGCTTTGAAACAGATAGT    2340
 A  N  E  E  I  T  E  E  Q  N  G  T  A  N  G  F  S  E  I  N  S  K  E  K  A  L  E  T  D  S

GTCTCAGGGGTTTCAAAACAGAGCAAAACAACAAACTCTGAAAAGCTCTAACCCATGTTATGGACAAACACTGAAATTACATTTAGG    2430
 V  S  G  V  S  K  Q  S  K  K  Q  K  L

GAATTCATCCTCTAAGAATTATGTTTTTGTTTTTAATCATATGTTCCAAACAGGCACTGTTAGATGAAGTAAATGATTTCAACAAGGATA    2520
TTTGTATCAGGGTTCTACTTCACTTCATTATGCAGCATTACATGTATATCTGTTATTGATGTCATTAAAACATTCTGTACTTTAAGCA    2610
TGAAAGCAATATATTCAAAGTATTTTAAACTCAACAAATGTCATCAAAATGTGAATTGATCTAGAAAATTATTCATATATAATCAG    2700
AATTTTTTGCATTTATGAACGGCTGTTTTCTACTTGTGTAAGTAGACATTTCTTTGGGGAGGAAAATTTATGAAATATATGCATTACTAT    2790
TAGAAATTGAAGTGGTCTTCATATGTCAACTACAGAAAGAAATGTGTCAATTGTCTTTTGAAATCATTTGTGAATGAAATTTATAATTTACATTACATAAGTTCCTT    2880
TTGCAGTCAAACTTTGATCCTTGTTTTTCATCTTATGCCTGTTTGAGAAGATATTAAATTTCACATTGTTGACAGTGAAATGCTATGTGT    2970
TTACAATTAAAAATAGACACTTCTTCATTGTTTTCTCATGTCAGTTAGTGCATTGCTCACCCGTATGTTTTTTTAACTTGAACATTTG    3060
TATAAGATTACAGACCATTTGTTCTTTTTTAATTAGATAGTCACTTAATGATAATCACACGGAAGTGTTCTTAAAAGCTGACTTACTACCTTAAAAGCTGACTTACTACC    3150
CTGTTTGTTTTCTTTGAGATTTAAGATGTCACTTATTGCAGTTGAGATGGGGAGAATATCCAACAAGCTGATTCACTACTCCTTAAAGCTGTATGCCAATAGTTTTAT    3240
AGGATGTCTTTCACGCCAGCACTGTGGTTGAGTAACATGAAGCTCCCAGTACAGAGTATTTTAATTTTAATTCAGTTTCATATCTTATCCTTATTATAAGCACCAATAGTTTTAT    3330
TGTGTTTTCACGCCAGCACTGTGGTTGAGTAACATAATATTTTTTAATTCAGTTCATATTCCTTAATTTCTTATTATAAAG    3420
TCCAACTCCGAGCACTGCTGTAAATACAGTATTTTAATTTCATTCCACCACCATCAGATGCAGTTCCCTATTTGTTAATGAAGG    3510
GATCAATGCTGCTGTAAATACAGTATTTCTTCAGAAATTATATAATAAATTATATAATCCAGTATTGTCTTAAGATGTGTAACTGGTGAGGC    3600
GATATAAGCTTCTAAGTGTTCTCAGAAATTATATAAATGTAAATACAGTATATAAATGCAGTTAAAAAATAGGAAAGAGGG    3690
TATTAACGAATAGTGTGATGTCATCCAGTATTGTCATCCAGTATTGTCTAGTACAGATTTTCATTGATTTTGTAAAAAAAATAGGAAAGAGGG    3780
AAACTGCAGCTTCATTACAGATTCCTGATTGGTAAGCTCTCCAAATGATGAGTCTAGTAAACTCTGATTTTTGCCTCTGGATAGTAG    3870
ATCTCGAGCGTTATCTCGGGCTTTATGTCATTTCTTAAGCAGTTATGCTAAGCAGTTATGCTCTTAAAGCAGTTATAAAAAAGATTATTTTAGGGGAGATGTAG    3960
GTGTAGAATTATTGCTTATGTCATTTCTTAAGCAGTTATGCTTAAAGCAGTTAAACTTTTTATGTCATCGTAAAGAAGGCTAGCATTGTTTGCACAAAGTTGGTGA    4050
TTCCCACCCAAATAGTAATAAATTACTTCTGTTGATAACAGATTTGAAGAAATCCTTGTCTGTAAGATGATAAGCATTGTAAAGCATTTGAATGATGAGTAG    4140
TAAAAAAGTGCTTTCTATAGTAATAAATTACTTCTGTTGATAACAGATTTGAAGAAATCCTTGTCTGTAAGATGATAAGCATTGAATGATGAGTAGTAGATG    4230
TAAAAAATCAGTTTAAAGAACATTTGTTTTTACATTAAATGTTTATTGAAATCAAATGATTGTTGTACATAAAGTTCAATATAT    4320
                                                                                       4409
```

FIG. 3B

Structure of JAZF1
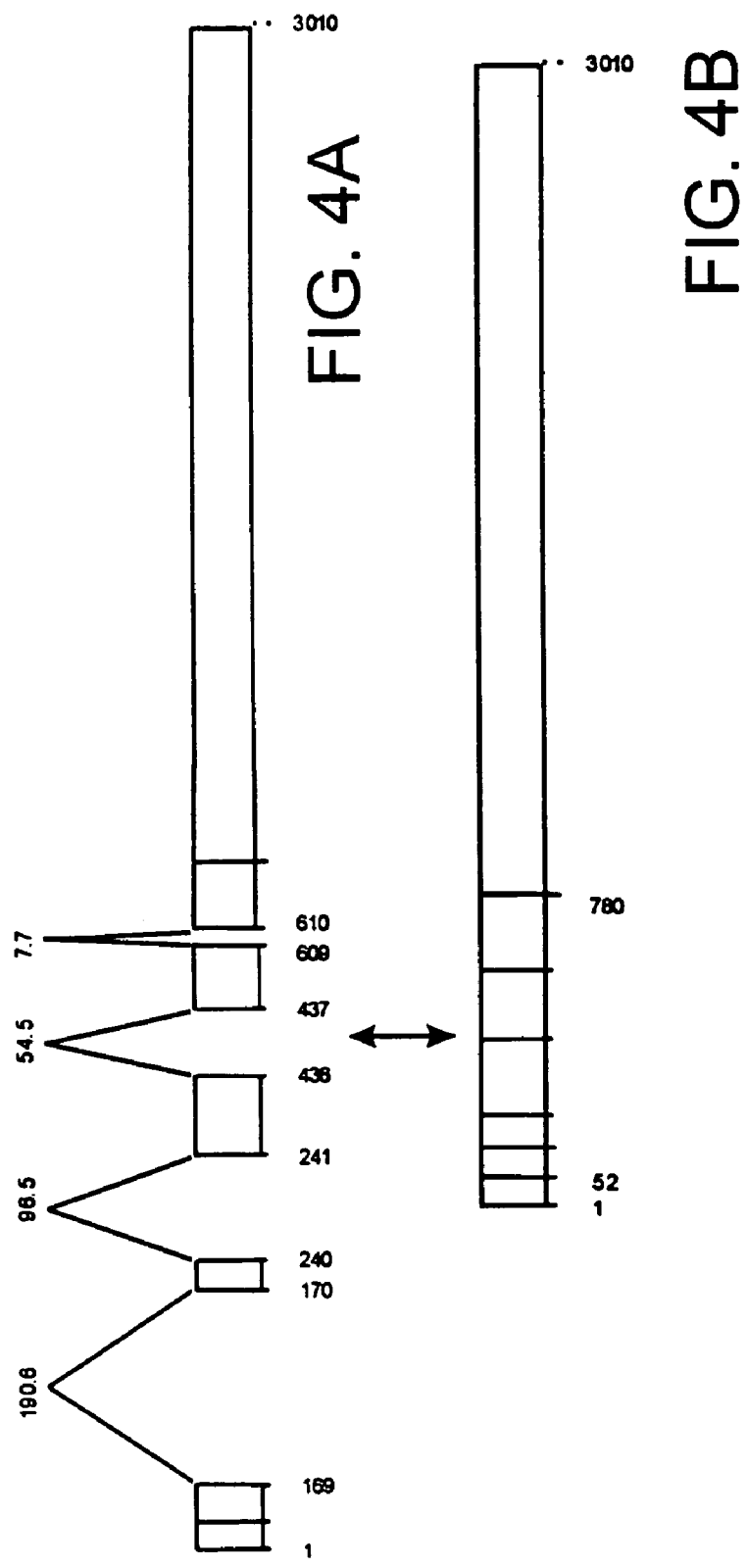

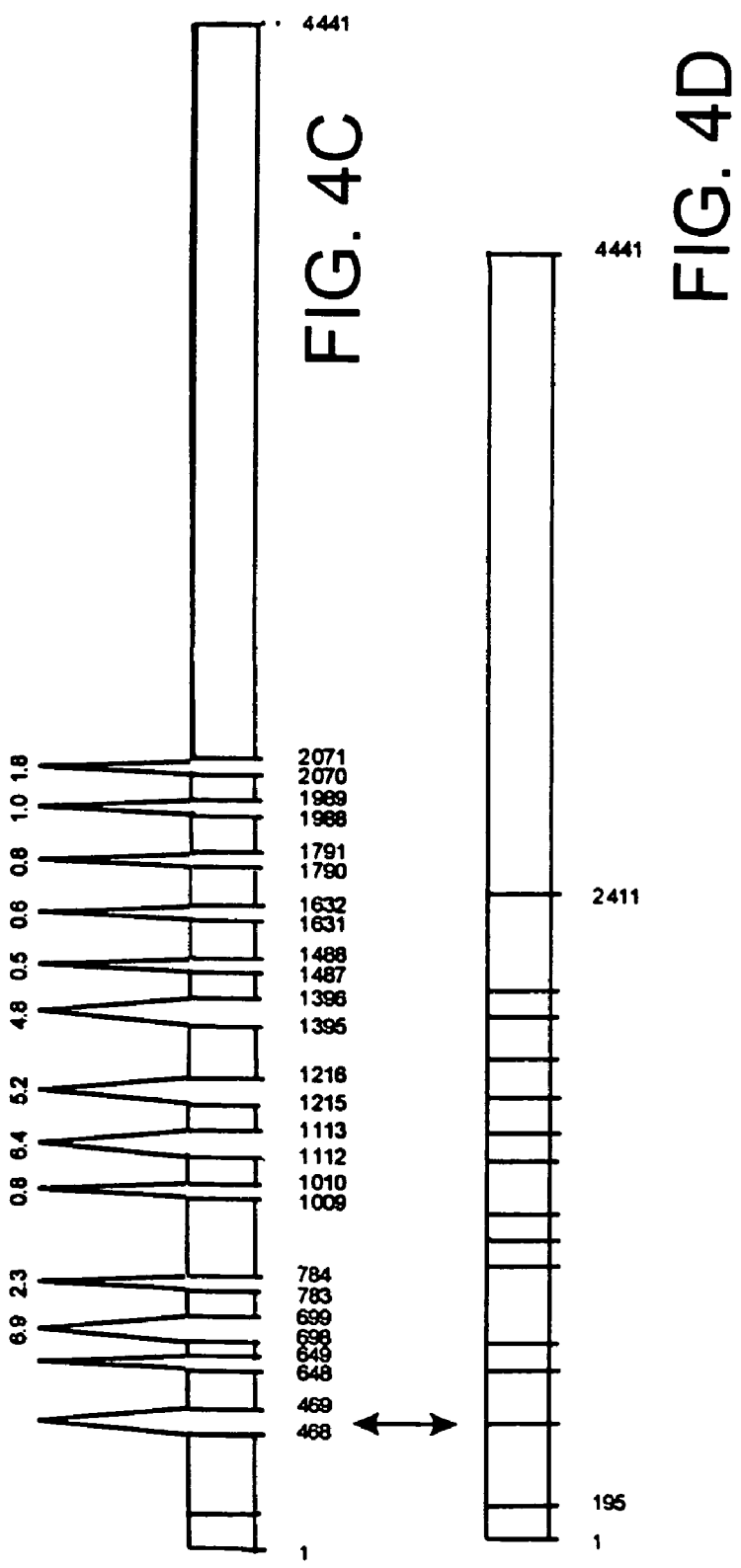

US 7,098,311 B2

FUSION OF JAZF1 AND JJAZ1 GENES IN ENDOMETRIAL STROMAL TUMORS

CROSS-REFERENCE TO RELATED APPLICATIONS

This application claims priority from U.S. Provisional Application Ser. No. 60/209,093, filed on Jun. 2, 2000, and is hereby incorporated by reference in its entirety.

BACKGROUND OF THE INVENTION

Endometrial stromal tumors of the uterus encompass a spectrum of neoplasms that can present a number of diagnostic challenges. Difficulties in the diagnosis of these tumors arise from controversies in the classification of these tumors, the occasional confusion of endometrial stromal tumors with non-stromal sarcomas, and the uncertain relationships of different tumor types within this group of neoplasms.

Stromal nodules fall at the benign end of spectrum containing these tumors. These neoplasms are circumscribed tumors composed of cells resembling those of normal mesenchymal tissue that lies between the epithelial lining and the underlying myometrium of the normal uterus, as this tissue appears during the proliferative phase of the menstrual cycle. Endometrial stromal sarcomas (ESSs) are malignant neoplasms that have traditionally been classified into low grade and high grade types. Histologically, low grade ESSs are identical to stromal nodules except for infiltration of the myometrium or vascular invasion. Accurate discrimination of stromal sarcoma from low grade ESS may therefore require extensive examination of the uterus that can only be accomplished after hysterectomy. Furthermore, the propensity of low grade ESSs to invade vessels sometimes leads to misdiagnoses as endolymphatic leiomyomatosis, a neoplasm of smooth muscle.

High grade ESSs were formerly separated from low grade ESSs by an increased frequency of mitoses (>ten per high power microscopic field) and were generally assumed to have a worse prognosis. More recently, it has been argued that the number of mitoses within ESSs is largely irrelevant to outcome, which is said to be almost exclusively a function of stage at diagnosis. Experts holding to this view place all ESSs in the same diagnostic category regardless of mitotic activity and use the term undifferentiated uterine sarcoma (UUS) for those stromal tumors that depart significantly in histologic appearance from normal endometrial stroma. Whether UUSs evolve from ESSs is unknown. UUSs are more likely to metastasize than are ESSs, but metastatic lesions from endometrial stromal tumors of any histologic subtype can cause diagnostic problems, especially if they are detected some time after removal of the uterus for benign disease.

Diagnosis and classification of endometrial stromal tumors has until now been based primarily on histologic criteria. In recent years, specific genetic alterations identified in different types of human tumors have become useful markers that have improved the accuracy of tumor diagnosis and classification. Additionally, the discovery of genetic abnormalities in tumors has also led to insights into the basic biology of normal and neoplastic tissues, and increasingly to rational forms of cancer therapy (reference Her 2/neu, p53 virus, and bcr-abl therapy).

SUMMARY OF THE INVENTION

The present invention is based, in part, on the discovery that the chromosomal translocation, t(7;17)(p15; q21), which is associated with low grade endometrial stromal tumors, is the result of a gene fusion between two novel genes, "juxtaposed with another zinc finger", referred to herein as "jAZF1", and "joined with JAZF1", referred to herein as "jjAZ1". More particularly, it was discovered that the 5' end of jAZF1 on chromosome 7 is joined to the 3' end of jjAZ1 on chromosome 17 resulting in a jAZF1/jjAZ1 gene fusion. The jAZF1/jjAZ1 gene fusion and jAZF1/jjAZ1 protein fusion are present in endometrial stromal tumors but not in normal endometrium, and are therefore useful to detect the presence of endometrial stromal tumors, to make treatment decisions, and to predict the risk of enodmetrial stromal tumor in an individual.

The nucleotide sequence of a cDNA encoding jAZF1 is shown in SEQ ID NO:1, and the amino acid sequence of a jAZF1 polypeptide is shown in SEQ ID NO:2. In addition, the nucleotide sequence of the jAZF1 coding region is depicted in SEQ ID NO:3 (FIG. 1). The nucleotide sequence of a cDNA encoding jjAZ1 is shown in SEQ ID NO:4, and the amino acid sequence of a jjAZ1 polypeptide is shown in SEQ ID NO:5. In addition, the nucleotide sequence of the jjAZ1 coding region is depicted in SEQ ID NO:6 (FIG. 2). The nucleotide sequence of the cDNA encoding jAZF1/jjAZ1 is shown in SEQ ID NO:7, and the amino acid sequence of the jAZF1/jjAZ1 polypeptide is shown in SEQ ID NO:8. In addition, the nucleotide sequence of the jAZF1/jjAZ1 coding region is depicted in SEQ ID NO:9 (FIG. 3).

Accordingly, in one aspect, the invention features a nucleic acid molecule which encodes a jAZF1, jjAZ1 or jAZF1/jjAZ1 protein or polypeptide, e.g., a biologically active portion of the jAZF1, jjAZ1 or jAZF1/jjAZ1 protein. In a preferred embodiment the isolated nucleic acid molecule encodes a polypeptide having the amino acid sequence of SEQ ID NO:2, SEQ ID NO:5 or SEQ ID NO:8. In other embodiments, the invention provides isolated jAZF1, jjAZ1 or jAZF1/jjAZ1 nucleic acid molecules having the nucleotide sequence shown in SEQ ID NO:1, SEQ ID NO:3, SEQ ID NO:4, SEQ ID NO:6, SEQ ID NO:7, or SEQ ID NO:9, respectively. In still other embodiment, the invention provides nucleic acid molecules that are substantially identical (e.g., naturally occurring allelic variants) to the nucleotide sequence shown in SEQ ID NO:7 or SEQ ID NO:9. In other embodiments, the invention provides a nucleic acid molecule which hybridizes under stringent hybridization conditions to a nucleic acid molecule comprising the nucleotide sequence of SEQ ID NO:7 or SEQ ID NO:9, wherein the nucleic acid encodes a full length jAZF1/jjAZ1 protein or an active fragment thereof.

In a related aspect, the invention further provides nucleic acid constructs which include a jAZF1, jjAZ1 or jAZF1/jjAZ1 nucleic acid molecule described herein. In certain embodiments, the nucleic acid molecules of the invention are operatively linked to native or heterologous regulatory sequences. Also included, are vectors and host cells containing the jAZF1, jjAZ1 or jAZF1/jjAZ1 nucleic acid molecules of the invention e.g., vectors and host cells suitable for producing JAZF1, jjAZ1 or jAZF1/jjAZ1 nucleic acid molecules and polypeptides.

In another related aspect, the invention provides nucleic acid fragments suitable as primers or hybridization probes for the detection of jAZF1/jjAZ1-encoding nucleic acids.

In still another related aspect, isolated nucleic acid molecules that are antisense to a jAZF1/jjAZ1 encoding nucleic acid molecule are provided.

In another aspect, the invention features, jAZF1, jjAZ1 or jAZF1/jjAZ1 polypeptides, and biologically active or antigenic fragments thereof that are useful, e.g., as reagents or targets in assays applicable to treatment and diagnosis of jAZF1, jjAZ1 or jAZF1/jjAZ1 mediated or related disorders. In another embodiment, the invention provides jAZF1, jjAZ1or jAZF1/jjAZ1 polypeptides having a jAZF1, jjAZ1 or jAZF1/jjAZ1 activity. Preferred polypeptides are jAZF1, jjAZ1 or jAZF1/jjAZ1 proteins including at least one zinc finger domain, and, preferably, having a jAZF1, jjAZ1 or jAZF1/jjAZ1 activity, e.g., a jAZF1, jjAZ1 or jAZF1/jjAZ1 activity as described herein.

In other embodiments, the invention provides jAZF1, jjAZ1 or jAZF1/jjAZ1 polypeptides, e.g., a jAZF1, jjAZ1 or jAZF1/jjAZ1 polypeptide having the amino acid sequence shown in SEQ ID NO:2, SEQ ID NO:5 or SEQ ID NO:8; an amino acid sequence that is substantially identical to the amino acid sequence shown in SEQ ID NO:2, SEQ ID NO:5 or SEQ ID NO:8; or an amino acid sequence encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:4, SEQ ID NO:6, SEQ ID NO:7, or SEQ ID NO:9, wherein the nucleic acid encodes a full length jAZF1, jjAZ1 or jAZF1/jjAZ1 protein or an active fragment thereof.

In a related aspect, the invention further provides nucleic acid constructs, which include a jAZF1, jjAZ1 or jAZF1/jjAZ1 nucleic acid molecule described herein.

In a related aspect, the invention provides jAZF1, jjAZ1 or jAZF1/jjAZ1 polypeptides or fragments operatively linked to non-jAZF1, jjAZ1 or jAZF1/jjAZ1 polypeptides to form fusion proteins.

In another aspect, the invention features antibodies and antigen-binding fragments thereof, that react with, or more preferably specifically bind jAZF1, jjAZ1 or jAZF1/jjAZ1 polypeptides.

In another aspect, the invention provides methods of screening for compounds that modulate the expression or activity of the jAZF1, jjAZ1 or jAZF1/jjAZ1 polypeptides or nucleic acids. Initial homology evaluations indicate that JJAZ is homologous to a Drosophila Zeste suppressor gene called Suppressor of Zeste 12, available in the Drosophila Genome database. Generally, Zeste suppressors work as transcriptional repressors of homeotic genes. The homologs of these genes in humans are the homeobox genes, which are important in development and often in the proliferation of developing tissues. Two homeobox genes, HOXa10 and 11, figure importantly in endometrial development and proliferation during the menstrual cycle. When various mouse embryo tissues are evaluated with antibodies against JJAZ protein, a reaction occurs substantially only with primitive gonad tissue. Without binding ourselves to any specific theory, we conclude that JJAZ product inhibits the homeobox proteins involved in proliferation of the endometrial stroma during development, menstrual cycling, and implantation of the embryo in early pregnancy. Tumors arise from the fusion because the JJAZ product is knocked out or reduced in amount, thereby leaving the expression of the critical homeobox genes unopposed. Accordingly, the invention further features reagents and methods used to identify compounds that inhibit normal endometrial function by adding or reducing JJAZ activity pharmacologically. Controlling JJAZ activity can be used, for example, to promote or decrease fertility or pregnancy, in addition to the uses described above concerning endometrial stromal tumors.

In still another aspect, the invention provides a process for modulating jAZF1, jjAZ1 or jAZF1/jjAZ1 polypeptide or nucleic acid expression or activity, e.g. using the screened compounds. In certain embodiments, the methods involve treatment of conditions related to aberrant activity or expression of the jAZF1, jjAZ1 or jAZF1/jjAZ1 polypeptides or nucleic acids.

The invention also provides assays for determining the activity of or the presence or absence of jAZF1, jjAZ1 or jAZF1/jjAZ1 polypeptides or nucleic acid molecules in a biological sample, including for disease diagnosis. For example, the presence of a jAZF1/jjAZ1 polypeptide or nucleic acid molecule in a biological sample is indicative of a endometrial stromal tumor. This aspect is particularly useful (usually in conjunction with other diagnostic techniques) for discriminating between stromal tumors and tumors of other types that may be difficult to differentiate from certain types of stromal tumors. It can also be useful to determine that a secondary tumor site originated from a stromal tumor.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4kb, 3kb, 2kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in *Current Protocols in Molecular Biology*, John Wiley & Sons, N.Y. (1989), 6.3.1–6.3.6. Aqueous and nonaqueous methods are described in that reference and either can be used. A preferred, example of stringent hybridization conditions are hybridization in 6X sodium chloride/sodium citrate (SSC) at about 45° C., followed by one or more washes in 0.2X SSC, 0.1% SDS at 50° C. Another example of stringent hybridization conditions are hybridization in 6X sodium chloride/sodium citrate (SSC) at about 45° C., followed by one or more washes in 0.2X SSC, 0.1% SDS at 55° C. A further example of stringent hybridization conditions are hybridization in 6X sodium chloride/sodium citrate (SSC) at about 45° C., followed by one or more washes in 0.2X SSC, 0.1% SDS at 60° C. Preferably, stringent hybridization conditions are hybridization in 6X sodium chloride/sodium citrate (SSC) at about 45° C., followed by one or more washes in 0.2X SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2X SSC, 1% SDS at 65° C. Preferably, an isolated nucleic acid molecule of the invention that hybridizes under stringent conditions to the sequence of SEQ ID NO:1, 4 or 7, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a jAZF1, jjAZ1 or jAZF1/jjAZ1 protein, preferably a mammalian jAZF1, jjAZ1 or jAZF1/jjAZ1 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of jAZF1, jjAZ1 or jAZF1/jjAZ1 protein having less than about 30%, 20%, 10% and more preferably 5% (by dry weight), of non-jAZF1, jjAZ1 or jAZF1/jjAZ1 protein (also referred to herein as a "contaminating protein"), or of chemical precursors or non-jAZF1, jjAZ1 or jAZF1/jjAZ1 chemicals. When the jAZF1, jjAZ1 or jAZF1/jjAZ1 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of jAZF1, jjAZ1 or jAZF1/jjAZ1 (e.g., the sequence of SEQ ID NO:1, SEQ ID NO:3, SEQ ID NO:4, SEQ ID NO:6, SEQ ID NO:7, or SEQ ID NO:9, without abolishing or more preferably, without substantially altering a biological activity, whereas an "essential" amino acid residue results in such a change. For example, amino acid residues that are conserved among the polypeptides of the present invention, e.g., those present in the zinc finger domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a jAZF1, jjAZ1 or jAZF1/jjAZ1 protein is preferably replaced with another amino acid residue from the same side chain family. Alternatively, in another embodiment, mutations can be introduced randomly along all or part of a jAZF1, jjAZ1 or jAZF1/jjAZ1 coding sequence, such as by saturation mutagenesis, and the resultant mutants can be screened for jAZF1, jjAZ1 or jAZF1/jjAZ1 biological activity to identify mutants that retain activity. Following mutagenesis of SEQ ID NO:1, SEQ ID NO:3, SEQ ID NO:4, SEQ ID NO:6, SEQ ID NO:7, or SEQ ID NO:9, the encoded protein can be expressed recombinantly and the activity of the protein can be determined.

Calculations of homology or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the jAZF1, jjAZ1 or jAZF1/jjAZ1 amino acid sequence of SEQ ID NO:2, SEQ ID NO:5 OR SEQ ID NO:8 are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403–10. BLAST nucleotide searches can be performed with the NBLAST program, score =100, wordlength =12 to obtain nucleotide sequences homologous to jAZF1, jjAZ1 or jAZF1/jjAZ1 nucleic acid molecules of the invention. BLAST protein searches can be performed with the XBLAST program, score =50, wordlength =3 to obtain amino acid sequences homologous to jAZF1, jjAZ1 or jAZF1/jjAZ1 protein molecules of the invention. To obtain gapped alignments for comparison purposes, Gapped BLAST can be utilized as described in Altschul et al., (1997)]Nucleic Acids Res. 25(17):3389–3402. When utilizing BLAST and Gapped BLAST programs, the default parameters of the respective programs (e.g., XBLAST and NBLAST) can be used.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Other features and advantages of the invention will be apparent from the following detailed description, and from the claims.

BRIEF DESCRIPTION OF THE DRAWINGS

FIG. 1 depicts a cDNA sequence (SEQ ID NO:1) and predicted amino acid sequence (SEQ ID NO:2) of human jAZF1. The methionine-initiated open reading frame of human jAZF1, jjAZ1 or jAZF1/jjAZ1 (without the 5' and 3' untranslated regions) starts at nucleotide 52 until nucleotide 781 of SEQ ID NO:1 (shown also as coding sequence (SEQ ID NO:3)).

FIG. 2 depicts a cDNA sequence (SEQ ID NO:4) and predicted amino acid sequence (SEQ ID NO:5) of human jjAZ1. The methionine-initiated open reading frame of human jjAZ1 (without the 5' and 3' untranslated regions) starts at nucleotide 195 until nucleotide 2411 of SEQ ID NO:4 (shown also as coding sequence (SEQ ID NO:6)).

FIG. 3 depicts a cDNA sequence (SEQ ID NO:7) and predicted amino acid sequence (SEQ ID NO:8) of human jAZF1/jjAZ1. The methionine-initiated open reading frame of human jAZF1/jjAZ1 (without the 5' and 3' untranslated regions) starts at nucleotide 52 until nucleotide 2379 of SEQ ID NO:7 (shown also as coding sequence (SEQ ID NO:9)).

FIGS. 4A–D are a schematic representation that depict the genomic structures of normal jAZF1 (FIG. 4A) and jjAZ1 (FIG. 4C) genes, their processed transcripts (FIGS. 4B and D, respectively), and the positions of the breakpoints in the t(7;17)(p15;q21) (shown with the double-headed arrows).

DETAILED DESCRIPTION

The invention is based on the discovery of the DNA surrounding the breakpoint of a recurrent chromosomal translocation, t(7;17)(p15;q21), initially reported in several cases of low grade ESS. The recombination at this breakpoint results in a fusion of two previously unknown zinc-finger proteins, which are termed JAZF1 and JJAZ1. Fusion of the JAZF1 and JJAZ1 genes is a common occurrence in several different types of uterine stromal tumors. The fusion is not limited to low grade ESSs, in which the t(7;17)(p15;q21) was originally described, but is also present in at least some stromal nodules, high grade ESSs, and UUSs. Thus, the detection of the jAZF1/jjAZ1 gene fusion is indicative of an endometrial stromal tumor.

The human jAZF1 sequence (FIG. 1; SEQ ID NO:1), which is approximately 3010 nucleotides long including untranslated regions, contains a predicted methionine-initiated coding sequence of about 729 nucleotides (nucleotides 52–781 of SEQ ID NO:1; SEQ ID NO:3). The coding sequence encodes a 243 amino acid protein (SEQ ID NO:2). The shaded boxes in FIG. 1 indicate the amino acids that code for $C_2H_2$ zinc finger domain; the double underline indicates the amino acids that code for the bipartite nuclear localization signal. The breakpoint in between amino acids 129 and 130 are indicated by the vertical line.

The human jjAZ1 sequence (FIG. 2; SEQ ID NO:4, which is approximately 4441 nucleotides long including untranslated regions, contains a predicted methionine-initiated coding sequence of about 2217 nucleotides (nucleotides 195–2411 of SEQ ID NO:4; SEQ ID NO:6). The coding sequence encodes a 739 amino acid protein (SEQ ID NO:4). The shaded box in FIG. 2 indicates the amino acids that code for $C_2H_2$ zinc finger domain; the double underline indicates the amino acids that code for the bipartite nuclear localization signal. The breakpoint is between amino acids 92 and 93 are indicated by the vertical line.

The human jAZF1/jjAZ1 sequence (FIG. 3; SEQ ID NO:7, which is approximately 4409 nucleotides long including untranslated regions, contains a predicted methionine-initiated coding sequence of about 2328 nucleotides (nucleotides 52–2379 of SEQ ID NO:7; SEQ ID NO:9). The coding sequence encodes a 776 amino acid protein (SEQ ID NO:8). The shaded boxes in FIG. 1 indicate the amino acids that code for $C_2H_2$ zinc finger domain; the double underline indicates the amino acids that code for the bipartite nuclear localization signal. The 5' portion of the gene is contributed by jAZF1 and the 3' portion of the gene is contributed by jjAZ1; the fusion is indicated by the vertical line.

As the jAZF1, jjAZ1 or jAZF1/jjAZ1 polypeptides of the invention may modulate jAZF1, jjAZ1 or jAZF1/jjAZ1-mediated activities, they may be useful as of for developing novel diagnostic and therapeutic agents for jAZF1, jjAZ1 or jAZF1/jjAZ1-mediated or related disorders, as described below. For example, the jAZF1 or jjAZ1 proteins act as transcription factors controlling transcription in a cell, and therefore may be used to modulate cell proliferation. Alternatively, the jAZF1/jjAZ1 molecules can act as novel diagnostic targets for detecting endometrial stromal tumors and differentiating endometrial stromal tumors from non-stromal sarcomas.

More particularly, the presence of jAZF1/jjAZ1 RNA or protein can be used to identify a cell or tissue, or other biological sample, as being derived from enodmetrial stromal tumor. Expression can be determined by evaluating RNA, e.g., by hybridization of a jAZF1/jjAZ1 specific probe, or with a jAZF1/jjAZ1 specific antibody.

As the jAZF1/jjAZ1 mRNA is expressed in an endometrial stromal tumor, it is likely that the expression of jAZF1/jjAZ1 molecules is associated with endometrial stromal tumor. For example, expression and/or activity of a jAZF1/jjAZ1 molecule can lead to an endometrial stromal tumor growth. Thus, the jAZF1/jjAZ1 molecules can act as novel diagnostic targets and small molecules that bind the protein fusion can act as therapeutic agents for controlling this class of tumors.

The jAZF1, jjAZ1 or jAZF1/jjAZ1 protein, fragments thereof, and derivatives and other variants of the sequence in SEQ ID NO:2, SEQ ID NO:5 OR SEQ ID NO:8 thereof are collectively referred to as "polypeptides or proteins of the invention" or "jAZF1, jjAZ1 or jAZF1/jjAZ1 polypeptides or proteins". Nucleic acid molecules encoding such polypeptides or proteins are collectively referred to as "nucleic acids of the invention" or "JAZF1, jjAZ1or jAZF1/jjAZ1 nucleic acids." jAZF1, jjAZ1 or jAZF1/jjAZ1 molecules refer to jAZF1, jjAZ1 or jAZF1I/jjAZ1 nucleic acids, polypeptides, and antibodies.

Various aspects of the invention are described in further detail below.

Isolated Nucleic Acid Molecules

In one aspect, the invention provides, an isolated or purified, nucleic acid molecule that encodes a jAZF1, jjAZ1 or jAZF1/jjAZ1 polypeptide described herein, e.g., a full length jAZF1, jjAZ1 or jAZF1/jjAZ1 protein or a fragment thereof, e.g., a biologically active portion of jAZF1, jjAZ1 or jAZF1/jjAZ1 protein. Also included is a nucleic acid fragment suitable for use as a hybridization probe, which can be used, e.g., to a identify nucleic acid molecule encoding a polypeptide of the invention, jAZF1, jjAZ1 or jAZF1/jjAZ1 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, 4, or 7, or a portion of any of these nucleotide sequences. In one embodiment, the nucleic acid molecule includes sequences encoding the human jAZF1, jjAZ1 or jAZF1/jjAZ1 protein, as well as 5' untranslated sequences. Alternatively, the nucleic acid molecule can include only the coding region of SEQ ID NO:1, 4 or 7 and, e.g., no flanking sequences which normally accompany the subject sequence.

In another embodiment, an isolated nucleic acid molecule of the invention includes a nucleic acid molecule which is a complement of the nucleotide sequence shown in SEQ ID NO:1, 3, 4, 6, 7 or 9, or a portion of any of these nucleotide sequences. In other embodiments, the nucleic acid molecule of the invention is sufficiently complementary to the nucleotide sequence shown in SEQ ID NO:1, 3, 4, 6, 7 or 9, such that it can hybridize to the nucleotide sequence shown in SEQ ID NO:1, SEQ ID NO:3, SEQ ID NO:4, SEQ ID NO:6, SEQ ID NO:7, or SEQ ID NO:9, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:7 or 9, or a portion, preferably of the same length, of any of these nucleotide sequences.

A nucleic acid molecule of the invention can include only a portion of the nucleic acid sequence of SEQ ID NO:1, SEQ ID NO:3, SEQ ID NO:4, SEQ ID NO:6, SEQ ID NO:7, or SEQ ID NO:9. For example, such a nucleic acid molecule can include a fragment which can be used as a probe or primer or a fragment encoding a portion of a jAZF1, jjAZ1 or jAZF1/jjAZ1 protein, e.g., an immunogenic or biologically active portion of a jAZF1, jjAZ1 or jAZF1/jjAZ1 protein. A fragment can comprise nucleotides 1503 to 1575 of SEQ ID NO:7, which encodes a $C_2H_2$ zinc finger domain of human jAZF1/jjAZ1. The nucleotide sequence determined from the cloning of the jAZF1, jjAZ1 or jAZF1/jjAZ1 gene allows for the generation of probes and primers designed for use in identifying and/or cloning other jAZF1, jjAZ1 or jAZF1/jjAZ1 family members, or fragments thereof, as well as jAZF1, jjAZ1 or jAZF1/jjAZ1 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particulary fragments thereof which are at least 20 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment contains a $C_2H_2$ zinc finger domain.

jAZF1, jjAZ1 or jAZF1/jjAZ1 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1, SEQ ID NO:3, SEQ ID NO:4, SEQ ID NO:6, SEQ ID NO:7, or SEQ ID NO:9, or of a naturally occurring allelic variant or mutant of SEQ ID NO:1, SEQ ID NO:3, SEQ ID NO:4, SEQ ID NO:6, SEQ ID NO:7, or SEQ ID NO:9.

The invention further encompasses nucleic acid molecules that differ from the nucleotide sequence shown in SEQ ID NO:1, 3, 4, 6, 7 or 9. Such differences can be due to degeneracy of the genetic code (and result in a nucleic acid which encodes the same jAZF1, jjAZ1 or jAZF1I/jjAZ1 proteins as those encoded by the nucleotide sequence disclosed herein.) In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2, SEQ ID NO:5 OR SEQ ID NO:8.

Antisense Nucleic Acid Molecules, Ribozymes and Modified jAZF1, jjAZ1 or jAZF1/jjAZ1 Nucleic Acid Molecules In another aspect, the invention features, an isolated nucleic acid molecule which is antisense to jAZF1, jjAZ1 or jAZF1/jjAZ1. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire jAZF1, jjAZ1 or jAZF1/jjAZ1 coding strand, or to only a portion thereof (e.g., the coding region of human jAZF1/jjAZ1 corresponding to SEQ ID NO:9). In another embodiment, the antisense nucleic acid molecule is antisense to a "noncoding region" of the coding strand of a nucleotide sequence encoding jAZF1, jjAZ1 or jAZF1/jjAZ1 (e.g., the 5' and 3' untranslated regions).

An antisense nucleic acid can be designed such that it is complementary to the entire coding region of jAZF1, jjAZ1 or jAZF1/jjAZ1 mRNA, but more preferably is an oligonucleotide which is antisense to only a portion of the coding or noncoding region of jAZF1, jjAZ1 or jAZF1I/jjAZ1 mRNA. For example, the antisense oligonucleotide can be complementary to the region surrounding the translation start site of jAZF1, jjAZ1 or jAZF1/jjAZ1 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a jAZF1, jjAZ1 or jAZF1/jjAZ1 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An a-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. A ribozyme having specificity for a jAZF1, jjAZ1 or jAZF1/jjAZ1-encoding nucleic acid can include one or more sequences complementary to the the nucleotide sequence of a jAZF1, jjAZ1 or jAZF1/jjAZ1 cDNA disclosed herein (i.e., SEQ ID NO:1, 3, 4, 6, 7 or 9), and a sequence having known catalytic sequence responsible for mRNA cleavage (see U.S. Pat. No. 5,093,246 or Haselhoff and Gerlach (1988) *Nature* 334:585–591). For example, a derivative of a *Tetrahymena* L-19 IVS RNA can be constructed in which the nucleotide sequence of the active site is complementary to the nucleotide sequence to be cleaved in a jAZF1, jjAZ1 or jAZF1/jjAZ1-encoding mRNA. See, e.g., Cech et al. U.S. Pat. No. 4,987,071; and Cech et al. U.S. Pat. No. 5,116,742. Alternatively, jAZF1, jjAZ1 or jAZF1/jjAZ1 mRNA can be used to select a catalytic RNA having a specific ribonuclease activity from a pool of RNA molecules. See, e.g., Bartel, D. and Szostak, J. W. (1993) *Science* 261:1411–1418.

jAZF1, jjAZ1 or jAZF1/jjAZ1 gene expression can be inhibited by targeting nucleotide sequences complementary to the regulatory region of the jAZF1, jjAZ1 or jAZF1/jjAZ1 (e.g., the jAZF1, jjAZ1 or jAZF1/jjAZ1 promoter and/or enhancers) to form triple helical structures that prevent transcription of the jAZF1, jjAZ1 or jAZF1/jjAZ1 gene in target cells.

The invention also provides detectably labeled oligonucleotide primer and probe molecules. Typically, such labels are chemiluminescent, fluorescent, radioactive, or colorimetric. The invention also includes molecular beacon oligonucleotide primer and probe molecules having at least one region which is complementary to a jAZF1, jjAZ1 or jAZF1/jjAZ1 nucleic acid of the invention, two complementary regions one having a fluorophore and one a quencher such that the molecular beacon is useful for quantitating the presence of the JAZF1, jjAZ1 or jAZF1/jjAZ1 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated jAZF1, jjAZ1 or jAZF1/jjAZ1 Polypeptides

In another aspect, the invention features, an isolated jAZF1, jjAZ1 or jAZF1/jjAZ1 protein, or fragment, e.g., a biologically active portion, for use as immunogens or antigens to raise or test (or more generally to bind) anti-jAZF1, jjAZ1 or jAZF1/jjAZ1 antibodies. JAZF1, jjAZ1 or jAZF1/jjAZ1 protein can be isolated from cells or tissue sources using standard protein purification techniques, jAZF1, jjAZ1 or jAZF1/jjAZ1 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., gylcosylation or cleavage, present when expressed in a native cell.

In a preferred embodiment, the jAZF1/jjAZ1 protein, or fragment thereof, differs from the corresponding sequence in SEQ ID NO:8. In one embodiment it differs by at least one but by less than 15, 10 or 5 amino acid residues. In another it differs from the corresponding sequence in SEQ ID NO:8 by at least one residue but less than 20%, 15%, 10% or 5% of the residues in it differ from the corresponding sequence in SEQ ID NO:8.

Other embodiments include a protein that contain one or more changes in amino acid sequence, e.g., a change in an amino acid residue which is not essential for activity. Such jAZF1/jjAZ1 proteins differ in amino acid sequence from SEQ ID NO:8, yet retain biological activity.

In one embodiment, the protein includes an amino acid sequence at least about 50%, 55%, 60%, 65%, 70%, 75%, 80%, 85%, 90%, 95%, 98% or more homologous to SEQ ID NO:8.

In one embodiment, a biologically active portion of a jAZF1/jjAZ1 protein includes a $C_2H_2$ zinc finger domain. Moreover, other biologically active portions, in which other regions of the protein are deleted, can be prepared by recombinant techniques and evaluated for one or more of the functional activities of a native jAZF1, jjAZ1 or jAZF1/jjAZ1 protein.

In a preferred embodiment, the jAZF1, jjAZ1 or jAZF1/jjAZ1 protein has an amino acid sequence shown in SEQ ID NO:2, 5, or 8. In other embodiments, the JAZF1, jjAZ1 or jAZF1/jjAZ1 protein is substantially identical to SEQ ID NO:2, 5, or 8. In yet another embodiment, the jAZF1, jjAZ1 or jAZF1/jjAZ1 protein is substantially identical to SEQ ID NO:2, 5, or 8 and retains the functional activity of the protein of SEQ ID NO:2, SEQ ID NO:5 or SEQ ID NO:8.

JAZF1, jjAZ1 or jAZF1/jjAZ1 Chimeric or Fusion Proteins

In another aspect, the invention provides jAZF1, jjAZ1 or jAZF1/jjAZ1 chimeric or fusion proteins. As used herein, a jAZF1, jjAZ1 or jAZF1/jjAZ1 "chimeric protein" or "fusion protein" includes a jAZF1, jjAZ1 or jAZF1/jjAZ1 polypeptide linked to anon-jAZF1, jjAZ1 or jAZF1/jjAZ1 polypeptide. A "non-jAZF1, jjAZ1 or jAZF1/jjAZ1 polypeptide" refers to a polypeptide having an amino acid sequence corresponding to a protein which is not substantially homologous to the jAZF1, jjAZ1 or jAZF1/jjAZ1 protein, e.g., a protein which is different from the JAZF1, jjAZ1 or jAZF1/jjAZ1 protein and which is derived from the same or a different organism. The jAZF1, jjAZ1 or jAZF1/jjAZ1 polypeptide of the fusion protein can correspond to all or a portion e.g., a fragment described herein of a jAZF1, jjAZ1 or jAZF1/jjAZ1 amino acid sequence. In a preferred embodiment, a jAZF1, jjAZ1 or jAZF1/jjAZ1 fusion protein includes at least one (or two) biologically active portion of a jAZF1, jjAZ1 or jAZF1/jjAZ1 protein. The non-jAZF1, jjAZ1 or jAZF1/jjAZ1 polypeptide can be fused to the N-terminus or C-terminus of the jAZF1, jjAZ1 or jAZF1/jjAZ1 polypeptide.

The fusion protein can include a moiety which has a high affinity for a ligand. For example, the fusion protein can be a GST-JAZF1, jjAZ1 or jAZF1/jjAZ1 fusion protein in which the jAZF1, jjAZ1 or jAZF1/jjAZ1 sequences are fused to the C-terminus of the GST sequences. Such fusion proteins can facilitate the purification of recombinant jAZF1, jjAZ1 or jAZF1/jjAZ1. Alternatively, the fusion protein can be a jAZF1, jjAZ1 or jAZF1/jjAZ1 protein containing a heterologous signal sequence at its N-terminus. In certain host cells (e.g., mammalian host cells), expression and/or secretion of jAZF1, jjAZ1 or jAZF1/jjAZ1 can be increased through use of a heterologous signal sequence.

Fusion proteins can include all or a part of a serum protein, e.g., an IgG constant region, or human serum albumin.

The jAZF1, jjAZ1 or jAZF1/jjAZ1 fusion proteins of the invention can be incorporated into pharmaceutical compositions and administered to a subject in vivo. The jAZF1, jjAZ1 or jAZF1/jjAZ1 fusion proteins can be used to affect the bioavailability of a jAZF1, jjAZ1 or jAZF1/jjAZ1 substrate. JAZF1, jjAZ1 or jAZF1/jjAZ1 fusion proteins may be useful therapeutically for the treatment of disorders caused by, for example, (i) aberrant modification or mutation of a gene encoding a jAZF1, jjAZ1 or jAZF1/jjAZ1 protein; (ii) mis-regulation of the jAZF1, jjAZ1 or jAZF1/jjAZ1 gene; and (iii) aberrant post-translational modification of a jAZF1, jjAZ1 or jAZF1/jjAZ1 protein.

Moreover, the jAZF1, jjAZ1 or jAZF1/jjAZ1-fusion proteins of the invention can be used as immunogens to produce anti-jAZF1, jjAZ1 or jAZF1/jjAZ1 antibodies in a subject, to purify jAZF1, jjAZ1 or jAZF1/jjAZ1 ligands and in screening assays to identify molecules which inhibit the interaction of jAZF1, jjAZ1 or jAZF1/jjAZ1 with a jAZF1, jjAZ1 or jAZF1/jjAZ1 substrate.

Expression vectors are commercially available that already encode a fusion moiety (e.g., a GST polypeptide). A jAZF1, jjAZ1 or jAZF1/jjAZ1-encoding nucleic acid can be cloned into such an expression vector such that the fusion moiety is linked in-frame to the jAZF1, jjAZ1 or jAZF1/jjAZ1 protein.

Anti-jAZF1 jjAZ1 or jAZF1/jjAZ1 Antibodies

In another aspect, the invention provides an anti-jAZF1, jjAZ1 or jAZF1/jjAZ1 antibody. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length jAZF1, jjAZ1 or jAZF1/jjAZ1 protein or, antigenic peptide fragment of jAZF1, jjAZ1 or jAZF1/jjAZ1 can be used as an immunogen or can be used to identify anti-jAZF1, jjAZ1 or jAZF1/jjAZ1 antibodies made with other immunogens, e.g., cells, membrane preparations, and the like. The antigenic peptide of jAZF1, jjAZ1 or jAZF1/jjAZ1 should include at least 8 amino acid residues of the amino acid sequence shown in SEQ ID NO:2, 5 or 8 and encompasses an epitope of JAZF1, jjAZ1 or jAZF1/jjAZ1. Preferably, the antigenic peptide includes at least 10 amino acid residues, more preferably at least 15 amino acid residues, even more preferably at least 20 amino acid residues, and most preferably at least 30 amino acid residues.

Preferred epitopes encompassed by the antigenic peptide are regions of jAZF1, jjAZ1or jAZF1/jjAZ1 are located on the surface of the protein, e.g., hydrophilic regions, as well as regions with high antigenicity. For example, an Emini surface probability analysis of the human jAZF1, jjAZ1 or jAZF1/jjAZ1 protein sequence can be used to indicate the regions that have a particularly high probability of being localized to the surface of the jAZF1, jjAZ1 or jAZF1l/jjAZ1 protein and are thus likely to constitute surface residues useful for targeting antibody production.

In a preferred embodiment the antibody binds specifically to the jAZF1/jjAZ1 fusion protein and does not bind to the jAZF1 or jjAZ1 polypeptides. An anti-jAZF1/jjAZ1 antibody (e.g., monoclonal antibody) can be generated using standard techniques. For example, monoclonal antibodies can be generated against a polypeptide sequence that occurs at the breakpoint of the fusion protein, e.g. against amino acids 115–135 of SEQ ID NO:8. The ability to select for antibodies that bind the fusion protein and not to jAZF1 or jjAZ1 can be accomplished by screening for antibodies that only bind the fusion protein, e.g., using standard techniques, such as immunoprecipitation. A specific anti-jAZF1/jjAZ1 antibody (e.g., monoclonal antibody) that does not bind to jAZF1 or jjAZ1 can be used to detect a jAZF1/jjAZ1 protein (e.g., in a biological sample that is suspected of being an endometrial stromal tumor) in order to evaluate the abundance and pattern of expression of the protein.

Anti-jAZF1/jjAZ1 antibodies can be used diagnostically to monitor protein levels in tissue as part of a clinical testing procedure, e.g., to, for example, determine the efficacy of a given treatment regimen, e.g., the treatment of an endometrial stromal tumor. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H. Portions or fragments of the nucleic acid sequences identified herein can be used as polynucleotide reagents.

Chimeric, humanized, but most preferably, completely human antibodies are desirable for applications which include repeated administration, e.g., therapeutic treatment (and some diagnostic applications) of human patients.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a jAZF1, jjAZ1 or jAZF1/jjAZ1 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences.

The recombinant expression vectors of the invention can be designed for expression of JAZF1, jjAZ1 or jAZF1/jjAZ1 proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., Antisense RNA as a molecular tool for genetic analysis, *Reviews—Trends in Genetics*, Vol. 1(1) 1986.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation A host cell of the invention can be used to produce (i.e., express) a JAZF1, jjAZ1 or jAZF1/jjAZ1 protein. Accordingly, the invention further provides methods for producing a jAZF1, jjAZ1 or jAZF1/jjAZ1 protein using the host cells of the invention.

Transgenic Animals

The invention provides non-human transgenic animals. Such animals are useful for studying the function and/or activity of a jAZF1, jjAZ1 or jAZF1/jjAZ1 protein and for identifying and/or evaluating modulators of jAZF1, jjAZ1 or jAZF1/jjAZ1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangment, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous jAZF1, jjAZ1 or jAZF1/jjAZ1 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a jAZF1, jjAZ1 or jAZF1/jjAZ1 protein to particular cells. A transgenic founder animal can be identified based upon the presence of a jAZF1, jjAZ1 or jAZF1/jjAZ1 transgene in its genome and/or expression of jAZF1, jjAZ1 or jAZF1/jjAZ1 mRNA in tissues or cells of the animals. A transgenic founder animal can then be used to breed additional animals carrying the transgene. Moreover, transgenic animals carrying a transgene encoding a jAZF1, jjAZ1 or jAZF1/jjAZ1 protein can further be bred to other transgenic animals carrying other transgenes. In a preferred embodiment, a jAZF1/jjAZ1 fusion transgene is introduced into a transgenic animal and that animal can serve as an animal model for endometrial stromal tumors.

jAZF1, jjAZ1 or jAZF1/jjAZ1 proteins or polypeptides can be expressed in transgenic animals, e.g., a nucleic acid encoding the protein or polypeptide can be introduced into the genome of an animal. The invention also includes a population of cells from a transgenic animal, as discussed.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a jAZF1, jjAZ1 or jAZF1/jjAZ1 protein (e.g., via a recombinant expression vector in a host cell in gene therapy applications), to detect a jAZF1, jjAZ1 or jAZF1/jjAZ1 mRNA (e.g., in a biological sample) and to modulate jAZF1, jjAZ1 or jAZF1/jjAZ1 activity, as described further below. The jAZF1or jjAZ1 can be used to treat disorders characterized by insufficient or excessive production of a jAZF1or jjAZ1. In addition, the jAZF1, jjAZ1 or jAZF1/jjAZ1 proteins can be used to screen for naturally occurring jAZF1, jjAZ1 or jAZF1/jjAZ1 substrates, to screen for drugs or compounds which modulate jAZF1, jjAZ1 or jAZF1/jjAZ1 activity, as well as to treat disorders characterized by insufficient or excessive production of jAZF1, jjAZ1 or jAZF1/jjAZ1 protein or production of jAZF1, jjAZ1 or jAZF1/jjAZ1 protein forms which have decreased, aberrant or unwanted activity compared to jAZF1, jjAZ1 or jAZF1/jjAZ1 wild type protein (e.g., expression of jAZF1/jjAZ1 gene sequence is associated with endometrial stromal tumor growth). Moreover, the anti-jAZF1, jjAZ1 or jAZF1/jjAZ1 antibodies of the invention can be used to detect and isolate JAZF1, jjAZ1 or jAZF1/jjAZ1 proteins, regulate the bioavailability of jAZF1, jjAZ1 or jAZF1/jjAZ1 proteins, and modulate jAZF1, jjAZ1 or jAZF1/jjAZ1 activity.

A method of evaluating a compound for the ability to interact with, e.g., bind, a subject jAZF1, jjAZ1 or jAZF1/jjAZ1 polypeptide is provided. For example, the method includes: contacting the compound with the subject jAZF1/jjAZ1 polypeptide; and evaluating ability of the compound to interact with, e.g., to bind or form a complex with the subject jAZF1/jjAZ1 polypeptide. This method can be performed in vitro, e.g., in a cell free system, or in vivo, e.g., in a two-hybrid interaction trap assay. This method can be used to identify naturally occurring molecules which interact with subject jAZF1/jjAZ1 polypeptide. It can also be used to find natural or synthetic inhibitors of subject jAZF1/jjAZ1 polypeptide. Screening methods are discussed in more detail below.

Screening Assays:

The invention provides methods (also referred to herein as "screening assays") for identifying modulators, i.e., candidate or test compounds or agents (e.g., proteins, peptides, peptidomimetics, peptoids, small molecules or other drugs) which bind to jAZF1, jjAZ1 or jAZF1/jjAZ1 proteins, have a stimulatory or inhibitory effect on, for example, jAZF1, jjAZ1 or jAZF1/jjAZ1 expression or jAZF1, jjAZ1 or jAZF1/jjAZ1 activity, or have a stimulatory or inhibitory effect on, for example, the expression or activity of a jAZF1, jjAZ1 or jAZF1/jjAZ1 substrate. Compounds thus identified can be used to modulate the activity of target gene products (e.g., jAZF1, jjAZ1 or jAZF1/jjAZ1 genes) in a therapeutic protocol, to elaborate the biological function of the target gene product, or to identify compounds that disrupt normal target gene interactions. For example, expression of a jAZF1/jjAZ1 fusion gene is associated with endometrial stromal tumor growth. The identification of a compound which downregulates jAZF1/jjAZ1 fusion gene expression may be useful in inhibiting growth of an endometrial stromal tumor.

In one embodiment, the invention provides assays for screening candidate or test compounds which are substrates of a jAZF1, jjAZ1 or jAZF1/jjAZ1 protein or polypeptide or a biologically active portion thereof. In another embodiment, the invention provides assays for screening candidate or test compounds which bind to or modulate the activity of a jAZF1, jjAZ1 or jAZF1/jjAZ1 protein or polypeptide or a biologically active portion thereof.

The test compounds of the present invention can be obtained using any of the numerous approaches in combinatorial library methods known in the art, including: biological libraries; peptoid libraries [libraries of molecules having the fanctionalities of peptides, but with a novel, non-peptide backbone which are resistant to enzymatic degradation but which nevertheless remain bioactive] (see, e.g., Zuckermann, R. N. et al. *J. Med. Chem.* 1994, 37:

2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) Biotechniques 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J, Mol. Biol.* 222:301–310); (Ladner *supra*).

In one embodiment, an assay is a cell-based assay in which a cell which expresses a jAZF1, jjAZ1 or jAZF1/jjAZ1 protein or biologically active portion thereof is contacted with a test compound, and the ability of the test compound to modulate jAZF1, jjAZ1 or jAZF1/jjAZ1 activity is determined. Determining the ability of the test compound to modulate jAZF1, jjAZ1 or jAZF1/jjAZ1 activity can be accomplished by monitoring, for example, endometrial stromal tumor growth.

The ability of the test compound to modulate jAZF1, jjAZ1 or jAZF1/jjAZ1 binding to a compound, e.g., a jAZF1, jjAZ1 or jAZF1/jjAZ1 substrate, or to bind to jAZF1, jjAZ1 or jAZF1/jjAZ1 can also be evaluated. This can be accomplished, for example, by coupling the compound, e.g., the substrate, with a radioisotope or enzymatic label such that binding of the compound, e.g., the substrate, to jAZF1, jjAZ1 or jAZF1/jjAZ1 can be determined by detecting the labeled compound, e.g., substrate, in a complex. Alternatively, jAZF1, jjAZ1 or jAZF1/jjAZ1 could be coupled with a radioisotope or enzymatic label to monitor the ability of a test compound to modulate jAZF1, jjAZ1 or jAZF1/jjAZ1 binding to a jAZF1, jjAZ1 or jAZF1/jjAZ1 substrate in a complex. For example, compounds (e.g., jAZF1, jjAZ1 or jAZF1/jjAZ1 substrates) can be labeled with 125I, 35S, $^{14}$C, or $^3$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a jAZF1, jjAZ1 or jAZF1/jjAZ1 substrate) to interact with jAZF1, jjAZ1 or jAZF1/jjAZ1 with or without the labeling of any of the interactants can be evaluated. For example, a microphysiometer can be used to detect the interaction of a compound with jAZF1, jjAZ1 or jAZF1/jjAZ1 without the labeling of either the compound or the jAZF1, jjAZ1 or jAZF1/jjAZ1. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and jAZF1, jjAZ1 or jAZF1/jjAZ1.

In yet another embodiment, a cell-free assay is provided in which a jAZF1, jjAZ1 or jAZF1/jjAZ1 protein or biologically active portion thereof is contacted with a test compound and the ability of the test compound to bind to the jAZF1, jjAZ1 or jAZF1/jjAZ1 protein or biologically active portion thereof is evaluated. Preferred biologically active portions of the jAZF1, jjAZ1 or jAZF1/jjAZ1 proteins to be used in assays of the present invention include fragments which participate in interactions with non-jAZF1, jjAZ1 or jAZF1/jjAZ1 molecules, e.g., fragments with high surface probability scores.

Soluble and/or membrane-bound forms of isolated proteins (e.g., jAZF1, jjAZ1 or jAZF1/jjAZ1 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the jAZF1, jjAZ1 or jAZF1/jjAZ1 protein to bind to a target molecule can be accomplished using real-time Biomolecular Interaction Analysis (BIA) (see, e.g., Sjolander, S. and Urbaniczky, C. (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either jAZF1, jjAZ1 or jAZF1/jjAZ1, an anti jAZF1, jjAZ1 or jAZF1/jjAZ1 antibody or its target molecule to facilitate separation of complexed from uncomplexed forms of one or both of the proteins, as well as to accommodate automation of the assay. Binding of a test compound to a jAZF1, jjAZ1 or JAZF1/jjAZ1 protein, or interaction of a JAZF1, jjAZ1 or JAZF1/jjAZ1 protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/jAZF1, jjAZ1 or jAZF1/jjAZ1 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or jAZF1, jjAZ1 or jAZF1/jjAZ1 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of jAZF1, jjAZ1 or jAZF1/jjAZ1 binding or activity determined using standard techniques.

Other techniques for immobilizing either a jAZF1, jjAZ1 or jAZF1/jjAZ1 protein or a target molecule on matrices include using conjugation of biotin and streptavidin. Biotinylated jAZF1, jjAZ1 or jAZF1/jjAZ1 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-irnmobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with jAZF1, jjAZ1 or jAZF1/jjAZ1 protein or target molecules but which do not interfere with binding of the jAZF1, jjAZ1 or jAZF1/jjAZ1 protein to its target molecule. Such antibodies can be derivatized to the wells of the plate, and unbound target or jAZF1, jjAZ1 or jAZF1/jjAZ1 protein trapped in the wells by antibody conjugation. Methods for detecting such complexes, in addition to those described above for the GST-immobilized complexes, include immunodetection of complexes using antibodies reactive with the jAZF1, jjAZ1 or jAZF1/jjAZ1 protein or target molecule, as well as enzyme-linked assays which rely on detecting an enzymatic activity associated with the jAZF1, jjAZ1 or jAZF1/jjAZ1 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., *Trends Biochem Sci* 1993 Aug;18(8):284–7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard, N. H., *J Mol Recognit* 1998 Winter;11 (1–6):141–8; Hage, D. S., and Tweed, S. A. *J Chromatogr B Biomed Sci Appl Oct.* 10, 1997;699(1–2):499–525). Further, fluorescence energy transfer may also be conveniently utilized, as described herein, to detect binding without further purification of the complex from solution.

In a preferred embodiment, the assay includes contacting the jAZF1, jjAZ1 or jAZF1/jjAZ1 protein or biologically active portion thereof with a known compound which binds jAZF1, jjAZ1 or jAZF1/jjAZ1 to form an assay mixture, contacting the assay mixture with a test compound, and determining the ability of the test compound to interact with a jAZF1, jjAZ1 or jAZF1/jjAZ1 protein, wherein determining the ability of the test compound to interact with a JAZF1, jjAZ1 or jAZF1/jjAZ1 protein includes determining the ability of the test compound to preferentially bind to jAZF1, jjAZ1 or jAZF1/jjAZ1 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the jAZF1, jjAZ1 or jAZF1/jjAZ1 genes herein identified. In an alternative embodiment, the invention provides methods for determining the ability of the test compound to modulate the activity of a jAZF1, jjAZ1 or jAZF1/jjAZ1 protein through modulation of the activity of a downstream effector of a jAZF1, jjAZ1 or jAZF1/jjAZ1 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the jAZF1, jjAZ1 or jAZF1/jjAZ1 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with jAZF1, jjAZ1 or jAZF1/jjAZ1 "jAZF1, jjAZ1 or jAZF1/jjAZ1-binding proteins" or "jAZF 1, jjAZ1 or jAZF1/jjAZ1-bp") and are involved in jAZF1, jjAZ1 or jAZF1/jjAZ1 activity. Such jAZF1, jjAZ1 or jAZF1/jjAZ1-bps can be activators or inhibitors of signals by the jAZF1, jjAZ1 or jAZF1/jjAZ1 proteins or jAZF1, jjAZ1 or jAZF1/jjAZ1 targets as, for example, downstream elements of a jAZF1, jjAZ1 or jAZF1/jjAZ1-mediated signaling pathway.

The two-hybrid system is based on the modular nature of most transcription factors, which consist of separable DNA-binding and activation domains. Briefly, the assay utilizes two different DNA constructs. In one construct, the gene that codes for a jAZF1, jjAZ1 or jAZF1/jjAZ1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: jAZF1, jjAZ1 or jAZF1/jjAZ1 protein can be the fused to the activator domain.) If the "bait" and the "prey" proteins are able to interact, in vivo, forming a jAZF1, jjAZ1 or jAZF1/jjAZ1 dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the jAZF1, jjAZ1 or jAZF1/jjAZ1 protein.

In another embodiment, modulators of jAZF1, jjAZ1 or jAZF1/jjAZ1 expression are identified. For example, a cell or cell free mixture is contacted with a candidate compound and the expression of jAZF1, jjAZ1 or jAZF1/jjAZ1 mRNA or protein evaluated relative to the level of expression of jAZF1, jjAZ1 or jAZF1/jjAZ1 mRNA or protein in the absence of the candidate compound. When expression of jAZF1, jjAZ1 or jAZF1/jjAZ1 mRNA or protein is greater in the presence of the candidate compound than in its absence, the candidate compound is identified as a stimulator of jAZF1, jjAZ1 or jAZF1/jjAZ1 mRNA or protein expression. Alternatively, when expression of jAZF1, jjAZ1 or jAZF1/jjAZ1 mRNA or protein is less (statistically significantly less) in the presence of the candidate compound than in its absence, the candidate compound is identified as an inhibitor of jAZF1, jjAZ1 or jAZF1/jjAZ1 mRNA or protein expression. The level of jAZF1, jjAZ1 or jAZF1/jjAZ1mRNA or protein expression can be determined by methods described herein for detecting jAZF1, jjAZ1 or jAZF1/jjAZ1 mRNA or protein.

In another aspect, the invention pertains to a combination of two or more of the assays described herein. For example, a modulating agent can be identified using a cell-based or a cell free assay, and the ability of the agent to modulate the activity of a jAZF1/jjAZ1 fusion protein can be confirmed in vivo, e.g., in an animal such as an animal model for endometrial stromal tumor growth.

This invention further pertains to novel agents identified by the above-described screening assays. Accordingly, it is within the scope of this invention to further use an agent identified as described herein (e.g., a JAZF1, jjAZ1 or jAZF1/jjAZ1 modulating agent, an antisense jAZF1, jjAZ1 or jAZF1/jjAZ1 nucleic acid molecule, a jAZF1, jjAZ1 or jAZF1/jjAZ1-specific antibody, or a jAZF1, jjAZ1 or jAZF1/jjAZ1-binding partner) in an appropriate animal model to determine the efficacy, toxicity, side effects, or mechanism of action, of treatment with such an agent. Furthermore, novel agents identified by the above-described screening assays can be used for treatments as described herein.

Diagnostics

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject has an endometrial stromal tumor, e.g., the presence of a jAZF1/jjAZ1 fusion nucleic acid or protein is indicative that the individual has an endometrial stromal tumor. The method includes detecting in a tissue of the subject, the presence of a jAZF1/jjAZ1 fusion nucleic acid, e.g., DNA or mRNA, or the jAZF1/jjAZ1 fusion protein. For example, detecting the jAZF1/jjAZ1 fusion nucleic acid can include: (i) providing a probe/primer including an oligonucleotide containing a region of nucleotide sequence which hybridizes to a sense or antisense sequence from SEQ ID NO:7; (ii) exposing the probe/primer to nucleic acid of the biological sample tissue; and detecting, by hybridization, e.g., in situ hybridization, of the probe/primer to the nucleic acid, the presence or absence of the jAZF1/jjAZ1 fusion nucleic acid. Preferably, the oligonucleotide spans the breakpoint or fusion site where the jAZF1 sequence fuses to the jjAZ1 sequence, and does not hybridize to non jAZF1/jjAZ1 fusion nucleic acids, e.g., normal jAZF1 and jjAZ1 nucleic acid sequences. The oligonucleotide that spans the breakpoint is typically about 60, 40 or 20 nucleotides in length. In a preferred example, the oligonucleotide includes between 15–25 nucleotides from the jAZF1 sequence and between 15–25 nucleotides from the jjAZ1 sequence, e.g., the oligonucleotide includes 17 nucleotides from the jAZF1 sequence and 23 nucleotides from the jjAZ1 sequence.

The discovery that jAZF1/jjAZ1 fusion nucleic acid or protein is present in endometrial stromal tumors and not in normal endometrial tissue or non-stromal tumors, provides a useful diagnostic for determining if a cellular mass is an endometrial stromal tumor. For example, the present discovery allows the distinction between a stromal tumor and a fibroid (a benign muscle tumor). Under the microscope, the cells of the endometrial stromal tumor and cells of the fibroid appear identical. The present discovery allows the differentiation between the stromal tumor and the fibroid; the absence of the jAZF1/jjAZ1 fusion nucleic acid or protein is indicative that the cellular mass is a fibroid. Since a fibroid is always benign, no further invasive action, e.g., removal of the uterous or determination whether the cellular mass is malignant, is necessary.

The present discovery is useful for identifying the origin of a tumor, e.g. for determining if a stromal tumor located at a site other than the endometrium actually arose in the endometrium. For example, a stromal tumor is identified, e.g., in the lung. If the long stromal tumor has a jAZF1/jjAZ1 fusion nucleic acid or protein, its presence is indicative that the primary site of the tumor is the uterus. This simple method prevents needless body imaging required normally to locate the primary site of a tumor.

The presence of the jAZF1/jjAZ1 fusion nucleic acid or protein can also be used to verify that the stromal tumor is from the endometrium, and therefore can be used as a tumor marker protein.

Diagnostic and Prognostic Assays

The presence, level, or absence of jAZF1/jjAZ1 protein or nucleic acid in a biological sample can be evaluated by obtaining a biological sample from a test subject and contacting the biological sample with a compound or an agent capable of detecting jAZF1/jjAZ1 fusion protein or nucleic acid (e.g., mRNA, genomic DNA) that encodes jAZF1/jjAZ1 protein such that the presence of jAZF1/jjAZ1 protein or nucleic acid is detected in the biological sample. The term "biological sample" includes tissues or cells isolated from a subject, as well as tissues and cells present within a subject. A preferred biological sample is a biopsy.

The level of expression of the jAZF1/jjAZ1 gene can be measured in a number of ways, including, but not limited to: measuring the mRNA encoded by the jAZF1/jjAZ1 genes; measuring the amount of protein encoded by the jAZF1/jjAZ1 genes; or measuring the activity of the protein encoded by the jAZF1/jjAZ1 genes.

The level of mRNA corresponding to the jAZF1/jjAZ1 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the jAZF1/jjAZ1 gene being detected. The nucleic acid probe can be, for example, a full-length jAZF1/jjAZ1 nucleic acid, such as the nucleic acid of SEQ ID NO:7, or a portion thereof, such as an oligonucleotide that spans the jAZF1/jjAZ1 nucleic acid fusion site, e.g., an oligonucleotide that is at least 7, 15, 30, 40, 50, or 100 nucleotides in length and sufficient to specifically hybridize under stringent conditions to jAZF1/jjAZ1 mRNA or genomic DNA.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the jAZF1/jjAZ1 genes.

The level of mRNA in a sample that is encoded by jAZF1/jjAZ1 can be evaluated with nucleic acid amplification, e.g., by rtPCR (Mullis, 1987, U.S. Pat. No. 4,683,202), ligase chain reaction (Barany, 1991, Proc. Natl. Acad. Sci. USA 88:189–193), self sustained sequence replication (Guatelli et al., 1990, Proc. Natl. Acad. Sci. USA 87:1874–1878), transcriptional amplification system (Kwoh et al., 1989, Proc. Natl. Acad. Sci. USA 86:1173–1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques known in the art. In general, amplification primers are from about 10 to 30 nucleotides in length and flank the fusion site of the jAZF1/jjAZ1 gene fusion.

For in situ methods, a cell or tissue sample can be prepared/processed and immobilized on a support, typically a glass slide, and then contacted with a probe that can hybridize to mRNA that encodes the jAZF1/jjAZ1 gene being analyzed.

In another embodiment, the methods further include contacting a control sample with a compound or agent capable of detecting jAZF1/jjAZ1 mRNA, or genomic DNA, and comparing the presence of jAZF1/jjAZ1 mRNA or genomic DNA in the control sample with the presence of jAZF1/jjAZ1 mRNA or genomic DNA in the test sample.

A variety of methods can be used to determine the level of protein encoded by jAZF1/jjAZ1. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect jAZF1/jjAZ1 protein in a biological sample in vitro as well as in vivo. In vitro techniques for detection of jAZF1/jjAZ1 protein include enzyme linked immunosorbent assays (ELISAs), immunoprecipitations, immunofluorescence, enzyme immunoassay (EIA), radioimmunoassay (RIA), and Western blot analysis. In vivo techniques for detection of jAZF1/jjAZ1 protein include introducing into a subject a labeled anti-jAZF1/jjAZ1 antibody. For example, the antibody can be labeled with a radioactive marker whose presence and location in a subject can be detected by standard imaging techniques.

In another embodiment, the methods further include contacting the control sample with a compound or agent capable of detecting jAZF1/jjAZ1 protein, and comparing the presence of jAZF1/jjAZ1 protein in the control sample with the presence of jAZF1, jjAZ1 or jAZF1/jjAZ1 protein in the test sample.

The invention also includes kits for detecting the presence of jAZF1/jjAZ1 in a biological sample. For example, the kit can include a compound or agent capable of detecting jAZF1/jjAZ1 protein or mRNA in a biological sample; and a standard. The compound or agent can be packaged in a suitable container. The kit can further comprise instructions for using the kit to detect jAZF1/jjAZ1 protein or nucleic acid.

For antibody-based kits, the kit can include: (1) a first antibody (e.g., attached to a solid support) which binds to a jAZF1/jjAZ1 fusion protein; and, optionally, (2) a second, different antibody which binds to either the jAZF1/jjAZ1 fusion protein or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a jAZF1/jjAZ1 fusion polypeptide or (2) a pair of primers useful for amplifying a nucleic acid molecule corresponding to a jAZF1/jjAZ1 fusion gene. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having a endometrial stromal tumor, especially those at risk of having a low grade endometrial stromal sarcomas.

The prognostic assays described herein can be used to determine whether a subject can be administered an agent (e.g., an agonist, antagonist, peptidomimetic, protein, peptide, nucleic acid, small molecule, or other drug candidate) to treat a endometrial stromal tumor associated jAZF1/jjAZ1 expression or activity.

Pharmaceutical Compositions

The nucleic acid and polypeptides, fragments thereof, as well as anti-jAZF1, jjAZ1 or jAZF1/jjAZ1 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants.

Oral compositions generally include an inert diluent or an edible carrier. For the purpose of oral therapeutic administration, the active compound can be incorporated with excipients and used in the form of tablets, troches, or capsules, e.g., gelatin capsules. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193). The pharmaceutical compositions can be included in a container, pack, or dispenser together with instructions for administration.

Methods of Treatment:

The successful treatment of jAZF1, jjAZ1 or jAZF1/jjAZ1 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of jAZF1/jjAZ1 disorders, e.g., endometrial stromal tumor growth. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

Another method by which nucleic acid molecules may be utilized in treating or preventing a disease characterized by JAZF1, jjAZ1 or jAZF1/jjAZ1 expression is through the use of aptamer molecules specific for jAZF1, jjAZ1 or jAZF1/jjAZ1 protein. Aptamers are nucleic acid molecules having a tertiary structure which permits them to specifically bind to protein ligands (see, e.g., Osborne, et al. *Curr. Opin. Chem Biol.* 1997, 1(1): 5–9; and Patel, D.J. *Curr Opin Chem Biol* 1997 Jun;1(1):32–46). Since nucleic acid molecules may in many cases be more conveniently introduced into target cells than therapeutic protein molecules may be, aptamers offer a method by which jAZF1, jjAZ1 or jAZF1/jjAZ1 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of jAZF1, jjAZ1 or jAZF1/jjAZ1 disorders.

In circumstances wherein injection of an animal or a human subject with a jAZF1/jjAZ1 protein or epitope for stimulating antibody production is harmful to the subject, it is possible to generate an immune response against jAZF1, jjAZ1 or jAZF1I/jjAZ1 through the use of anti-idiotypic antibodies (see, for example, Herlyn, D. *Ann Med* 1999;31 (1):66–78; and Bhattacharya-Chatterjee, M., and Foon, K. A. *Cancer Treat Res* 1998;94:51–68). If an anti-idiotypic antibody is introduced into a mammal or human subject, it should stimulate the production of anti-anti-idiotypic antibodies, which should be specific to the jAZF1, jjAZ1 or jAZF1/jjAZ1 protein. Vaccines directed to a disease characterized by jAZF1, jjAZ1 or jAZF1/jjAZ1 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993, Proc. Natl. Acad. Sci. USA 90:7889–7893).

The identified compounds that inhibit target gene expression, synthesis and/or activity can be administered to a patient at therapeutically effective doses to prevent, treat or ameliorate jAZF1, jjAZ1 or jAZF1/jjAZ1 disorders. A therapeutically effective dose refers to that amount of the compound sufficient to result in amelioration of symptoms of the disorders.

EXAMPLE

Example 1

Below is a description of the tissues used in the study

Tissues from four cases of low grade endometrial stromal sarcoma confirmed by cytogenetic analysis to have the t(7;17)(p15;q21) were used in these studies. In case BWH-42, the tissue was taken from a resected retroperitoneal mass diagnosed as metastatic endometrial stromal sarcoma; the patient was a 58 year old woman who at 42 years of age underwent total abdominal hysterectomy and bilateral salpingo-oophorectomy for low grade ESS. In case BWH-665, the tissue was taken from a resected pelvic mass at the vaginal apex; the patient was a 69 year old woman who at 51 years of age underwent a total abdominal hysterectomy for ESS. In case LU-550, the tissue was taken from a primary tumor diagnosed as low grade ESS that was resected as part of a simple hysterectomy; the patient was a 41 year old woman. In case LU-954, the tissue was taken from a primary tumor diagnosed as low grade ESS that was resected as part of a total abdominal hysterectomy and bilateral salpingo-oophorectomy; the patient was a 41 year old woman. The karyotypes of the four cases are listed in Table 1.

TABLE 1

Karyotypes for the four cases of LG-ESS used in these studies.

| Case | Karyotype |
| --- | --- |
| BWH-42 | 46, XX, t(7;13)(p15;p13), t(7;17)(p15;q21) |
| BWH-665 | 46, XX, t(7;17)(p15;q21) |
| LU-550 | 46, XX, t(7;17)(p15;q21) |
| LU-954 | 45, XX, del(7), t(7;17)(p15;q21) |

Primary tissue culture cells were used for all subsequent studies for cases BWH-42 and BWH-665. These cells were cultured in RPMI supplemented with 20% fetal calf serum, Mito+™ Serum Extender (Becton Dickinson, Franklin Lakes, N.J.), and bovine pituitary extract (Becton Dickinson) under standard conditions. Frozen surgical specimens were used for cases LU-550 and LU-954. In addition, formalin-fixed paraffin-embedded archival material with uncharacterized cytogenetics was used to assess the prevalence of the JAZF1–JJAZ1 gene fusion.

Example 2

A Description of the YACs, BACs, and cDNAs Used in the Study

YAC clones were obtained from CEPH mega YAC libraries purchased from Research Genetics (Huntsville, AL). YAC clones were expanded in SD media and the DNA was isolated following standard protocols. Briefly, yeast were washed twice with 50 mM $Na_2EDTA$ pH 8.0 and subsequently digested for 2 h at 37° C. with a 1 mg/mL zymolase solution in 1 M sorbitol, 100 mM sodium citrate pH 7.0, 60 mM $Na_2EDTA$, 0.7M □-mercaptoethanol. The resulting spheroplasts were lysed with 1% SDS in 1X TE (10 mM Tris-HCl pH 8.0, 0.1 mM $Na_2EDTA$) and the detergent was subsequently precipitated with 5M KOAc pH 4.8. The nucleic acid material was recovered by isopropanol precipitation and was treated for 30 min at 37° C. with a 0.5 mg/mL RNase solution in 1X TE. The DNA was subjected to standard organic extraction procedures and was recovered by ethanol precipitation.

BAC clones were selected from the CITB library (Research Genetics) by analyzing three-tiered pools of DNA derived from these clones by PCR using primers complementary to DNA in the sequence-tagged sites (STSs) CHLC-GATA91C01, D7S516, CHLC-GGAA 3F06, and WI-5230. PCR was performed using 1 µL of each DNA pool as template in a total volume of 50 µL under the following reaction conditions: 1X buffer (10 mM Tris-HCl pH 8.3, 50 mM KCl, 1.5 mM $MgCl_2$, 0.001% gelatin); 200 µM dNTPs; 1 µM of each primer; and 2.5U Taq DNA polymerase (Perkin Elmer, Branchburg, N.J.). PCR cycling conditions were as follows with minor variations of annealing temperature specific to each primer pair: 94° C. for 2 min; 30 cycles of 94° C. for 15 s, 55° C. for 30 s, 72° C. for 45 s; 72° C. for 8 min. BAC clones were expanded in LB media containing chloramphenicol (25 µg/mL) and the DNA isolated using the Plasmid Midi-kit (Qiagen, Valencia, Calif.) following the supplier's instructions.

cDNA clones were isolated from a human fetal brain cDNA library in ZAPII (Stratagene, La Jolla, Calif.) and from a human umbilical vein endothelial cell (HUVEC) library in lamda-gt11. Clones containing JAZF1 DNA were identified by standard hybridization screening of plaque lifts representing approximately $1\times10^6$ phage clones per library on MagnaGraph nylon membranes (Osmonics, Minnetonka, Minn.). This procedure resulted in the identification of the representative phage clones Br2 (JAZF1 nucleotides 74–1561) from the brain library and EC-9 (JAZF1 nucleotides 1–301) from the HUVEC library. Phage DNA was isolated from relevant clones in the lambda-gt11 HUVEC library using DEAE-cellulose according to standard methods. Phagemid cDNA clones were rescued from the ZAPII brain library using the SOLR bacterial strain and ExAssist helper phage (Stratagene) according to the supplier's instructions. The KIAA0160 clone containing the entire JJAZ1 sequence was obtained from the Kazusa DNA Research Institute. The rescued phagemid clones and the KIAA0160 clone were expanded in LB supplemented with ampicillin (100 µg/mL) and DNA purified following standard alkaline lysis plasmid preparation protocols.

Example 3

Identification of a YAC Spanning the Chromosome 7 Breakpoint

To identify a YAC containing DNA in the region of the chromosome 7 breakpoint of the t(7;17)(p15;q21), FISH was performed on metaphase preparations from case BWH-42 using as probes individual YACs from the Whitehead CEPH mega YAC contig 7.3 in the region of the HOXA gene cluster that maps to chromosomal band 7p 15. Briefly, DNA probes for fluorescence in situ hybridization (FISH) were labeled with biotin-tagged nucleoside triphosphates using the BioPrime labeling system (Life Technologies, Gaithersburg, Md.). Hybridization was performed on slides of metaphase chromosomes prepared using standard methods (REF). Pretreatment of the slides, hybridization, washing and detection were performed as previously described (Morgan et al.) with the following changes. DNA on the slides was denatured in 70% formamide/2X SSC for 2 minutes at 72° C. and dehydrated in graded alcohols at 4° C. A mixture of probe and COT-1 DNA (Life Technologies) was precipitated and resuspended in Hybrisol VI (Oncor, Gaithersburg, Md.), denatured at 65° C. for 5 minutes, pre-incubated at 37° C. for 30 minutes, and applied to the slides for hybridization at 37° C. BWH-42 harbors at(7;13(p15;p13) in addition to at7;17)(p15;q21) and no normal chromosome 7. In FISH with YAC y830D2 as probe, the hybridization signal was limited to bother der7 chromosomes, while the analysis with YAC y816F12 demonstrated hybridization to the der13 and der17 chromosomes. FISH with YACs y910G4 and y929H6 demonstrated hybridization signals on the der 17 and the der7 of the t(7;13), respectively. These results indicated that the chromosome 7 breakpoints of both the t(7;17) and the t(7;13) mapped within the 7.3 contig between YACs y830D2 and y816F12 but that the breakpoints were separated by more than 1 megabase.

The YAC containing the DNA between clones y830D2 and y910G4 was then used as a probe in FISH to confirm that it spanned the chromosome 7 breakpoint. Analysis with YAC Y908b12 of metaphase preparations of case BWH-42 demonstrated hybridization to both der7 chromosomes and the der17 chromosome, thereby demonstrating that y908B12 spanned the chromosome 7 breakpoint of the t(7;17). Additionally, analysis with YAC y908B12 of interphase nuclei from case BWH-665 showed three hybridization signals. This finding indicated that DNA in y908B12 also spanned the chromosome 7 breakpoint in this case. The FISH analysis localized the breakpoint to a region defined by the markers CHLC.GATA91C01, the most telomeric STS (sequence tagged site) contained in y830D2, and WI-5230, the most centromeric STS contained in y910G4.

Example 4

Construction of a BAC Contig Across the Chromosome 7 Breakpoint

To locate BAC clones containing DNA in the region of the chromosome 7 breakpoint, DNA in multi-tiered pools from an arrayed BAC library with 6-fold redundancy was screened by PCR using primers for the STSs demarcating the boundaries of the presumptive breakpoint region, CHLC.GATA91C01 and WI-5230, as well as the two intervening markers, D7S516 and CHLC.GGAA3F06. Screening for CHLC.GATA91C01 sequence identified BAC b60B19; D7S516 identified BAC b319D14; CHLC.GGAA3F06 identified BAC b390A17; and WI-5230 identified BAC b332C6. To determine if these BAC clone were overlapping and to assist in finding BACs to fill potential gaps between these four clones, the sequences at the ends of the inserts of the BACs were analyzed using T7 and Sp6 primer sites present in the DNA flanking the insertion site of the pBeloBAC vector. However, a preliminary search of the GenBank database with the BLAST algorithm indicated that DNA within a PAC clone, p881H5, included the telomeric sequence of clone b390A17. DNA within this PAC clone had been entirely sequenced by the Genome Sequencing Center (GSC) at Washington University as part of an effort to sequence DNA of chromosome 7. Further examination of chromosome 7 sequence data on the GSC web site using the end sequences of the BAC clones identified by our PCR screen allowed us to eliminate the majority of the gaps in our map of BAC clones for the chromosome 7 breakpoint region. FISH analysis on cases BWH-42 and BWH-665 using pooled DNA from the BACs from b60B19 to b459N13 in this contig demonstrated an identical hybridization to that seen with YAC y908B12. These results indicated that the BAC contig spanned the chromosome 7 breakpoint.

Example 5

Identification of a Gene in the Chromosome 7p15 BAC Contig and Detection of the Breakpoint by Southern Blot Analysis The availability of the extensive genomic sequence in the region of the chromosome 7 breakpoint led us to attempt identification of expressed genes in this region and to locate the position of the breakpoint relative to these genes. We first searched the EST (expressed sequence tag) database for matches to the genomic sequence after filtering out repeat regions using the RepeatMasker2 software program. Among these matches, our initial efforts focused on segments of genomic sequence that showed probable intron-exon structure. Such structure was inferred from the finding of multiple areas of sequence in an EST identical to portions of genomic sequence separated by long stretches of interposed DNA missing from the EST.

To construct probes for Southern blot analysis of tumor DNA, PCR was performed to amplify repeat-free segments of unique genomic DNA adjacent to or including the expressed sequences. A probe derived from the region of overlap between BAC b459N13 and PAC p881H5 (probe 459–10) detected non-germline bands in both BamHI and HindIII digests of tumor DNA from case BWH-42 but not in similar digests of DNA from normal fibroblasts derived from the same patient. The probe 459–10 also detected a non-germline band in a BamHI digest of tumor DNA from case BWH-665. The breakpoint region was further narrowed by hybridizing Southern blots of tumor DNA with probes containing DNA telomeric to probe 459–10. Two probes, 459-BP8 and 459-BP9, amplified from sequence lying 3kb telomeric to 459–10 and separated from each other by 798bp found to produce different patterns of bands in Southern blot analyses of DNA from cases BWH-42 and BWH-665. Probe 459-BP9 detected bands identical to those seen with probe 459–10 in the two cases. In both HindIII and BamHI digests of DNA from BWH-42, probe 459-BP8 detected non-germline bands distinct from those in case BWH-665, while in case BWH-665 probe 459-BP9 detected the non-germline band seen with probe 459–10 as well as a new non-germline band. Taken together, these results indicated that the chromosome 7 breakpoint in case BWH-421 lies in DNA between that contained in probes 459-BP8 and 459-BP9 and that the breakpoint in case BWH-665 lies within DNA sequence contained in probe 459-BP8.

Example 6

Detection of a Tumor-Specific Transcript with Hybridization Probes for DNA Near the Chromosome 7 Breakpoint The chromosome 7 breakpoint in cases BWH-42 and BWh-665 mapped to the region of putative intronic sequence predicted by the alignment of the EST AA431106 with the sequences of b459N13 and p881H5. Analysis of a series of overlapping ESTs indicated that this gene had two exons totaling at least 360 bp on the centromeric side of breakpoint and two exons totaling 2674 bp on the telomeric side. To determine whether this gene was expressed in endometrium and whether the an altered transcription product was produced as a result of recombination within the gene, a hybridization probe consisting of the three most 3' exons of the gene (nucleotides 74 to 1561 in FIG. 1) was constructed from EST sequences. This probe was hybridized to Northern blots containing polyadenylated RNA purified from normal human fibroblasts, normal human endometrium, and four cases of low grade ESSs known to harbor a t(7;17). A band corresponding to a transcript of approximately 3.2 kb appeared in analyses of RNA from both normal tissues and two tumors, and a second band corresponding to a length of about 4.5 kb appeared in analyses of RNA from all four tumors but not of RNA from either normal tissue. The two tumors that failed to show the 3.2 kb band found in normal tissues have cytogenetic abnormalities in both copies of chromosome 7, as indicated in Table 1.

To determine which part of the normal chromosome 7 gene hybridized to the 4.5 kb transcript found in tumors, two additional probes were designed to represent the portions of the gene on the centromeric and telomeric sides of the chromosome 7 breakpoint. Northern blot analysis with a 258 bp centromeric probe (including nucleotides 74 to 331; FIG. 1) yielded a pattern of bands identical to that seen with the original probe, and analysis with a 1764 bp telomeric probe (nucleotides 1120 to 2883) yielded only the 3.2 kb band. These findings indicate that the chromosome 7 gene is expressed in normal endometrium and that disruption of the penultimate intron of the gene in at least some tumors with the t(7;17) results in the production of a novel transcript that contains only the centromeric portion of the gene.

Example 7

Identification of a BAC Clone Spanning the Breakpoint on Chromosome 17

To obtain DNA sequence that could be used to identify a BAC having DNA that the chromosome 17 breakpoint, inverse PCR (I-PCR) was performed on restriction fragments of tumor DNA containing the site of recombination in the t(7;17). Briefly, Five µg of tumor and control DNA were digested to completion with HindIII restriction enzyme (NEB, Beverly, Mass.) and the HindIII was inactivated by standard extraction procedures (REF). The DNA was recovered by ethanol precipitation, resuspended in 50 µl water and quantified spectrophotometrically. Digested tumor DNA and control DNA (200 ng in 25 µl final volume) were incubated for 16 hours with 800U of T4 DNA ligase in 1× ligation buffer (NEB) at 15° C. Inverse PCR was performed using 8 ng of self-ligated DNA as template in a total volume of 50 µl under the following reaction conditions: 1× buffer (50 mM Tris-HCl pH 9.2, 16 mM $(NH_4)_2SO_4$, 4 mM $MgCl_2$, 0.05% Tween 20); 200) _M dNTPS; 2 µM of each primer; 2.5U Taq DNA polymerase (Perkin Elmer, Branchburg, N.J.) and 0.05U Vent DNA polymerase (NEB). PCR cycling conditions were as follows: 94° C. for 2 minutes; 15 cycles of 94° C. for 10 seconds, 70° C. for 150 seconds; 15 cycles of 94° C. for 10 seconds, 70° C. for 150 seconds plus 15 seconds per cycle; 70° C. for 8 minutes. Two rounds of amplification were performed with 1 µl from the initial round of PCR serving as template for the second round, using similar conditions but different pairs of primers nested with respect to one another.

A set of nested PCR primers were constructed to be complementary to DNA sequence of chromosome 7 in a tail-to-tail orientation, such that the sequences of two primers (inner and outer) that abutted the HindIII site immediately telomeric to sequence in probe 459-BP8 were separated by 450 bp from the sequences of two other primers that abutted the telomeric side of the breakpoint region determined for case BWH-42. Templates for I-PCR with these primers was prepared by HindIII digestion and followed by self-ligation of genomic DNA that had been extracted from tumor tissue in case BWH-42 and of normal fibroblasts cultured from the same patient. I-PCR amplification of these templates produced a predicted normal 3.5 kb product from both the tumor DNA and a predicted, rearranged 1.6 kb product only from the tumor DNA.

The 1.6 kb I-PCR product was ligated into the pCR2.1 Topo vector and the sequences at the ends of the insert of the resulting clone were determined using the M13 primer sites present in the vector. One end sequence corresponded to chromosome 7 sequence up to a HindIII site and then immediately diverged into non-chromosome 7 sequence. When this new sequence was used to search the Genbank database, it was found that a BAC from chromosome 17, b307A16, contained matching sequence. These results indicated that the breakpoint at chromosome 17q21 in case BWH-42 was spanned by DNA in BAC b307A16.

Example 8

Identification of a Gene in the Chromosome 17 Breakpoint Region

The genomic sequence available for BAC b307A16 was filtered using the RepeatMasker2 program and the resulting repeat-free sequence was used to search the GenBank and EST databases for DNA having intron-exon structure. A complex EST, KIAA0160, with a total 4.44 kb of sequence was found to map in genomic DNA less than 20 kb away from the chromosome 17 breakpoint; however, the first 647 bp of this EST was not present from any portion of b307A16 or the overlapping BAC b542B22. This suggested that an interstitial deletion had occurred in the genomic DNA contained in b307A16 and that the predicted gene extends beyond the chromosome 17 breakpoint. If this gene were disrupted by the chromosome 17 breakpoint, the orientation of the gene would be consistent with a fusion of this gene with the gene disrupted by the breakpoint in chromosome 7. To test this possibility, RNA derived from tumor BWH-42 and RNA from control fibroblasts was analyzed by RT-PCR using primers complementary to sense sequence a the 5' end of both the 7 and 17 genes and anti-sense sequence located at the 3' end of both genes, with the primers paired in all four possible ways. RT-PCR analysis was performed as follows. RNA derived from either the primary tissue culture cells or the frozen surgical specimens was transcribed into cDNA with Superscript II (Life Technologies) according to the supplier's instructions, using either 7 AntisenseOuter or 17 AntisenseOuter as a primer (see below). The resulting cDNA was subjected to two rounds of PCR (98° C. for 5 minutes; 10 cycles of 98° C. for 15 seconds, 65° C. minus 0.5° C. per cycle for 30 seconds, 74° C. for 1 minute; 15 cycles of 98° C. for 15 seconds, 60° C. for 30 seconds, 74° C. for 1 minute) using first the "Outer" and then the "Inner" set of primers. The JAZF1 primers were 7SenseOuter 5'-CCACAGCAGTGGAAGCCTTA-3' (SEQ ID NO:10), 7AntisenseOuter 5'-GCTTCTCTTCCCCTCCATTCAT-3' (SEQ ID NO:11), 7SenseInner 5'-ATCACCCCCTCCTCTTCATT-3' (SEQ ID NO:12), and 7 AntisenseInner 5'-GGACTCATCGCTGTCCGACT-3' (SEQ ID NO:13). The JJAZ1 primers were 17SenseOuter 5'-GTTACTCGGCCTCCTCCTCCTC-3' (SEQ ID NO:14), 17 AntisenseOuter 5'-GGTTCAAATTCATTACTGGAAACTGC-3' (SEQ ID NO:15), 17 SenseInner 5'-GAGCTTTTCCTCCAGGCCTTTG-3' (SEQ ID NO:16) and 17 AntisenseInner 5'-CCGGGTTTTGTTTGATTGAGG-3' (SEQ ID NO:17). Specific primers for glyceraldehydes 3-phosphate dehydrogenase (GAPF 5'-CACATCGCTCAGACACCATG-3' (SEQ ID NO:18) and GAPR 5'-GCCATGGAATTTGCCATGGG-3' (SEQ ID NO:19)) were used to assess the quality of the input RNA.

In these experiments, the primer pairs for the intact chromosome 17 gene amplified products from the RNA of both the normal tissue and the tumor, but the recombinant 5' chromosome 7-3' chromosome 17 pair amplified a product of 440 bp only from the tumor RNA and not from the normal RNA. The reciprocal recombinant primer pair failed to amplify a product from either of the RNA samples, 5' chromosome 7-3' chromosome 17 primer pair was then used in an RT-PCR assay of RNA derived from all four tumors used previously in Northern blot analyses and an identical product was obtained in all four samples. RT-PCR analysis of JAZF1-JJAZ expression in formalin-fixed, paraffin-embedded material was carried out using protocols similar to those for amplification of the RNA sequences for the individual genes, except for preparation of the RNA template. Total RNA was extracted from ten serial 10 μm tissue sections with 3 washes in 10 ml of xylene. An adjacent 10 μm tissue section was placed on a microscope slide and stained with hematoxylin and eosin for histologic examination. For extraction of RNA, tissue was rehydrated in two washes with 100% EtOH and was digested for 16h at 60° C. in 2 ml 1x digestion buffer (20 mM Tris-HCl pH 8.0, 20 mM $Na_2EDTA$, 2% SDS, 2.5 mg/mL proteinase K). The lysate was diluted with 8 ml Trizol and the RNA isolated according to the supplier's instructions. First-strand synthesis and nested PCR were performed as described above with the following primers: FusionOutF 5'-CACGCCACAGCAGTGGAAGC-3' (SEQ ID NO:20), FusionOutR 5'-TTTGTTCTGGAGTTTCGATGAGACA-3' (SEQ ID NO:21), FusionInnerF 5'-CCCACCCATCACCCCCTCCT-3' (SEQ ID NO:22), and FusionInnerR 5'-GGTGCTATGAGATTCCGAGTTCGAAGA-3' (SEQ ID NO:23). These results confirmed that the chromosome 17 gene was disrupted by the translocation and that a fusion transcript containing the 5' end of the chromosome 7 gene and the 3' end of the chromosome 17 gene had been created.

Example 9

Structure of the Genes Identified at 7p15 and 17q21

The sequence of the chromosome 7 gene, as was deduced from the GenBank and EST databases as well as an additional 176 bp at the 5' end acquired through screening of two cDNA libraries derived from human brain and human umbilical vein endothelial cells, is presented in FIG. 1. FIG. 2 shows the entire sequence of the jjAZF1. The entire sequence of the fusion gene present in the four cases of LG-ESS discussed above is presented in FIG. 3. The true 5' ends of these transcripts remain unknown because the open reading frames continue to the 5' ends of the sequences assembled so far. However, if more sequence is present at the 5' ends of these transcripts, this sequence is minimal because the sizes of the transcripts detected by Northern blot analyses are consistent with the 3.0 kb of sequence and 4.44 kb of sequence assembled for the chromosome 7 and chromosome 17 genes, respectively.

FIG. 4 shows the genomic structures of the normal chromosome 7 and chromosome 17 genes, their processed transcripts, and the positions of the breakpoints in the t(7;17)(p15;q21). The intron-exon structure is deduced from a comparison of two genes with the chromosome 7 BAC contig and the chromosome 17 BAC, b307A16. The normal chromosome 7 gene is comprised of five exons that span over 350 kb of genomic DNA, and the breakpoint identified in the four cases of LG-ESS disrupts the gene in the third intron. The normal chromosome 17 gene is comprised of at least 14 exons that span over 55 kb of genomic DNA, and the gene is disrupted between nucleotides 468 and 469 in the four cases of LG-ESS discussed above. Conceptual translation of the open reading frame of the chromosome 7 gene (FIG. 1) revealed an N-proximal zinc finger domain as well as a tandem pair of zinc-finger domains near the C-terminus. Similarly analysis of the chromosome 17 gene sequence (FIG. 2) revealed a zinc finger domain in the C-terminal third of the coding sequence and a bipartite nuclear localization sequence immediately downstream of the zinc-finger domain. All four of the zinc-finger domains were of the $Cys_2His_2$ class, and these represented the only identifiable structural motifs in the coding sequences as well as the only regions with extensive similarity to other known genes. In light of these structural features, we refer to the chromosome 7 gene by the acronym of JAZF1, for Juxtaposed with Another Zinc Finger 1, and the chromosome 17 gene by the acronym JJAZ1, for Joined with JAZF1.

Example 10

Production of Polyclonal Antisera Directed Against JAZF1 and JJAZ1

In order to raise antisera that recognize antigenic epitopes of JAZF1 and JJAZ1, portions of the coding sequences of each gene were expressed in bacteria as fusions with amino terminal 6X histidine moeities. These fusion proteins were purified under denaturing conditions from whole bacterial lysates using metal chelate chromatography, and the resulting proteins were used to immunize New Zealand White rabbits. Unfractionated serum samples drawn from these rabbits both prior to immunization (day 0) and after the fourth booster immunization (day 84) were assayed for the presence of antibodies that specifically recognized JAZF1, JJAZ1, or the JAZF1/JJAZ1 fusion protein. Extracts prepared from 293T cells transiently expressing myc epitope-tagged JAZF1, JJAZ1, or the JAZF1/JJAZ1 fusion protein, were fractionated and transferred to PVDF membranes. Transient expression of these proteins was accomplished by introducing cDNA clones in the pcDNA3 vector into 293T cells. The membranes were probed with preimmune and immune sera as well as a monoclonal antibody, 9E10, that specifically recognizes the myc epitope. The antiserum raised against the JAZF1 antigen specifically recognized bands corresponding to proteins of predicted size in the extracts of cells expressing JAZF1myc and JAZF1/JJAZ1 myc. The antiserum raised against the JJAZ1 antigen recognized proteins of predicted size in the extracts of cells expressing JJAZ1myc and JAZF1/JJAZ1myc. However, the myc-epitope specific monoclonal antibody only recognized bands in the extracts of cells expressing JAZF1 myc and JAZF1/JJAZ1myc and not JJAZ1myc. This finding suggests that the protein corresponding to the specific band observed with the anti-JJAZ1 antiserum in the JJAZ1myc extract either deleted the myc epitope or that the band represents non-specific immunoreactivity. Multiple specific bands are observed in the extracts from JAZF1myc expressing cells when probing with either the anti-JAZF1 antiserum or the anti-MYC antibody. The nature of the multiple species of the JAZF1myc protein is not known, but this finding suggests that the JAZF1 protein undergoes post-translational processing or rapid degradation.

Example 11

Analysis of Endometrial Stromal Tumors for the JAZF1/JJAZ1 Fusion Transcript

The Northern blot and RT-PCR analysis of four low-grade ESSs with the t(7;17) discussed above demonstrated the presence of the same JAZF1/JJAZ1 fusion. To examine the prevalence of this fusion in other cases of endometrial stromal tumors, RT-PCR was performed on four cases of LG-ESS for which cytogenetic analysis had not been carried out: one stromal nodule, six cases of high grade ESS, one case of undifferentiated uterine sarcoma, and ten samples of normal endometrium. In addition to these homogeneous stromal tumors, we examined 11 cases of malignant mixed müllerian tumor, two cases of endometrial adenosarcoma, and 11 cases of endometrial carcinoma to assess the possibility that the gene fusion occurs in tumors with an epithelial component or in tumors that were exclusively epithelial. RNA for these analyses was isolated from formalin-fixed, paraffin-embedded archival material. RT-PCR was performed using sense JAZF1 primers and antisense JJAZ1 primers. Extracted RNA from each case yielded amplifiable template as judged by the amplification of glyceraldehyde-3-phosphate dehydrogenase message. The results of the RT-PCR survey are summarized in Table 3.

TABLE 3

RT-PCR survey of endometrial stromal tumors for the presence of the JAZF1/JJAZ1 fusion transcript. The LG-ESS category includes the four cases with uncharacterized cytogenetics as well as the case LG-ESS-2 that corresponds to case BWH-665.

| Tumor Type | Positive Cases | Total Cases |
|---|---|---|
| Normal Endometrium | 0 | 10 |
| Stromal Nodule | 1 | 1 |
| Low grade ESS | 5 | 5 |
| High grade ESS | 2 | 6 |
| Undifferentiated Uterine Sarcoma | 1 | 1 |
| Endometrial Adenosarcoma | 1 | 2 |
| Malignant Mixed Müllerian Tumor | 6 | 11 |
| Endometrial Carcinoma | 0 | 11 |

Among the endometrial stromal sarcomas, all low-grade cases were positive for the fusion transcript; however, only two of six high-grade cases were positive. A single case of UUS was classified as positive. Among the cases with a mixed cellular phenotype, one of two cases of endometrial adenosarcoma and six of eleven cases of MMMT were classified as positive. None of the RNA samples extracted from normal endometrium or endometrial carcinoma were found to contain the fusion transcript.

Example 12

Analysis of Endometrial Stromal Tumors for Disruption of the JAZF1 Gene by Fluorescence in situ Hybridization.

The RT-PCR analysis suggested that a JAZF1/JJAZ1 fusion transcript is produced by a spectrum of endometrial stromal neoplasms. In order to verify this finding, we used FISH to analyze isolated nuclei from the same archival material. The case LG-ESS-2 (identical to case BWH-665) known to have the t(7;17)(p15;q21) was analyzed, as were the RT-PCR positive case of UUS, two cases of MMMT classified as negative by RT-PCR, and two cases of MMMT classified as positive by RT-PCR. A biotin labeled centromeric probe was generated from the DNA of BAC b319D14, a BAC clone that maps to the middle of the JAZF1 gene. A digoxigenin labeled telomeric probe was generated from the DNA of BAC b332C6, a BAC clone that maps approximately 60 kb telomeric of the JAZF1 gene. Hybridization was detected with fluorescein-conjugated avidin and rhodamine-conjugated anti-digoxigenin antibody, respectively. With these probes, a hybridization pattern consisting of one red-green signal pair, one unpaired red signal and one unpaired green signal is indicative of a simple disruption of the JAZF1 gene. A summary of the FISH results is presented in Table 4.

TABLE 4

FISH analysis of endometrial stromal tumors for the disruption of the JAZF1 gene.

| Case | RT-PCR Status | Percentage of Nuclei Positive |
|---|---|---|
| LG-ESS-2 | positive | 100% |
| UUS-1 | positive | 100% |
| MMMT-4 | negative | 0% |
| MMMT-5 | positive | ~5% |

TABLE 4-continued

FISH analysis of endometrial stromal tumors for the disruption of the JAZF1 gene.

| Case | RT-PCR Status | Percentage of Nuclei Positive |
| --- | --- | --- |
| MMMT-6 | negative | 0% |
| MMMT-8 | positive | ~5% |

In the cases LG-ESS-2 and UUS-1, the hybridization pattern consistent with the disruption of JAZF1 was seen in all nuclei for which fluorescent hybridization signal was discernible. These findings were consistent with the RT-PCR findings. In the MMMT cases analyzed by FISH, greater than two rhodamine signals were present in the majority of nuclei. In these cases the presence of two or more fluorescein signals, only one of which was paired with a rhodamine signal, was interpreted as an indication that the JAZF1 gene was disrupted. In the MMMT cases classified as negative by RT-PCR, MMMT-4 and MMMT-6, none of the nuclei analyzed by FISH showed a disruption in the JAZF1 gene. In the MMMT cases found by RT-PCR to produce the JAZF1/JJAZ1 fusion transcript, cases MMMT-5 and MMMT-8, the majority of the nuclei showed no alteration of the JAZF1 gene. However, a small fraction (~5%) of the nuclei did show a disruption in the JAZF1 gene. Several examples of a disrupted hybridization pattern from case MMMT-5 are presented in FIGS. 20F and 20G. A nucleus from this case that shows a hybridization pattern nearly identical to that seen with LG-ESS-2 except for the presence of an additional rhodamine signal is shown in FIG. 20F. FIG. 20G shows three nuclei from case MMMT-5. In both the upper left and lower nuclei, three fluorescein signals are present, and only one of these in each nucleus is paired with a rhodamine signal. The finding that the JAZF1 gene is disrupted in a small fraction of nuclei in some cases of MMMT is consistent with the possibility that a minority of the cells in these tumors may produce the JAZF1/JJAZ1 fusion transcript.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated JAZ polypeptide having a sequence that is identical to the amino acid sequence shown in SEQ ID NO:8.

* * * * *

SEQUENCE LISTING

```
<160> NUMBER OF SEQ ID NOS: 23

<210> SEQ ID NO 1
<211> LENGTH: 3010
<212> TYPE: DNA
<213> ORGANISM: Homo sapiens
<220> FEATURE:
<221> NAME/KEY: CDS
<222> LOCATION: (52)...(780)

<400> SEQUENCE: 1
cccgcccggc gctcgcagag ccgacaccag gggggctctc gatgtagcac c atg aca       57
                                                          Met Thr
                                                           1 ggc atc gcc gcc gcc tcc ttc ttc tcc aat acc tgc cga ttc ggg ggc      105
Gly Ile Ala Ala Ala Ser Phe Phe Ser Asn Thr Cys Arg Phe Gly Gly
        5                  10                  15 tgc gga ctc cac ttc ccc acc ctg gcc gac ctc atc gag cac atc gag      153
Cys Gly Leu His Phe Pro Thr Leu Ala Asp Leu Ile Glu His Ile Glu
    20                  25                  30 gac aac cac atc gat aca gat cca cgg gtt tta gaa aaa caa gaa tta      201
Asp Asn His Ile Asp Thr Asp Pro Arg Val Leu Glu Lys Gln Glu Leu
35                  40                  45                  50 cag cag cca acc tat gtt gcc ctg agt tac ata aat aga ttc atg aca      249
Gln Gln Pro Thr Tyr Val Ala Leu Ser Tyr Ile Asn Arg Phe Met Thr
                55                  60                  65 gat gct gcc cgc cga gag cag gag tcc cta aag aag aag att cag ccg      297
Asp Ala Ala Arg Arg Glu Gln Glu Ser Leu Lys Lys Lys Ile Gln Pro
            70                  75                  80 aag ctc tcg ctg act ctg tcc agc tca gtg tct cga ggg aat gtg tcc      345
Lys Leu Ser Leu Thr Leu Ser Ser Ser Val Ser Arg Gly Asn Val Ser
        85                  90                  95 act ccc cca cgc cac agc agt gga agc ctt act ccc ccc gtg acc cca      393
Thr Pro Pro Arg His Ser Ser Gly Ser Leu Thr Pro Pro Val Thr Pro
    100                 105                 110 ccc atc acc ccc tcc tct tca ttc cgc agc agc act ccg aca ggc agc      441
```

| | | |
|---|---|---|
| Pro Ile Thr Pro Ser Ser Ser Phe Arg Ser Ser Thr Pro Thr Gly Ser<br>115                            120                        125                        130 | |
| gag tat gac gag gag gag gtg gac tat gag gag tcg gac agc gat gag<br>Glu Tyr Asp Glu Glu Glu Val Asp Tyr Glu Glu Ser Asp Ser Asp Glu<br>                           135                        140                        145 | 489 |
| tcc tgg acc aca gag agt gcc atc agc tcc gaa gcc atc ctc agc tcc<br>Ser Trp Thr Thr Glu Ser Ala Ile Ser Ser Glu Ala Ile Leu Ser Ser<br>              150                        155                        160 | 537 |
| atg tgc atg aat gga ggg gaa gag aag cct ttt gcc tgc cca gtt cct<br>Met Cys Met Asn Gly Gly Glu Glu Lys Pro Phe Ala Cys Pro Val Pro<br>165                           170                        175 | 585 |
| gga tgt aaa aag aga tac aag aat gtg aat ggc ata aag tat cac gct<br>Gly Cys Lys Lys Arg Tyr Lys Asn Val Asn Gly Ile Lys Tyr His Ala<br>    180                        185                        190 | 633 |
| aag aat ggt cac aga aca cag att cgt gtc cgc aaa cca ttc aag tgt<br>Lys Asn Gly His Arg Thr Gln Ile Arg Val Arg Lys Pro Phe Lys Cys<br>195                           200                        205                        210 | 681 |
| cgc tgt ggg aag agt tac aag aca gct cag ggc ctg cgg cac cac aca<br>Arg Cys Gly Lys Ser Tyr Lys Thr Ala Gln Gly Leu Arg His His Thr<br>                           215                        220                        225 | 729 |
| atc aat ttc cat ccc ccg gtg tcg gct gag att atc agg aag atg cag<br>Ile Asn Phe His Pro Pro Val Ser Ala Glu Ile Ile Arg Lys Met Gln<br>            230                        235                        240 | 777 |
| caa taacatgctg gtcataactg tgccaagaaa tcctcaccag cagttgctga<br>Gln | 830 |
| ttttgaaaac agccaccttt ttcaggggga agcattcagc aacccttaa agaaaaagaa | 890 |
| ttaaatgcat gctttaaatt ttttctgtaa ttttggaatg atgtatcttt gtagagttaa | 950 |
| tgattttgta catttgcaca tgtaatcatc atacccattt tcattacttt gatataaggt | 1010 |
| gctaaacaaa aaaagctcta ggttcttcag cacatttccc ccaaaacaaa ataaaattga | 1070 |
| gggcatgttg catattgttg aattgtattg cggtggtatc aacctggggg gaggaggggc | 1130 |
| tggcactgag attttttttt caagattgta atgtgattga agttttcaac acatcaactc | 1190 |
| acatatgttc aaaccaaaaa taataccttc attatcaaac tggttaccat gccttacata | 1250 |
| atggagttag tatttgtgag tagaaagact ttaggtaatg gaaatataaa taagaaagaa | 1310 |
| tgtttaacat aatatgctaa aaatattttc atatttaaat aacatacgta aaggtgtgct | 1370 |
| ttctgtgttt tatattatct tgcaaatcct tttgcccttt aaaaagctga aaatcttgcc | 1430 |
| atctgactta ctagtcattt tagtgttata aatggcattt tgtacaaaat agtctattca | 1490 |
| gttcgttcat tcatttaaca cacattgatt gagtgcctgc tgggtacaag ggattcaatt | 1550 |
| tatgcctatt gatatctgcg gaccaagata cccatttagt gaaatacttt tttccctgaa | 1610 |
| atctgttaga aagactttg aaatacttca gtgcaaagtg tgtgtgtgtg aagtttagtt | 1670 |
| atatcttcat cttcagatga agttttaaag cactttgtag ttctctattg ccaacaattt | 1730 |
| aatgtttatg tgttgccaat tcttgcaacc actgccctac caaacctgtg ggttgcaaat | 1790 |
| cagaactaaa attctaagca cgtttcaaag atgaacactt tgttaagac ccctattgcc | 1850 |
| tcttcttcat gctcattttt tacttttttt aaaaggtact tttctcatca cattgtagag | 1910 |
| aggtctgcat tctcattgga aatgtctgtt tagctttata aaacaaacac tttgctgaaa | 1970 |
| taggaaaatg agccttattg acaattaagt gcttcttgca gcaggtggtc aaagaaaagc | 2030 |
| atgactaata cgacctatta gagtaatcta catctggacc attccttaag tttttcctca | 2090 |
| ccgacagtac catcatgcct tgagtgttct tttctcccaa gtgctattcc ttaaacacga | 2150 |
| gagtttacca gttgcctaat aatgcaataa aaaatgcttt gagatagcta actgcccata | 2210 |

-continued

```
aaacaaactc aaattgctta taaagtttct tcccatgttc ccatttgatg aaaagtctta    2270
catcacatat aactgggaag caggggtccc tcctcaattt tcagacattt tgaaaggatg    2330
acagttctgt tgttagatg agtaaacctc tatattcata agttctaaaa tccttcatta    2390
tgagggattc aaagtattta taaaaacact gccctctaaa aatttcctca gatctgaagt    2450
atggtcttgg tcctgaatat acagtgttat cctatgttta aaagggtgat ccagacatga    2510
gacgcaacta gttggtgcat aagaaggccc cacttggcta tttcatatct acctacaatt    2570
gaccaaaaaa aatttttttag gccagcaatt attatttagc ttcgctcttt ctagtgcaag    2630
aaactgcagg ctggatcagt agttcaacag ctaaacagtc ataaaatagt cattgtgcat    2690
gttaaatttc tttcaatgct ttcaaagata aattccaatt tctatttact tattcattgt    2750
gacagtatta ctaaacaggt aaggatggga atattttgtt atactgtgta tagtgaatgt    2810
attgtactgt gtctgtgaaa actgtgcttt aaattatatt ttcatatgtt ttgttgggga    2870
cagagcacat taagtctgaa agcaacagag gtttgtttta gaactgaagg caatttaatc    2930
aaaattcctg tcaagaaaag ctgcttataa atgtaaatga aatcacattt aaaataaact    2990
gcctctgacc caaaaataaa                                                3010
```

<210> SEQ ID NO 2
<211> LENGTH: 243
<212> TYPE: PRT
<213> ORGANISM: Homo sapiens

<400> SEQUENCE: 2

```
Met Thr Gly Ile Ala Ala Ala Ser Phe Phe Ser Asn Thr Cys Arg Phe
  1               5                  10                  15

Gly Gly Cys Gly Leu His Phe Pro Thr Leu Ala Asp Leu Ile Glu His
                 20                  25                  30

Ile Glu Asp Asn His Ile Asp Thr Asp Pro Arg Val Leu Glu Lys Gln
             35                  40                  45

Glu Leu Gln Gln Pro Thr Tyr Val Ala Leu Ser Tyr Ile Asn Arg Phe
         50                  55                  60

Met Thr Asp Ala Ala Arg Arg Glu Gln Glu Ser Leu Lys Lys Lys Ile
 65                  70                  75                  80

Gln Pro Lys Leu Ser Leu Thr Leu Ser Ser Ser Val Ser Arg Gly Asn
                 85                  90                  95

Val Ser Thr Pro Pro Arg His Ser Ser Gly Ser Leu Thr Pro Pro Val
                100                 105                 110

Thr Pro Pro Ile Thr Pro Ser Ser Phe Arg Ser Ser Thr Pro Thr
            115                 120                 125

Gly Ser Glu Tyr Asp Glu Glu Glu Val Asp Tyr Glu Glu Ser Asp Ser
        130                 135                 140

Asp Glu Ser Trp Thr Thr Glu Ser Ala Ile Ser Ser Glu Ala Ile Leu
145                 150                 155                 160

Ser Ser Met Cys Met Asn Gly Glu Glu Lys Pro Phe Ala Cys Pro
                165                 170                 175

Val Pro Gly Cys Lys Lys Arg Tyr Lys Asn Val Asn Gly Ile Lys Tyr
                180                 185                 190

His Ala Lys Asn Gly His Arg Thr Gln Ile Arg Val Lys Pro Phe
            195                 200                 205

Lys Cys Arg Cys Gly Lys Ser Tyr Lys Thr Ala Gln Gly Leu Arg His
        210                 215                 220
```

His Thr Ile Asn Phe His Pro Pro Val Ser Ala Glu Ile Ile Arg Lys
225                 230                 235                 240

Met Gln Gln

<210> SEQ ID NO 3
<211> LENGTH: 729
<212> TYPE: DNA
<213> ORGANISM: Homo sapiens

<400> SEQUENCE: 3

```
atgacaggca tcgccgccgc ctccttcttc tccaatacct gccgattcgg gggctgcgga      60
ctccacttcc ccaccctggc cgacctcatc gagcacatcg aggacaacca catcgataca     120
gatccacggg ttttagaaaa acaagaatta cagcagccaa cctatgttgc cctgagttac     180
ataaatagat tcatgacaga tgctgcccgc cgagagcagg agtccctaaa gaagaagatt     240
cagccgaagc tctcgctgac tctgtccagc tcagtgtctc gagggaatgt gtccactccc     300
ccacgccaca gcagtggaag ccttactccc cccgtgaccc cacccatcac cccctcctct     360
tcattccgca gcagcactcc gacaggcagc gagtatgacg aggaggaggt ggactatgag     420
gagtcggaca gcgatgagtc ctggaccaca gagagtgcca tcagctccga agccatcctc     480
agctccatgt gcatgaatgg agggaagag aagccttttg cctgcccagt tcctggatgt     540
aaaaagagat acaagaatgt gaatggcata agtatcacgc taagaatgg tcacagaaca     600
cagattcgtg tccgcaaacc attcaagtgt cgctgtggga agagttacaa gacagctcag     660
ggcctgcggc accacacaat caatttccat ccccggtgt cggctgagat tatcaggaag     720
atgcagcaa                                                            729
```

<210> SEQ ID NO 4
<211> LENGTH: 4441
<212> TYPE: DNA
<213> ORGANISM: Homo sapiens
<220> FEATURE:
<221> NAME/KEY: CDS
<222> LOCATION: (195)...(2411)

<400> SEQUENCE: 4

```
ctctgaggag acactttttt tttcctccct ccttccctcc tctcctcctc ccttcccttc      60
ccctctcctc ccctctctcc tccttccccc ctcggtccgc cggagcctgc tggggcgagc     120
ggttggtatt gcaggcgctt gctctccggg gccgcccggc gggtagctgg cggggggagg     180
```

```
aggcaggaac cgcg atg gcg cct cag aag cac ggc ggt ggg gga ggg ggc       230
         Met Ala Pro Gln Lys His Gly Gly Gly Gly Gly Gly
           1               5                  10 ggc tcg ggg ccc agc gcg ggg tcc ggg gga ggc ggc ttc ggg ggt tcg       278
Gly Ser Gly Pro Ser Ala Gly Ser Gly Gly Gly Gly Phe Gly Gly Ser
        15                  20                  25 gcg gcg gtg gcg gcg gcg acg gct tcg ggc ggc aaa tcc ggc ggc ggg       326
Ala Ala Val Ala Ala Ala Thr Ala Ser Gly Gly Lys Ser Gly Gly Gly
    30                  35                  40 agc tgt gga ggg ggt ggc agt tac tcg gcc tcc tcc tcc tcc gcg           374
Ser Cys Gly Gly Gly Gly Ser Tyr Ser Ala Ser Ser Ser Ser Ser Ala
45                  50                  55                  60 gcg gca gcg gcg ggg gct gcg gtg tta ccg gtg aag aag ccg aaa atg       422
Ala Ala Ala Ala Gly Ala Ala Val Leu Pro Val Lys Lys Pro Lys Met
                65                  70                  75 gag cac gtc cag gct gac cac gag ctt ttc ctc cag gcc ttt gag aag       470
Glu His Val Gln Ala Asp His Glu Leu Phe Leu Gln Ala Phe Glu Lys
            80                  85                  90
```

-continued

| | |
|---|---|
| cca aca cag atc tat aga ttt ctt cga act cgg aat ctc ata gca cca<br>Pro Thr Gln Ile Tyr Arg Phe Leu Arg Thr Arg Asn Leu Ile Ala Pro<br>        95                       100                    105 | 518 |
| ata ttt ttg cac aga act ctt act tac atg tct cat cga aac tcc aga<br>Ile Phe Leu His Arg Thr Leu Thr Tyr Met Ser His Arg Asn Ser Arg<br>110                        115                    120 | 566 |
| aca aac atc aaa agg aaa aca ttt aaa gtt gat gat atg tta tca aaa<br>Thr Asn Ile Lys Arg Lys Thr Phe Lys Val Asp Asp Met Leu Ser Lys<br>125                   130                    135                140 | 614 |
| gta gag aaa atg aaa gga gag caa gaa tct cat agc ttg tca gct cat<br>Val Glu Lys Met Lys Gly Glu Gln Glu Ser His Ser Leu Ser Ala His<br>              145                    150                    155 | 662 |
| ttg cag ctt acg ttt act ggt ttc ttc cac aaa aat gat aag cca tca<br>Leu Gln Leu Thr Phe Thr Gly Phe Phe His Lys Asn Asp Lys Pro Ser<br>             160                    165                    170 | 710 |
| cca aac tca gaa aat gaa caa aat tct gtt acc ctg gaa gtc ctg ctt<br>Pro Asn Ser Glu Asn Glu Gln Asn Ser Val Thr Leu Glu Val Leu Leu<br>175                       180                    185 | 758 |
| gtg aaa gtt tgc cac aaa aaa aga aag gat gta agt tgt cca ata agg<br>Val Lys Val Cys His Lys Lys Arg Lys Asp Val Ser Cys Pro Ile Arg<br>              190                    195                    200 | 806 |
| caa gtt ccc aca ggt aaa aag cag gtg cct ttg att cct gac ctc aat<br>Gln Val Pro Thr Gly Lys Lys Gln Val Pro Leu Ile Pro Asp Leu Asn<br>205                       210                    215                220 | 854 |
| caa aca aaa ccc gga aat ttc ccg tcc ctt gca gtt tcc agt aat gaa<br>Gln Thr Lys Pro Gly Asn Phe Pro Ser Leu Ala Val Ser Ser Asn Glu<br>                       225                    230                    235 | 902 |
| ttt gaa cct agt aac agc cat atg gtg aag tct tac tcg ttg cta ttt<br>Phe Glu Pro Ser Asn Ser His Met Val Lys Ser Tyr Ser Leu Leu Phe<br>              240                    245                    250 | 950 |
| aga gtg act cgt cca gga aga aga gag ttt aat gga atg att aat gga<br>Arg Val Thr Arg Pro Gly Arg Arg Glu Phe Asn Gly Met Ile Asn Gly<br>                  255                    260                    265 | 998 |
| gaa acc aat gaa aat att gat gtc aat gaa gag ctt cca gcc aga aga<br>Glu Thr Asn Glu Asn Ile Asp Val Asn Glu Glu Leu Pro Ala Arg Arg<br>          270                    275                    280 | 1046 |
| aaa cga aat cgt gag gat ggg gaa aag aca ttt gtt gca caa atg aca<br>Lys Arg Asn Arg Glu Asp Gly Glu Lys Thr Phe Val Ala Gln Met Thr<br>285                       290                    295                300 | 1094 |
| gta ttt gat aaa aac agg cgc tta cag ctt tta gat ggg gaa tat gaa<br>Val Phe Asp Lys Asn Arg Arg Leu Gln Leu Leu Asp Gly Glu Tyr Glu<br>                      305                    310                    315 | 1142 |
| gta gcc atg cag gaa atg gaa gaa tgt cca ata agc aag aaa aga gca<br>Val Ala Met Gln Glu Met Glu Glu Cys Pro Ile Ser Lys Lys Arg Ala<br>                    320                    325                    330 | 1190 |
| aca tgg gag act att ctt gat ggg aag agg ctg cct cca ttc gaa aca<br>Thr Trp Glu Thr Ile Leu Asp Gly Lys Arg Leu Pro Pro Phe Glu Thr<br>              335                    340                    345 | 1238 |
| ttt tct cag gga cct acg ttg cag ttc act ctt cgt tgg aca gga gag<br>Phe Ser Gln Gly Pro Thr Leu Gln Phe Thr Leu Arg Trp Thr Gly Glu<br>350                       355                    360 | 1286 |
| acc aat gat aaa tct acg gct cct att gcc aaa cct ctt gcc act aga<br>Thr Asn Asp Lys Ser Thr Ala Pro Ile Ala Lys Pro Leu Ala Thr Arg<br>365                       370                    375                380 | 1334 |
| aat tca gag agt ctc cat cag gaa aac aag cct ggt tca gtt aaa cct<br>Asn Ser Glu Ser Leu His Gln Glu Asn Lys Pro Gly Ser Val Lys Pro<br>                    385                    390                    395 | 1382 |
| act caa act att gct gtt aaa gaa tca ttg act aca gat cta caa aca<br>Thr Gln Thr Ile Ala Val Lys Glu Ser Leu Thr Thr Asp Leu Gln Thr | 1430 |

-continued

```
                     400                 405                 410
aga aaa gaa aag gat act cca aat gaa aac cga caa aaa tta aga ata       1478
Arg Lys Glu Lys Asp Thr Pro Asn Glu Asn Arg Gln Lys Leu Arg Ile
            415                 420                 425 ttt tat cag ttt ctc tat aac aac aat aca agg caa caa act gaa gca       1526
Phe Tyr Gln Phe Leu Tyr Asn Asn Asn Thr Arg Gln Gln Thr Glu Ala
430                 435                 440 aga gat gac ctg cat tgc cct tgg tgt act ctg aac tgc cgc aaa ctt       1574
Arg Asp Asp Leu His Cys Pro Trp Cys Thr Leu Asn Cys Arg Lys Leu
445                 450                 455                 460 tat agt tta ctc aag cat ctt aaa ctc tgc cat agc aga ttt atc ttc       1622
Tyr Ser Leu Leu Lys His Leu Lys Leu Cys His Ser Arg Phe Ile Phe
            465                 470                 475 aac tat gtt tat cat cca aaa ggt gct agg ata gat gtt tct atc aat       1670
Asn Tyr Val Tyr His Pro Lys Gly Ala Arg Ile Asp Val Ser Ile Asn
            480                 485                 490 gag tgt tat gat ggc tcc tat gca gga aat cct cag gat att cat cgc       1718
Glu Cys Tyr Asp Gly Ser Tyr Ala Gly Asn Pro Gln Asp Ile His Arg
            495                 500                 505 caa cct gga ttt gct ttt agt cgc aac gga cca gtt aag aga aca cct       1766
Gln Pro Gly Phe Ala Phe Ser Arg Asn Gly Pro Val Lys Arg Thr Pro
510                 515                 520 atc aca cat att ctt gtg tgc agg cca aaa cga aca aaa gca agc atg       1814
Ile Thr His Ile Leu Val Cys Arg Pro Lys Arg Thr Lys Ala Ser Met
525                 530                 535                 540 tct gaa ttt ctt gaa tct gaa gat ggg gaa gta gaa cag caa aga aca       1862
Ser Glu Phe Leu Glu Ser Glu Asp Gly Glu Val Glu Gln Gln Arg Thr
            545                 550                 555 tat agt agt ggc cac aat cgt ctg tat ttc cat agt gat acc tgc tta       1910
Tyr Ser Ser Gly His Asn Arg Leu Tyr Phe His Ser Asp Thr Cys Leu
            560                 565                 570 cct ctc cgt cca caa gaa atg gaa gta gat agt gaa gat gaa aag gat       1958
Pro Leu Arg Pro Gln Glu Met Glu Val Asp Ser Glu Asp Glu Lys Asp
            575                 580                 585 cct gaa tgg cta aga gaa aaa acc att aca caa att gaa gag ttt tct       2006
Pro Glu Trp Leu Arg Glu Lys Thr Ile Thr Gln Ile Glu Glu Phe Ser
590                 595                 600 gat gtt aat gaa gga gag aaa gaa gtg atg aaa ctc tgg aat ctc cat       2054
Asp Val Asn Glu Gly Glu Lys Glu Val Met Lys Leu Trp Asn Leu His
605                 610                 615                 620 gtc atg aag cat ggg ttt att gct gac aat caa atg aat cat gcc tgt       2102
Val Met Lys His Gly Phe Ile Ala Asp Asn Gln Met Asn His Ala Cys
            625                 630                 635 atg ctg ttt gta gaa aat tat gga cag aaa ata att aag aag aat tta       2150
Met Leu Phe Val Glu Asn Tyr Gly Gln Lys Ile Ile Lys Lys Asn Leu
            640                 645                 650 tgt cga aac ttc atg ctt cat cta gtc agc atg cat gac ttt aat ctt       2198
Cys Arg Asn Phe Met Leu His Leu Val Ser Met His Asp Phe Asn Leu
            655                 660                 665 att agc ata atg tca ata gat aaa gct gtt acc aag ctc cgt gaa atg       2246
Ile Ser Ile Met Ser Ile Asp Lys Ala Val Thr Lys Leu Arg Glu Met
670                 675                 680 cag caa aaa tta gaa aag ggg gaa tct gct tcc cct gca aac gaa gaa       2294
Gln Gln Lys Leu Glu Lys Gly Glu Ser Ala Ser Pro Ala Asn Glu Glu
685                 690                 695                 700 ata act gaa gaa caa aat ggg aca gca aat gga ttt agt gaa att aac       2342
Ile Thr Glu Glu Gln Asn Gly Thr Ala Asn Gly Phe Ser Glu Ile Asn
            705                 710                 715 tca aaa gag aaa gct ttg gaa aca gat agt gtc tca ggg gtt tca aaa       2390
```

```
Ser Lys Glu Lys Ala Leu Glu Thr Asp Ser Val Ser Gly Val Ser Lys
                720                 725                 730 cag agc aaa aaa caa aaa ctc tgaaaagctc taaccccatg ttatggacaa       2441
Gln Ser Lys Lys Gln Lys Leu
        735 acactgaaat tacattttag ggaattcatc ctctaagaat tatgtttttg tttttaatca   2501 tatgttccaa acaggcactg ttagatgaag taaatgattt caacaaggat atttgtatca   2561 gggttctact tcacttcatt atgcagcatt acatgtatat cactttttatt gatgtcatta  2621 aaacattctg tactttaagc atgaaaagca atatttcaaa gtattttttaa actcaacaaa  2681 tgtcatcaaa tatgttgaat tgatctagaa attatttcat atataaatca gattttttt    2741 gcatttatga acggctgttt ttctactttg taattgtgag acattttctt ggggagggaa   2801 aattggaatg gttccctttt ttagaaattg aagtggtctt catatgtcaa ctacagaaaa   2861 ggaaaaaaat agaaattgaa ggatttttat gaaattatat tgcattacta tttgcagtca   2921 aactttgatc cttgttttttg aaatcatttg tcaattcgga atgaaaaatt ataatgtaat  2981 tttacattac ataagttcct tttacaatta aaaaatagca cttcttcatc ttatgcctgt   3041 ttgagaagat attaaatttt cacattgttg acagtgaaat gctatgttgg tttataagat   3101 tacagaccat ttgtttttcat gtggataatt ttagtgcatt gctcacccgg tatgttttttt 3161 tttttttaact tgaacatttt gcttgttttg tttttctttt taattagat aatcacacgg   3221 aaaattaagc tgttcatatc tttaaattag gattgcaaac caaggaaaga acgcatttga   3281 gattttaaga tgtcacttat aagggagaa gtgttcttaa aaagtcaacc agaaaactgt    3341 tatgcctttt atttgtttgc aaggatgtct ttgtaatgtg tttcatgaat agaatatcca   3401 atagagataa gctgacttga atcattttga gcaattttgc cctgtgttat atgtgtttca   3461 cgcacatatt tgcagttgga ttttctccaa cagaaagtgg attcactact ggcacattaa   3521 caagcaccaa taggttttta ttccaactcc gagcactgtg gttgagtaac atcacctcaa   3581 tttttttatta tccttaaaga tattgcattt tcatattctt tatttataaa ggatcaatgc  3641 tgctgtaaat acaggtattt ttaatttttaa aatttcattc caccaccatc agatgcagtt  3701 ccctatttttg tttaatgaag ggatatataa gctttctaat ggtgtcttca gaaatttata  3761 aaatgtaaat actgatttga ctggtctttta agatgtgttt aactgtgagg ctatttaacg   3821 aatagtgtgg atgtgatttg tcatccagta ttaagttctt agtcattgat ttttgtgttt   3881 aaaaaaaaat aggaaagagg gaaactgcag ctttcattac agattccttg attggtaagc   3941 tctccaaatg atgagttcta gtaaactctg atttttgcct ctggatagta gatctcgagc   4001 gtttatctcg ggctttaatt tgctaaagct gtgcacatat gtaaaaaaaa aaaaaaaaag   4061 attatttttag gggagatgta ggtgtagaat tattgcttat gtcatttctt aagcagttat   4121 gctcttaatg cttaaaagaa ggctagcatt gtttgcacaa aaagttggtg attcccaccc   4181 caaatagtaa taaaattact tctgttgagt aaacttttta tgtcatcgta aaagctggaa   4241 aaatcccttt gtttctattt ataaaaaaag tgcttttcta tatgtaccct tgataacaga   4301 ttttgaagaa atcctgtaag atgataaagc atttgaatgg tacagtagat gtaaaaaaaa   4361 ttcagtttaa aagaacatttt gttttttacat taaatgtttta tttgaaatca aatgattttg   4421 tacataaagt tcaataatat                                               4441

<210> SEQ ID NO 5
<211> LENGTH: 739
<212> TYPE: PRT
```

<213> ORGANISM: Homo sapiens

<400> SEQUENCE: 5

```
Met Ala Pro Gln Lys His Gly Gly Gly Gly Gly Ser Gly Pro
  1               5                  10                  15
Ser Ala Gly Ser Gly Gly Gly Phe Gly Gly Ser Ala Ala Val Ala
                 20                  25                  30
Ala Ala Thr Ala Ser Gly Gly Lys Ser Gly Gly Ser Cys Gly Gly
                 35                  40                  45
Gly Gly Ser Tyr Ser Ala Ser Ser Ser Ser Ala Ala Ala Ala
 50                  55                  60
Gly Ala Ala Val Leu Pro Val Lys Lys Pro Lys Met Glu His Val Gln
 65                  70                  75                  80
Ala Asp His Glu Leu Phe Leu Gln Ala Phe Glu Lys Pro Thr Gln Ile
                 85                  90                  95
Tyr Arg Phe Leu Arg Thr Arg Asn Leu Ile Ala Pro Ile Phe Leu His
                100                 105                 110
Arg Thr Leu Thr Tyr Met Ser His Arg Asn Ser Arg Thr Asn Ile Lys
                115                 120                 125
Arg Lys Thr Phe Lys Val Asp Asp Met Leu Ser Lys Val Glu Lys Met
                130                 135                 140
Lys Gly Glu Gln Glu Ser His Ser Leu Ser Ala His Leu Gln Leu Thr
145                 150                 155                 160
Phe Thr Gly Phe Phe His Lys Asn Asp Lys Pro Ser Pro Asn Ser Glu
                165                 170                 175
Asn Glu Gln Asn Ser Val Thr Leu Glu Val Leu Leu Val Lys Val Cys
                180                 185                 190
His Lys Lys Arg Lys Asp Val Ser Cys Pro Ile Arg Gln Val Pro Thr
                195                 200                 205
Gly Lys Lys Gln Val Pro Leu Ile Pro Asp Leu Asn Gln Thr Lys Pro
                210                 215                 220
Gly Asn Phe Pro Ser Leu Ala Val Ser Ser Asn Glu Phe Glu Pro Ser
225                 230                 235                 240
Asn Ser His Met Val Lys Ser Tyr Ser Leu Leu Phe Arg Val Thr Arg
                245                 250                 255
Pro Gly Arg Arg Glu Phe Asn Gly Met Ile Asn Gly Glu Thr Asn Glu
                260                 265                 270
Asn Ile Asp Val Asn Glu Glu Leu Pro Ala Arg Arg Lys Arg Asn Arg
                275                 280                 285
Glu Asp Gly Glu Lys Thr Phe Val Ala Gln Met Thr Val Phe Asp Lys
290                 295                 300
Asn Arg Arg Leu Gln Leu Leu Asp Gly Glu Tyr Glu Val Ala Met Gln
305                 310                 315                 320
Glu Met Glu Glu Cys Pro Ile Ser Lys Lys Arg Ala Thr Trp Glu Thr
                325                 330                 335
Ile Leu Asp Gly Lys Arg Leu Pro Pro Phe Glu Thr Phe Ser Gln Gly
                340                 345                 350
Pro Thr Leu Gln Phe Thr Leu Arg Trp Thr Gly Glu Thr Asn Asp Lys
                355                 360                 365
Ser Thr Ala Pro Ile Ala Lys Pro Leu Ala Thr Arg Asn Ser Glu Ser
                370                 375                 380
Leu His Gln Glu Asn Lys Pro Gly Ser Val Lys Pro Thr Gln Thr Ile
385                 390                 395                 400
```

-continued

```
Ala Val Lys Glu Ser Leu Thr Thr Asp Leu Gln Thr Arg Lys Glu Lys
            405                 410                 415
Asp Thr Pro Asn Glu Asn Arg Gln Lys Leu Arg Ile Phe Tyr Gln Phe
        420                 425                 430
Leu Tyr Asn Asn Thr Arg Gln Gln Thr Glu Ala Arg Asp Asp Leu
    435                 440                 445
His Cys Pro Trp Cys Thr Leu Asn Cys Arg Lys Leu Tyr Ser Leu Leu
450                 455                 460
Lys His Leu Lys Leu Cys His Ser Arg Phe Ile Phe Asn Tyr Val Tyr
465                 470                 475                 480
His Pro Lys Gly Ala Arg Ile Asp Val Ser Ile Asn Glu Cys Tyr Asp
                485                 490                 495
Gly Ser Tyr Ala Gly Asn Pro Gln Asp Ile His Arg Gln Pro Gly Phe
            500                 505                 510
Ala Phe Ser Arg Asn Gly Pro Val Lys Arg Thr Pro Ile Thr His Ile
        515                 520                 525
Leu Val Cys Arg Pro Lys Arg Thr Lys Ala Ser Met Ser Glu Phe Leu
    530                 535                 540
Glu Ser Glu Asp Gly Glu Val Glu Gln Gln Arg Thr Tyr Ser Ser Gly
545                 550                 555                 560
His Asn Arg Leu Tyr Phe His Ser Asp Thr Cys Leu Pro Leu Arg Pro
                565                 570                 575
Gln Glu Met Glu Val Asp Ser Glu Asp Glu Lys Asp Pro Glu Trp Leu
            580                 585                 590
Arg Glu Lys Thr Ile Thr Gln Ile Glu Glu Phe Ser Asp Val Asn Glu
        595                 600                 605
Gly Glu Lys Glu Val Met Lys Leu Trp Asn Leu His Val Met Lys His
    610                 615                 620
Gly Phe Ile Ala Asp Asn Gln Met Asn His Ala Cys Met Leu Phe Val
625                 630                 635                 640
Glu Asn Tyr Gly Gln Lys Ile Ile Lys Lys Asn Leu Cys Arg Asn Phe
                645                 650                 655
Met Leu His Leu Val Ser Met His Asp Phe Asn Leu Ile Ser Ile Met
            660                 665                 670
Ser Ile Asp Lys Ala Val Thr Lys Leu Arg Glu Met Gln Gln Lys Leu
        675                 680                 685
Glu Lys Gly Glu Ser Ala Ser Pro Ala Asn Glu Glu Ile Thr Glu Glu
    690                 695                 700
Gln Asn Gly Thr Ala Asn Gly Phe Ser Glu Ile Asn Ser Lys Glu Lys
705                 710                 715                 720
Ala Leu Glu Thr Asp Ser Val Ser Gly Val Ser Lys Gln Ser Lys Lys
                725                 730                 735
Gln Lys Leu
```

<210> SEQ ID NO 6
<211> LENGTH: 2217
<212> TYPE: DNA
<213> ORGANISM: Homo sapiens

<400> SEQUENCE: 6

```
atggcgcctc agaagcacgg cggtggggga gggggcggct cggggcccag cgcggggtcc    60
gggggaggcg gcttcggggg ttcggcggcg gtggcggcgg cgacggcttc gggcggcaaa   120
tccggcggcg ggagctgtgg aggggtggc agttactcgg cctcctcctc ctcctccgcg   180
```

```
gcggcagcgg cggggggctgc ggtgttaccg gtgaagaagc cgaaaatgga gcacgtccag      240
gctgaccacg agcttttcct ccaggccttt gagaagccaa cacagatcta tagatttctt      300
cgaactcgga atctcatagc accaatattt ttgcacagaa ctcttactta catgtctcat      360
cgaaactcca gaacaaacat caaaaggaaa acatttaaag ttgatgatat gttatcaaaa      420
gtagagaaaa tgaaggaga gcaagaatct catagcttgt cagctcattt gcagcttacg       480
tttactggtt tcttccacaa aaatgataag ccatcaccaa actcagaaaa tgaacaaaat      540
tctgttaccc tggaagtcct gcttgtgaaa gtttgccaca aaaaagaaa ggatgtaagt       600 tgtccaataa ggcaagttcc cacaggtaaa aagcaggtgc ctttgattcc tgacctcaat      660
caaacaaaac ccggaaattt cccgtcccett gcagtttcca gtaatgaatt tgaacctagt      720
aacagccata tggtgaagtc ttactcgttg ctatttagag tgactcgtcc aggaagaaga      780
gagtttaatg gaatgattaa tggagaaacc aatgaaaata ttgatgtcaa tgaagagctt      840
ccagccagaa gaaaacgaaa tcgtgaggat ggggaaaaga catttgttgc acaaatgaca      900
gtatttgata aaaacaggcg cttacagctt ttagatgggg aatatgaagt agccatgcag      960
gaaatggaag aatgtccaat aagcaagaaa agagcaacat gggagactat tcttgatggg     1020
aagaggctgc ctccattcga acatttttct cagggaccta cgttgcagtt cactcttcgt     1080
tggacaggag agaccaatga taaatctacg gctcctattg ccaaacctct tgccactaga     1140
aattcagaga gtctccatca ggaaaacaag cctggttcag ttaaacctac tcaaactatt     1200
gctgttaaag aatcattgac tacagatcta caaacaagaa aagaaaagga tactccaaat     1260
gaaaaccgac aaaaattaag aatattttat cagtttctct ataacaacaa tacaaggcaa     1320
caaactgaag caagagatga cctgcattgc ccttggtgta ctctgaactg ccgcaaactt     1380
tatagtttac tcaagcatct taaactctgc catagcagat ttatcttcaa ctatgtttat     1440
catccaaaag gtgctaggat agatgtttct atcaatgagt gttatgatgg ctcctatgca     1500
ggaaatcctc aggatattca tcgccaacct ggatttgctt ttagtcgcaa cggaccagtt     1560
aagagaacac ctatcacaca tattcttgtg tgcaggccaa aacgaacaaa agcaagcatg     1620
tctgaatttc ttgaatctga agatggggaa gtagaacagc aaagaacata tagtagtggc     1680
cacaatcgtc tgtatttcca tagtgatacc tgcttacctc tccgtccaca agaaatggaa     1740
gtagatagtg aagatgaaaa ggatcctgaa tggctaagag aaaaaaccat tacacaaatt     1800 gaagagttttt ctgatgttaa tgaaggagag aaagaagtga tgaaactctg gaatctccat     1860
gtcatgaagc atgggtttat tgctgacaat caaatgaatc atgcctgtat gctgtttgta     1920
gaaaattatg gacagaaaat aattaagaag aatttatgtc gaaacttcat gcttcatcta     1980
gtcagcatgc atgactttaa tcttattagc ataatgtcaa tagataaagc tgttaccaag     2040
ctccgtgaaa tgcagcaaaa attagaaaag ggggaatctg cttcccctgc aaacgaagaa     2100
ataactgaag aacaaaatgg gacagcaaat ggatttagtg aaattaactc aaaagagaaa     2160
gctttggaaa cagatagtgt ctcaggggtt tcaaaacaga gcaaaaaaca aaaactc       2217
```

<210> SEQ ID NO 7
<211> LENGTH: 4409
<212> TYPE: DNA
<213> ORGANISM: Homo sapiens
<220> FEATURE:
<221> NAME/KEY: CDS
<222> LOCATION: (52)...(2379)

<400> SEQUENCE: 7

```
                                                                              -continued
cccgcccggc gctcgcagag ccgacaccag gggggctctc gatgtagcac c atg aca               57
                                                           Met Thr
                                                             1 ggc atc gcc gcc gcc tcc ttc ttc tcc aat acc tgc cga ttc ggg ggc               105
Gly Ile Ala Ala Ala Ser Phe Phe Ser Asn Thr Cys Arg Phe Gly Gly
         5                  10                  15 tgc gga ctc cac ttc ccc acc ctg gcc gac ctc atc gag cac atc gag               153
Cys Gly Leu His Phe Pro Thr Leu Ala Asp Leu Ile Glu His Ile Glu
     20                  25                  30 gac aac cac atc gat aca gat cca cgg gtt tta gaa aaa caa gaa tta               201
Asp Asn His Ile Asp Thr Asp Pro Arg Val Leu Glu Lys Gln Glu Leu
 35                  40                  45                  50 cag cag cca acc tat gtt gcc ctg agt tac ata aat aga ttc atg aca               249
Gln Gln Pro Thr Tyr Val Ala Leu Ser Tyr Ile Asn Arg Phe Met Thr
             55                  60                  65 gat gct gcc cgc cga gag cag gag tcc cta aag aag aag att cag ccg               297
Asp Ala Ala Arg Arg Glu Gln Glu Ser Leu Lys Lys Lys Ile Gln Pro
         70                  75                  80 aag ctc tcg ctg act ctg tcc agc tca gtg tct cga ggg aat gtg tcc               345
Lys Leu Ser Leu Thr Leu Ser Ser Ser Val Ser Arg Gly Asn Val Ser
     85                  90                  95 act ccc cca cgc cac agc agt gga agc ctt act ccc ccc gtg acc cca               393
Thr Pro Pro Arg His Ser Ser Gly Ser Leu Thr Pro Pro Val Thr Pro
100                 105                 110 ccc atc acc ccc tcc tct tca ttc cgc agc agc act ccg aca gag cca               441
Pro Ile Thr Pro Ser Ser Ser Phe Arg Ser Ser Thr Pro Thr Glu Pro
115                 120                 125                 130 aca cag atc tat aga ttt ctt cga act cgg aat ctc ata gca cca ata               489
Thr Gln Ile Tyr Arg Phe Leu Arg Thr Arg Asn Leu Ile Ala Pro Ile
             135                 140                 145 ttt ttg cac aga act ctt act tac atg tct cat cga aac tcc aga aca               537
Phe Leu His Arg Thr Leu Thr Tyr Met Ser His Arg Asn Ser Arg Thr
         150                 155                 160 aac atc aaa agg aaa aca ttt aaa gtt gat gat atg tta tca aaa gta               585
Asn Ile Lys Arg Lys Thr Phe Lys Val Asp Asp Met Leu Ser Lys Val
     165                 170                 175 gag aaa atg aaa gga gag caa gaa tct cat agc ttg tca gct cat ttg               633
Glu Lys Met Lys Gly Glu Gln Glu Ser His Ser Leu Ser Ala His Leu
180                 185                 190 cag ctt acg ttt act ggt ttc ttc cac aaa aat gat aag cca tca cca               681
Gln Leu Thr Phe Thr Gly Phe Phe His Lys Asn Asp Lys Pro Ser Pro
195                 200                 205                 210 aac tca gaa aat gaa caa aat tct gtt acc ctg gaa gtc ctg ctt gtg               729
Asn Ser Glu Asn Glu Gln Asn Ser Val Thr Leu Glu Val Leu Leu Val
             215                 220                 225 aaa gtt tgc cac aaa aaa aga aag gat gta agt tgt cca ata agg caa               777
Lys Val Cys His Lys Lys Arg Lys Asp Val Ser Cys Pro Ile Arg Gln
         230                 235                 240 gtt ccc aca ggt aaa aag cag gtg cct ttg att cct gac ctc aat caa               825
Val Pro Thr Gly Lys Lys Gln Val Pro Leu Ile Pro Asp Leu Asn Gln
     245                 250                 255 aca aaa ccc gga aat ttc ccg tcc ctt gca gtt tcc agt aat gaa ttt               873
Thr Lys Pro Gly Asn Phe Pro Ser Leu Ala Val Ser Ser Asn Glu Phe
260                 265                 270 gaa cct agt aac agc cat atg gtg aag tct tac tcg ttg cta ttt aga               921
Glu Pro Ser Asn Ser His Met Val Lys Ser Tyr Ser Leu Leu Phe Arg
275                 280                 285                 290 gtg act cgt cca gga aga aga gag ttt aat gga atg att aat gga gaa               969
Val Thr Arg Pro Gly Arg Arg Glu Phe Asn Gly Met Ile Asn Gly Glu
             295                 300                 305
```

-continued

| | | |
|---|---|---|
| acc aat gaa aat att gat gtc aat gaa gag ctt cca gcc aga aga aaa<br>Thr Asn Glu Asn Ile Asp Val Asn Glu Glu Leu Pro Ala Arg Arg Lys<br>310                         315                    320 | 1017 | |
| cga aat cgt gag gat ggg gaa aag aca ttt gtt gca caa atg aca gta<br>Arg Asn Arg Glu Asp Gly Glu Lys Thr Phe Val Ala Gln Met Thr Val<br>325                       330                   335 | 1065 | |
| ttt gat aaa aac agg cgc tta cag ctt tta gat ggg gaa tat gaa gta<br>Phe Asp Lys Asn Arg Arg Leu Gln Leu Leu Asp Gly Glu Tyr Glu Val<br>340                       345                   350 | 1113 | |
| gcc atg cag gaa atg gaa gaa tgt cca ata agc aag aaa aga gca aca<br>Ala Met Gln Glu Met Glu Glu Cys Pro Ile Ser Lys Lys Arg Ala Thr<br>355                       360                   365                  370 | 1161 | |
| tgg gag act att ctt gat ggg aag agg ctg cct cca ttc gaa aca ttt<br>Trp Glu Thr Ile Leu Asp Gly Lys Arg Leu Pro Pro Phe Glu Thr Phe<br>                        375                   380                   385 | 1209 | |
| tct cag gga cct acg ttg cag ttc act ctt cgt tgg aca gga gag acc<br>Ser Gln Gly Pro Thr Leu Gln Phe Thr Leu Arg Trp Thr Gly Glu Thr<br>                       390                   395                   400 | 1257 | |
| aat gat aaa tct acg gct cct att gcc aaa cct ctt gcc act aga aat<br>Asn Asp Lys Ser Thr Ala Pro Ile Ala Lys Pro Leu Ala Thr Arg Asn<br>405                       410                   415 | 1305 | |
| tca gag agt ctc cat cag gaa aac aag cct ggt tca gtt aaa cct act<br>Ser Glu Ser Leu His Gln Glu Asn Lys Pro Gly Ser Val Lys Pro Thr<br>420                       425                   430 | 1353 | |
| caa act att gct gtt aaa gaa tca ttg act aca gat cta caa aca aga<br>Gln Thr Ile Ala Val Lys Glu Ser Leu Thr Thr Asp Leu Gln Thr Arg<br>435                       440                   445                  450 | 1401 | |
| aaa gaa aag gat act cca aat gaa aac cga caa aaa tta aga ata ttt<br>Lys Glu Lys Asp Thr Pro Asn Glu Asn Arg Gln Lys Leu Arg Ile Phe<br>                        455                   460                   465 | 1449 | |
| tat cag ttt ctc tat aac aac aat aca agg caa caa act gaa gca aga<br>Tyr Gln Phe Leu Tyr Asn Asn Asn Thr Arg Gln Gln Thr Glu Ala Arg<br>                       470                   475                   480 | 1497 | |
| gat gac ctg cat tgc cct tgg tgt act ctg aac tgc cgc aaa ctt tat<br>Asp Asp Leu His Cys Pro Trp Cys Thr Leu Asn Cys Arg Lys Leu Tyr<br>485                       490                   495 | 1545 | |
| agt tta ctc aag cat ctt aaa ctc tgc cat agc aga ttt atc ttc aac<br>Ser Leu Leu Lys His Leu Lys Leu Cys His Ser Arg Phe Ile Phe Asn<br>500                       505                   510 | 1593 | |
| tat gtt tat cat cca aaa ggt gct agg ata gat gtt tct atc aat gag<br>Tyr Val Tyr His Pro Lys Gly Ala Arg Ile Asp Val Ser Ile Asn Glu<br>515                       520                   525                  530 | 1641 | |
| tgt tat gat ggc tcc tat gca gga aat cct cag gat att cat cgc caa<br>Cys Tyr Asp Gly Ser Tyr Ala Gly Asn Pro Gln Asp Ile His Arg Gln<br>                        535                   540                   545 | 1689 | |
| cct gga ttt gct ttt agt cgc aac gga cca gtt aag aga aca cct atc<br>Pro Gly Phe Ala Phe Ser Arg Asn Gly Pro Val Lys Arg Thr Pro Ile<br>                       550                   555                  560 | 1737 | |
| aca cat att ctt gtg tgc agg cca aaa cga aca aaa gca agc atg tct<br>Thr His Ile Leu Val Cys Arg Pro Lys Arg Thr Lys Ala Ser Met Ser<br>565                       570                   575 | 1785 | |
| gaa ttt ctt gaa tct gaa gat ggg gaa gta gaa cag caa aga aca tat<br>Glu Phe Leu Glu Ser Glu Asp Gly Glu Val Glu Gln Gln Arg Thr Tyr<br>580                       585                   590 | 1833 | |
| agt agt ggc cac aat cgt ctg tat ttc cat agt gat acc tgc tta cct<br>Ser Ser Gly His Asn Arg Leu Tyr Phe His Ser Asp Thr Cys Leu Pro<br>595                       600                   605                  610 | 1881 | |
| ctc cgt cca caa gaa atg gaa gta gat agt gaa gat gaa aag gat cct<br>Leu Arg Pro Gln Glu Met Glu Val Asp Ser Glu Asp Glu Lys Asp Pro | 1929 | |

-continued

```
                615                 620                 625
gaa tgg cta aga gaa aaa acc att aca caa att gaa gag ttt tct gat    1977
Glu Trp Leu Arg Glu Lys Thr Ile Thr Gln Ile Glu Glu Phe Ser Asp
            630                 635                 640 gtt aat gaa gga gag aaa gaa gtg atg aaa ctc tgg aat ctc cat gtc    2025
Val Asn Glu Gly Glu Lys Glu Val Met Lys Leu Trp Asn Leu His Val
        645                 650                 655 atg aag cat ggg ttt att gct gac aat caa atg aat cat gcc tgt atg    2073
Met Lys His Gly Phe Ile Ala Asp Asn Gln Met Asn His Ala Cys Met
    660                 665                 670 ctg ttt gta gaa aat tat gga cag aaa ata att aag aag aat tta tgt    2121
Leu Phe Val Glu Asn Tyr Gly Gln Lys Ile Ile Lys Lys Asn Leu Cys
675                 680                 685                 690 cga aac ttc atg ctt cat cta gtc agc atg cat gac ttt aat ctt att    2169
Arg Asn Phe Met Leu His Leu Val Ser Met His Asp Phe Asn Leu Ile
                695                 700                 705 agc ata atg tca ata gat aaa gct gtt acc aag ctc cgt gaa atg cag    2217
Ser Ile Met Ser Ile Asp Lys Ala Val Thr Lys Leu Arg Glu Met Gln
            710                 715                 720 caa aaa tta gaa aag ggg gaa tct gct tcc cct gca aac gaa gaa ata    2265
Gln Lys Leu Glu Lys Gly Glu Ser Ala Ser Pro Ala Asn Glu Glu Ile
        725                 730                 735 act gaa gaa caa aat ggg aca gca aat gga ttt agt gaa att aac tca    2313
Thr Glu Glu Gln Asn Gly Thr Ala Asn Gly Phe Ser Glu Ile Asn Ser
    740                 745                 750 aaa gag aaa gct ttg gaa aca gat agt gtc tca ggg gtt tca aaa cag    2361
Lys Glu Lys Ala Leu Glu Thr Asp Ser Val Ser Gly Val Ser Lys Gln
755                 760                 765                 770 agc aaa aaa caa aaa ctc tgaaaagctc taacccatg ttatggacaa             2409
Ser Lys Lys Gln Lys Leu
                775 acactgaaat tacattttag ggaattcatc ctctaagaat tatgtttttg tttttaatca    2469 tatgttccaa acaggcactg ttagatgaag taaatgattt caacaaggat atttgtatca    2529 gggttctact tcacttcatt atgcagcatt acatgtatat cacttttatt gatgtcatta    2589 aaacattctg tactttaagc atgaaaagca atatttcaaa gtattttaa actcaacaaa     2649 tgtcatcaaa tatgttgaat tgatctagaa attatttcat atataaatca gaattttttt    2709 gcatttatga acggctgttt ttctactttg taattgtgag acattttctt ggggagggaa    2769 aattggaatg gttccctttt ttagaaattg aagtggtctt catatgtcaa ctacagaaaa    2829 ggaaaaaaat agaaattgaa ggattttat gaaattatat gcattacta tttgcagtca      2889 aactttgatc cttgttttg aaatcatttg tcaattcgga atgaaaaatt ataatgtaat     2949 tttacattac ataagttcct tttacaatta aaaaatagca cttcttcatc ttatgcctgt    3009 ttgagaagat attaaatttt cacattgttg acagtgaaat gctatgttgg tttataagat    3069 tacagaccat ttgttttcat gtggataatt ttagtgcatt gctcacccgg tatgtttttt    3129 ttttttaact tgaacatttt gcttgttttg ttttctttt ttaattagat aatcacacgg     3189 aaaattaagc tgttcatatc tttaaattag gattgcaaac caaggaaaga acgcatttga    3249 gatttttaaga tgtcacttat aaggggagaa gtgttcttaa aaagtcaacc agaaaactgt   3309 tatgcctttt atttgtttgc aaggatgtct ttgtaatgtg tttcatgaat agaatatcca    3369 atagagataa gctgacttga atcattttga gcaattttgc cctgtgttat atgtgtttca    3429 cgcacatatt tgcagttgga ttttctccaa cagaaagtgg attcactact ggcacattaa    3489 caagcaccaa taggtttttta ttccaactcc gagcactgtg gttgagtaac atcacctcaa   3549
```

```
ttttttatta tccttaaaga tattgcattt tcatattctt tatttataaa ggatcaatgc   3609
tgctgtaaat acaggtattt ttaatttaa aatttcattc caccaccatc agatgcagtt   3669
ccctattttg tttaatgaag ggatatataa gctttctaat ggtgtcttca gaaatttata   3729
aaatgtaaat actgatttga ctggtcttta agatgtgttt aactgtgagg ctatttaacg   3789
aatagtgtgg atgtgatttg tcatccagta ttaagttctt agtcattgat ttttgtgttt   3849
aaaaaaaaat aggaaagagg gaaactgcag ctttcattac agattccttg attggtaagc   3909
tctccaaatg atgagttcta gtaaactctg attttttgcct ctggatagta gatctcgagc   3969
gtttatctcg ggctttaatt tgctaaagct gtgcacatat gtaaaaaaa aaaaaaaag   4029 attattttag gggagatgta ggtgtagaat tattgcttat gtcatttctt aagcagttat   4089
gctcttaatg cttaaaagaa ggctagcatt gtttgcacaa aaagttggtg attcccaccc   4149
caaatagtaa taaaattact tctgttgagt aaacttttta tgtcatcgta aaagctggaa   4209
aaatcccttt gtttctattt ataaaaaag tgcttttcta tatgtaccct tgataacaga   4269
ttttgaagaa atcctgtaag atgataaagc atttgaatgg tacagtagat gtaaaaaaaa   4329
ttcagtttaa aagaacattt gtttttacat taaatgttta tttgaaatca aatgattttg   4389
tacataaagt tcaataatat                                              4409
```

<210> SEQ ID NO 8
<211> LENGTH: 776
<212> TYPE: PRT
<213> ORGANISM: Homo sapiens

<400> SEQUENCE: 8

```
Met Thr Gly Ile Ala Ala Ser Phe Phe Ser Asn Thr Cys Arg Phe
 1               5                  10                  15

Gly Gly Cys Gly Leu His Phe Pro Thr Leu Ala Asp Leu Ile Glu His
                20                  25                  30

Ile Glu Asp Asn His Ile Asp Thr Asp Pro Arg Val Leu Glu Lys Gln
                35                  40                  45

Glu Leu Gln Gln Pro Thr Tyr Val Ala Leu Ser Tyr Ile Asn Arg Phe
    50                  55                  60

Met Thr Asp Ala Ala Arg Arg Glu Gln Glu Ser Leu Lys Lys Lys Ile
65                  70                  75                  80

Gln Pro Lys Leu Ser Leu Thr Leu Ser Ser Val Ser Arg Gly Asn
                85                  90                  95

Val Ser Thr Pro Pro Arg His Ser Ser Gly Ser Leu Thr Pro Pro Val
                100                 105                 110

Thr Pro Pro Ile Thr Pro Ser Ser Phe Arg Ser Thr Pro Thr
                115                 120                 125

Glu Pro Thr Gln Ile Tyr Arg Phe Leu Arg Thr Arg Asn Leu Ile Ala
    130                 135                 140

Pro Ile Phe Leu His Arg Thr Leu Thr Tyr Met Ser His Arg Asn Ser
145                 150                 155                 160

Arg Thr Asn Ile Lys Arg Lys Thr Phe Lys Val Asp Asp Met Leu Ser
                165                 170                 175

Lys Val Glu Lys Met Lys Gly Glu Gln Glu Ser His Ser Leu Ser Ala
                180                 185                 190

His Leu Gln Leu Thr Phe Thr Gly Phe Phe His Lys Asn Asp Lys Pro
                195                 200                 205

Ser Pro Asn Ser Glu Asn Glu Gln Asn Ser Val Thr Leu Glu Val Leu
```

-continued

```
                210                 215                 220
Leu Val Lys Val Cys His Lys Lys Arg Lys Asp Val Ser Cys Pro Ile
225                 230                 235                 240

Arg Gln Val Pro Thr Gly Lys Lys Gln Val Pro Leu Ile Pro Asp Leu
                245                 250                 255

Asn Gln Thr Lys Pro Gly Asn Phe Pro Ser Leu Ala Val Ser Ser Asn
                260                 265                 270

Glu Phe Glu Pro Ser Asn Ser His Met Val Lys Ser Tyr Ser Leu Leu
                275                 280                 285

Phe Arg Val Thr Arg Pro Gly Arg Arg Glu Phe Asn Gly Met Ile Asn
290                 295                 300

Gly Glu Thr Asn Glu Asn Ile Asp Val Asn Glu Glu Leu Pro Ala Arg
305                 310                 315                 320

Arg Lys Arg Asn Arg Glu Asp Gly Glu Lys Thr Phe Val Ala Gln Met
                325                 330                 335

Thr Val Phe Asp Lys Asn Arg Arg Leu Gln Leu Leu Asp Gly Glu Tyr
                340                 345                 350

Glu Val Ala Met Gln Glu Met Glu Glu Cys Pro Ile Ser Lys Lys Arg
                355                 360                 365

Ala Thr Trp Glu Thr Ile Leu Asp Gly Lys Arg Leu Pro Pro Phe Glu
370                 375                 380

Thr Phe Ser Gln Gly Pro Thr Leu Gln Phe Thr Leu Arg Trp Thr Gly
385                 390                 395                 400

Glu Thr Asn Asp Lys Ser Thr Ala Pro Ile Ala Lys Pro Leu Ala Thr
                405                 410                 415

Arg Asn Ser Glu Ser Leu His Gln Glu Asn Lys Pro Gly Ser Val Lys
                420                 425                 430

Pro Thr Gln Thr Ile Ala Val Lys Glu Ser Leu Thr Thr Asp Leu Gln
                435                 440                 445

Thr Arg Lys Glu Lys Asp Thr Pro Asn Glu Asn Arg Gln Lys Leu Arg
450                 455                 460

Ile Phe Tyr Gln Phe Leu Tyr Asn Asn Asn Thr Arg Gln Gln Thr Glu
465                 470                 475                 480

Ala Arg Asp Asp Leu His Cys Pro Trp Cys Thr Leu Asn Cys Arg Lys
                485                 490                 495

Leu Tyr Ser Leu Leu Lys His Leu Lys Leu Cys His Ser Arg Phe Ile
                500                 505                 510

Phe Asn Tyr Val Tyr His Pro Lys Gly Ala Arg Ile Asp Val Ser Ile
                515                 520                 525

Asn Glu Cys Tyr Asp Gly Ser Tyr Ala Gly Asn Pro Gln Asp Ile His
                530                 535                 540

Arg Gln Pro Gly Phe Ala Phe Ser Arg Asn Gly Pro Val Lys Arg Thr
545                 550                 555                 560

Pro Ile Thr His Ile Leu Val Cys Arg Pro Lys Arg Thr Lys Ala Ser
                565                 570                 575

Met Ser Glu Phe Leu Glu Ser Glu Asp Gly Glu Val Glu Gln Gln Arg
                580                 585                 590

Thr Tyr Ser Ser Gly His Asn Arg Leu Tyr Phe His Ser Asp Thr Cys
                595                 600                 605

Leu Pro Leu Arg Pro Gln Glu Met Glu Val Asp Ser Glu Asp Glu Lys
                610                 615                 620

Asp Pro Glu Trp Leu Arg Glu Lys Thr Ile Thr Gln Ile Glu Glu Phe
625                 630                 635                 640
```

```
Ser Asp Val Asn Glu Gly Glu Lys Glu Val Met Lys Leu Trp Asn Leu
            645                 650                 655
His Val Met Lys His Gly Phe Ile Ala Asp Asn Gln Met Asn His Ala
        660                 665                 670
Cys Met Leu Phe Val Glu Asn Tyr Gly Gln Lys Ile Ile Lys Lys Asn
        675                 680                 685
Leu Cys Arg Asn Phe Met Leu His Leu Val Ser Met His Asp Phe Asn
    690                 695                 700
Leu Ile Ser Ile Met Ser Ile Asp Lys Ala Val Thr Lys Leu Arg Glu
705                 710                 715                 720
Met Gln Gln Lys Leu Glu Lys Gly Glu Ser Ala Ser Pro Ala Asn Glu
                725                 730                 735
Glu Ile Thr Glu Gln Asn Gly Thr Ala Asn Gly Phe Ser Glu Ile
            740                 745                 750
Asn Ser Lys Glu Lys Ala Leu Glu Thr Asp Ser Val Ser Gly Val Ser
            755                 760                 765
Lys Gln Ser Lys Lys Gln Lys Leu
    770                 775
```

<210> SEQ ID NO 9
<211> LENGTH: 2328
<212> TYPE: DNA
<213> ORGANISM: Homo sapiens

<400> SEQUENCE: 9

```
atgacaggca tcgccgccgc ctccttcttc tccaatacct gccgattcgg gggctgcgga      60
ctccacttcc ccaccctggc cgacctcatc gagcacatcg aggacaacca catcgataca     120
gatccacggg ttttagaaaa acaagaatta cagcagccaa cctatgttgc cctgagttac     180
ataaatagat tcatgacaga tgctgcccgc cgagagcagg agtccctaaa gaagaagatt     240
cagccgaagc tctcgctgac tctgtccagc tcagtgtctc gagggaatgt gtccactccc     300
ccacgccaca gcagtggaag ccttactccc ccgtgaccc cacccatcac ccctcctct       360
tcattccgca gcagcactcc gacagagcca acacagatct atagatttct tcgaactcgg     420
aatctcatag caccaatatt tttgcacaga actcttactt acatgtctca tcgaaactcc     480
agaacaaaca tcaaaaggaa aacatttaaa gttgatgata tgttatcaaa agtagagaaa     540
atgaaaggag agcaagaatc tcatagcttg tcagctcatt tgcagcttac gtttactggt     600
ttcttccaca aaaatgataa gccatcacca aactcagaaa atgaacaaaa ttctgttacc     660
ctggaagtcc tgcttgtgaa agtttgccac aaaaaaagaa aggatgtaag ttgtccaata     720
aggcaagttc ccacaggtaa aaagcaggtg cctttgattc ctgacctcaa tcaaacaaaa     780
cccggaaatt tcccgtccct tgcagtttcc agtaatgaat ttgaacctag taacagccat     840
atggtgaagt cttactcgtt gctatttaga gtgactcgtc caggaagaag agagtttaat     900
ggaatgatta tggagaaac caatgaaaat attgatgtca atgaagagct ccagccaga      960
agaaaacgaa atcgtgagga tgggaaaag acatttgttg cacaaatgac agtatttgat    1020
aaaaacaggc gcttacagct tttagatggg gaatatgaag tagccatgca ggaaatggaa    1080
gaatgtccaa taagcaagaa aagagcaaca tgggagacta tcttgatgg gaagaggctg    1140
cctccattcg aaacattttc tcagggacct acgttgcagt tcactcttcg ttggacagga    1200
gagaccaatg ataaatctac ggctcctatt gccaaacctc ttgccactag aaattcagag    1260
agtctccatc aggaaaacaa gcctggttca gttaaaccta ctcaaactat tgctgttaaa    1320
```

-continued

```
gaatcattga ctacagatct acaaacaaga aaagaaaagg atactccaaa tgaaaaccga    1380
caaaaattaa gaatatttta tcagtttctc tataacaaca atacaaggca acaaactgaa    1440
gcaagagatg acctgcattg cccttggtgt actctgaact gccgcaaact ttatagttta    1500
ctcaagcatc ttaaactctg ccatagcaga tttatcttca actatgttta tcatccaaaa    1560
ggtgctagga tagatgtttc tatcaatgag tgttatgatg ctcctatgc aggaaatcct     1620 caggatattc atcgccaacc tggatttgct tttagtcgca acggaccagt taagagaaca    1680
cctatcacac atattcttgt gtgcaggcca aaacgaacaa agcaagcat gtctgaattt     1740 cttgaatctg aagatgggga agtagaacag caaagaacat atagtagtgg ccacaatcgt    1800
ctgtatttcc atagtgatac ctgcttacct ctccgtccac aagaaatgga agtagatagt    1860
gaagatgaaa aggatcctga atggctaaga gaaaaaacca ttacacaaat tgaagagttt    1920
tctgatgtta atgaaggaga gaaagaagtg atgaaactct ggaatctcca tgtcatgaag    1980
catgggttta ttgctgacaa tcaaatgaat catgcctgta tgctgtttgt agaaaattat    2040
ggacagaaaa taattaagaa gaatttatgt cgaaacttca tgcttcatct agtcagcatg    2100 catgactta atcttattag cataatgtca atagataaag ctgttaccaa gctccgtgaa    2160
atgcagcaaa aattagaaaa gggggaatct gcttcccctg caaacgaaga ataactgaa    2220 gaacaaaatg ggacagcaaa tggatttagt gaaattaact caaagagaa agctttggaa    2280 acagatagtg tctcaggggt ttcaaaacag agcaaaaaac aaaaactc                 2328
```

<210> SEQ ID NO 10
<211> LENGTH: 20
<212> TYPE: DNA
<213> ORGANISM: Artificial Sequence
<220> FEATURE:
<223> OTHER INFORMATION: primer for PCR

<400> SEQUENCE: 10
ccacagcagt ggaagcctta                                                20

<210> SEQ ID NO 11
<211> LENGTH: 22
<212> TYPE: DNA
<213> ORGANISM: Artificial Sequence
<220> FEATURE:
<223> OTHER INFORMATION: primer for PCR

<400> SEQUENCE: 11
gcttctcttc ccctccattc at                                             22

<210> SEQ ID NO 12
<211> LENGTH: 20
<212> TYPE: DNA
<213> ORGANISM: Artificial Sequence
<220> FEATURE:
<223> OTHER INFORMATION: primer for PCR

<400> SEQUENCE: 12
atcaccccct cctcttcatt                                                20

<210> SEQ ID NO 13
<211> LENGTH: 20
<212> TYPE: DNA
<213> ORGANISM: Artificial Sequence
<220> FEATURE:
<223> OTHER INFORMATION: primer for PCR

<400> SEQUENCE: 13
ggactcatcg ctgtccgact                                           20

<210> SEQ ID NO 14
<211> LENGTH: 22
<212> TYPE: DNA
<213> ORGANISM: Artificial Sequence
<220> FEATURE:
<223> OTHER INFORMATION: primer for PCR

<400> SEQUENCE: 14
gttactcggc ctcctcctcc tc                                        22

<210> SEQ ID NO 15
<211> LENGTH: 26
<212> TYPE: DNA
<213> ORGANISM: Artificial Sequence
<220> FEATURE:
<223> OTHER INFORMATION: primer for PCR

<400> SEQUENCE: 15
ggttcaaatt cattactgga aactgc                                    26

<210> SEQ ID NO 16
<211> LENGTH: 22
<212> TYPE: DNA
<213> ORGANISM: Artificial Sequence
<220> FEATURE:
<223> OTHER INFORMATION: primer for PCR

<400> SEQUENCE: 16
gagcttttcc tccaggcctt tg                                        22

<210> SEQ ID NO 17
<211> LENGTH: 21
<212> TYPE: DNA
<213> ORGANISM: Artificial Sequence
<220> FEATURE:
<223> OTHER INFORMATION: primer for PCR

<400> SEQUENCE: 17
ccgggttttg tttgattgag g                                         21

<210> SEQ ID NO 18
<211> LENGTH: 20
<212> TYPE: DNA
<213> ORGANISM: Artificial Sequence
<220> FEATURE:
<223> OTHER INFORMATION: primer for PCR

<400> SEQUENCE: 18
cacatcgctc agacaccatg                                           20

<210> SEQ ID NO 19
<211> LENGTH: 20
<212> TYPE: DNA
<213> ORGANISM: Artificial Sequence
<220> FEATURE:
<223> OTHER INFORMATION: primer for PCR

<400> SEQUENCE: 19
gccatggaat ttgccatggg                                           20

<210> SEQ ID NO 20
<211> LENGTH: 20

```
-continued

<212> TYPE: DNA
<213> ORGANISM: Artificial Sequence
<220> FEATURE:
<223> OTHER INFORMATION: primer for PCR

<400> SEQUENCE: 20
cacgccacag cagtggaagc                                          20

<210> SEQ ID NO 21
<211> LENGTH: 25
<212> TYPE: DNA
<213> ORGANISM: Artificial Sequence
<220> FEATURE:
<223> OTHER INFORMATION: primer for PCR

<400> SEQUENCE: 21
tttgttctgg agtttcgatg agaca                                    25

<210> SEQ ID NO 22
<211> LENGTH: 20
<212> TYPE: DNA
<213> ORGANISM: Artificial Sequence
<220> FEATURE:
<223> OTHER INFORMATION: primer for PCR

<400> SEQUENCE: 22
cccacccatc accccctcct                                          20

<210> SEQ ID NO 23
<211> LENGTH: 27
<212> TYPE: DNA
<213> ORGANISM: Artificial Sequence
<220> FEATURE:
<223> OTHER INFORMATION: primer for PCR

<400> SEQUENCE: 23
ggtgctatga gattccgagt tcgaaga                                  27
```